(12) United States Patent
Stripecke et al.

(10) Patent No.: US 10,272,111 B2
(45) Date of Patent: Apr. 30, 2019

(54) INDUCED DENDRITIC CELLS AND USES THEREOF

(71) Applicant: MEDIZINISCHE HOCHSCHULE HANNOVER, Hannover (DE)

(72) Inventors: Renata Stripecke, Hannover (DE); Gustavo Salguero-Lopez, Hannover (DE); Anusara Daenthanasanmak, Hannover (DE); Arnold Ganser, Hannover (DE)

(73) Assignee: Medizinische Hochschule Hannover, Hannover (DE)

( * ) Notice: Subject to any disclaimer, the term of this patent is extended or adjusted under 35 U.S.C. 154(b) by 0 days.

(21) Appl. No.: 14/820,645

(22) Filed: Aug. 7, 2015

(65) Prior Publication Data

US 2016/0038541 A1 Feb. 11, 2016

Related U.S. Application Data

(63) Continuation of application No. PCT/EP2014/051422, filed on Jan. 24, 2014, which is a continuation of application No. PCT/EP2013/052485, filed on Feb. 7, 2013.

(51) Int. Cl.
| | | |
|---|---|---|
| *A61K 35/15* | (2015.01) | |
| *C12N 5/0784* | (2010.01) | |
| *A61K 49/00* | (2006.01) | |
| *A61K 35/12* | (2015.01) | |
| *A61K 39/00* | (2006.01) | |

(52) U.S. Cl.
CPC .......... *A61K 35/15* (2013.01); *A61K 49/0008* (2013.01); *C12N 5/0639* (2013.01); *A61K 2035/122* (2013.01); *A61K 2035/124* (2013.01); *A61K 2039/5154* (2013.01); *C12N 2501/22* (2013.01); *C12N 2501/24* (2013.01); *C12N 2502/1121* (2013.01); *C12N 2510/00* (2013.01)

(58) Field of Classification Search
CPC ........ A61K 2035/122; A61K 2035/124; A61K 2039/5154; A61K 35/15; A61K 49/0008; C12N 2501/22; C12N 2501/24; C12N 2502/1121; C12N 2510/00; C12N 5/0639
USPC ..... 435/325, 372, 375; 424/184.1; 800/3, 11
See application file for complete search history.

(56) References Cited

FOREIGN PATENT DOCUMENTS

WO    2011002727 A1    1/2011
WO    WO 2011/002727 A1 *  1/2011

OTHER PUBLICATIONS

Palma et al., 2012, Nov. 2011 on line, Cancer Immunol. Immunother. 61:865-879.*
Wang et al (2011, Asian. Pac. J. Cancer. Prev. 12:2811-2817; abstract P.1 of 1.*
Zhang et al 2010, Vaccine 28:5114-5127.*
Salguero et al., May 2011, Human Gene Therapy. 22:1209-1224.*
Ma et al (2013, PLOS One 8(7) e69779; pp. 1-8.*
Sundarasetty, et al., "Lentivirus-Induced Dendritic Cells for Immunization Against High-Risk WT1 + Acute Myeloid Leukemia", Human Gene Therapy, 24(2):220-237, 2013.
Daenthanasanmak, et al., "Integrase-defective lentiviral vectors encoding cytokines induce differentiation of human dendritic cells and stimulate multivalent immune responsesand", Vaccine, Elsevier Ltd, GB, 30(34):5118-5131, 2012.
Pincha, et al., "Identity, Potency, In Vivo Viability, and Scaling Up Production of Lentiviral Vector-Induced Dendritic Cells for Melanoma Immunotherapy", Human Gene Therapy Methods, 23(1):38-55, 2012.
Salguero, et al., "Preconditioning Therapy with Lentiviral Vector-Programmed Dendritic Cells Accelerates the Homeostatic Expansion of Antigen-Reactive Human T Cells in NOD.Rag1 −/− .IL-2r[gamma]c −/− mice", Human Gene Therapy, 22(10):1209-1224, 2011.
Pincha, et al., "Lentiviral vectors for induction of self-differentiation and conditional ablation of dendritic cells", Gene Therapy, 18(8):750-764, 2011.
Liu Ningfei et al., "Lymph Node Transplantation in Rats: Changes in Cellular Architecture and Possible Influence on Its Histological and Functional Restoration", Chinese Journal of Reparative and Reconstructive Surgery, 6(1), 1992. (abstract only).

* cited by examiner

*Primary Examiner* — Janet L Epps-Smith
(74) *Attorney, Agent, or Firm* — Joseph C. Zucchero; Carolyn S. Elmore; Elmore Patent Law Group, P.C.

(57) ABSTRACT

The present invention relates to cells engineered to express at least one cytokine and at least one antigen which induces the self differentiation of dendritic cell (DC) progenitor cells into functional antigen-presenting induced DC (iDC). Moreover, therapeutic uses of said iDC for regenerating the immune system after transplantation of hematopoietic stem cells are disclosed. Said iDC are also useful for generating mice with a functional endogenously regenerated humanized immune system producing antigen-specific T and B cell responses which can be used as animal models for the study of the human adaptive immune responses.

8 Claims, 37 Drawing Sheets

Specification includes a Sequence Listing.

☐ Con-IFN/pp65
■ Smyle/pp65

Development of Regional LN

Development of Distant LN

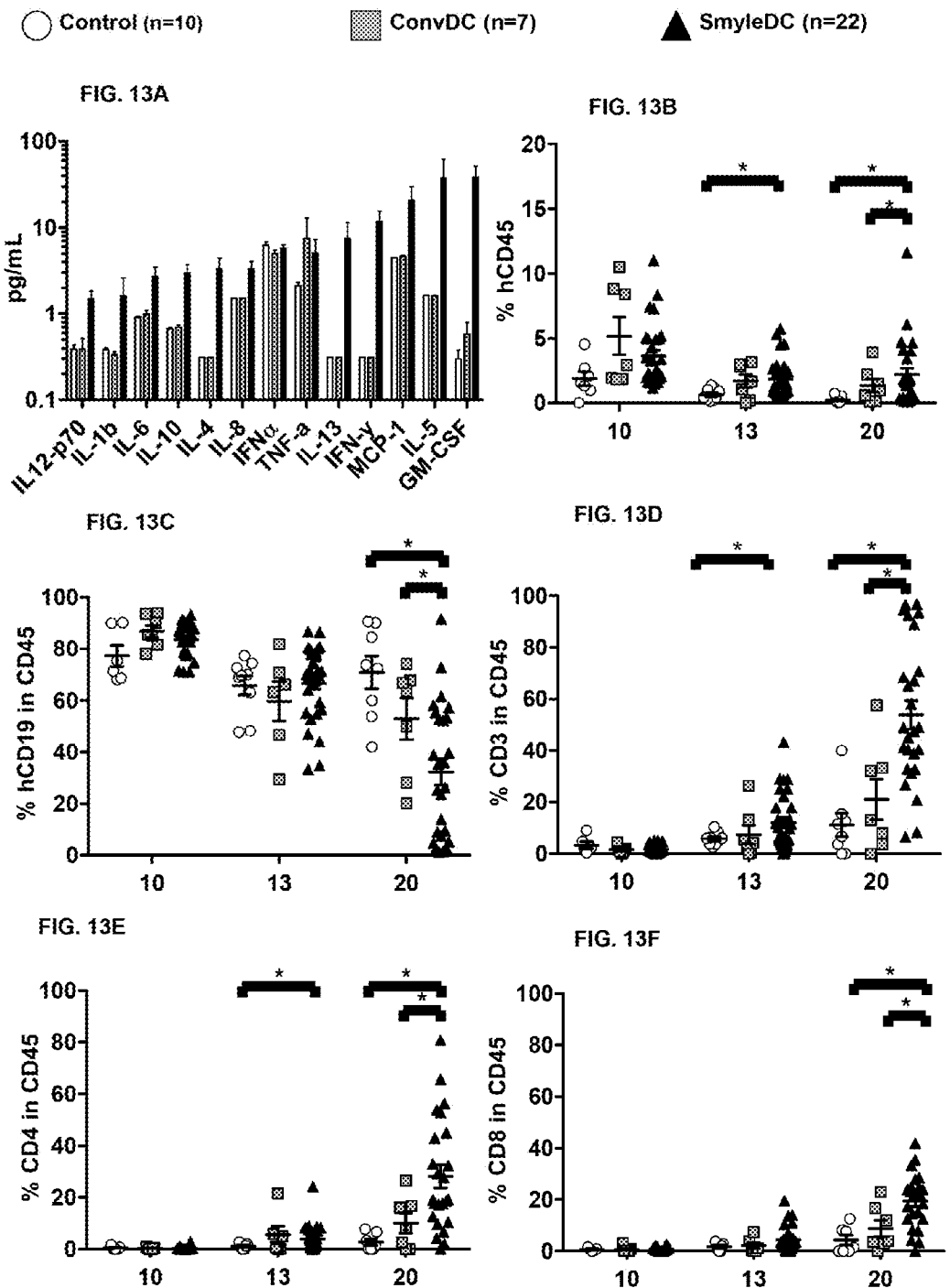

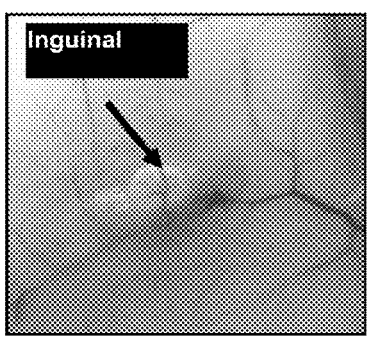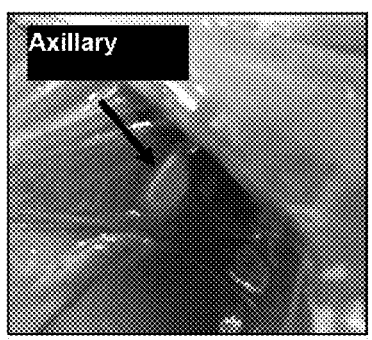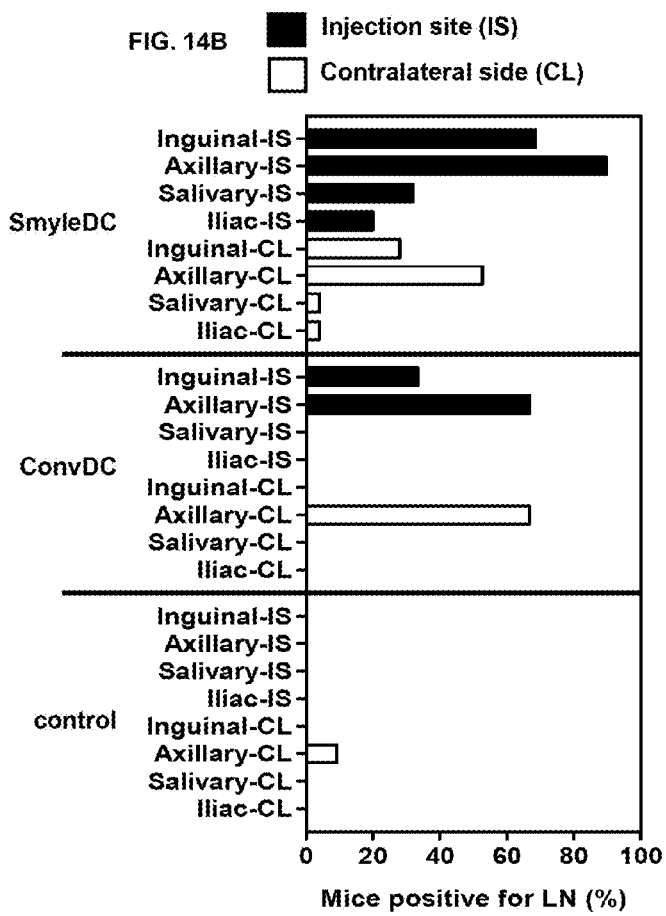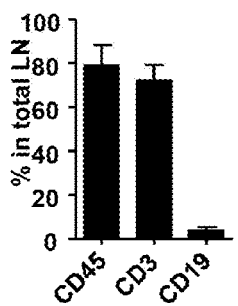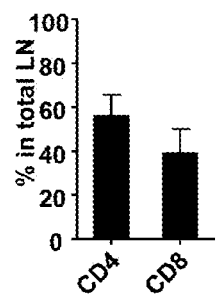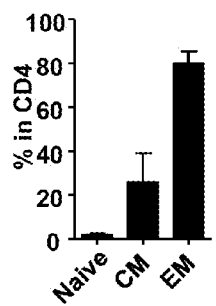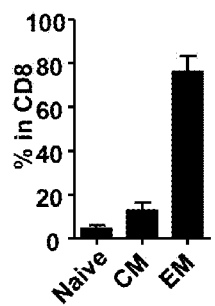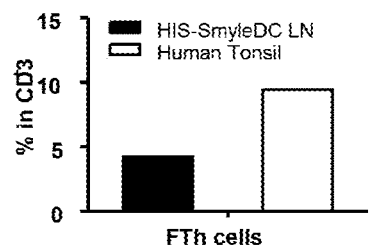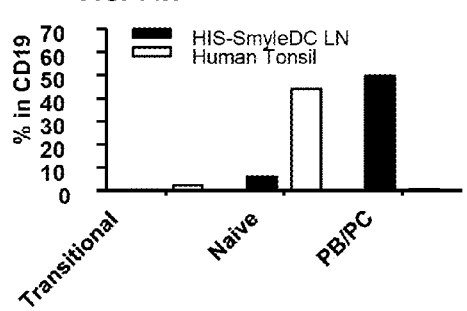

FIG. 17A Human lineages
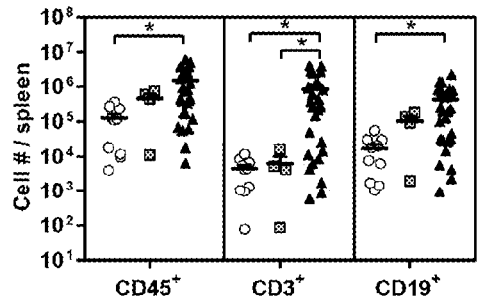
○ Control (n=10)
▩ ConvDC (n=7)
▲ SmyleDC (n=22)
FIG. 17B
CD4 T helper subtypes
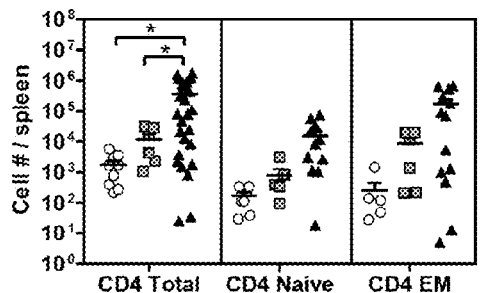
FIG. 17C CD8 T cytotoxic subtypes
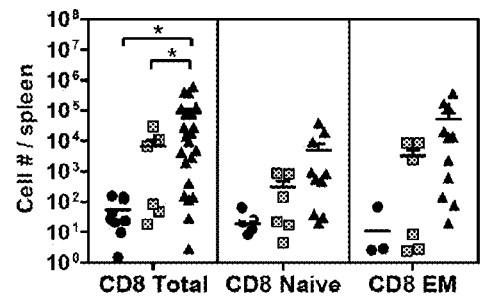
FIG. 17D Follicular T helper cells
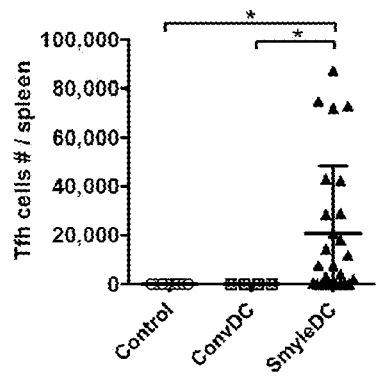
FIG. 17E B cell sybtypes
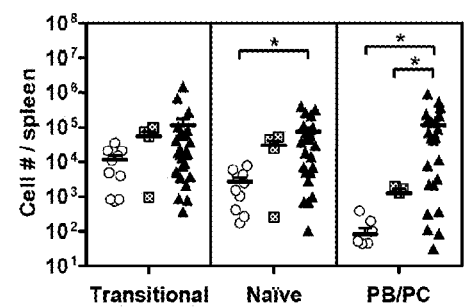

SLE: systemic lupus erythrematosus control plasma

| Rank | DC1 | DC2 | DC3 |
|---|---|---|---|
| | IC-LV | | |
| 1 | ZNF37A | BRUNOL4 | TPTE |
| 2 | KLHL2 | HAAO | USP9Y |
| 3 | INADL | LMBR1 | FLJ21511 |
| 4 | TPTE | CDH8 | HAPLN1 |
| 5 | HAAO | DNAH14 | TNFRSF10B |
| 6 | USP9Y | RTTN | SNTA1 |
| 7 | RPIA | SEL1L | SEL1L |
| 8 | MAMDC2 | KCNA5 | NUDT12 |
| 9 | ZNF37A | ACP5 | FER1L6 |
| 10 | IGFBP7 | PNPLA7 | ZNF774 |
| All other IS | 1111 | 932 | 1427 |

FIG. 23D

| Rank | ID-LV | | |
|---|---|---|---|
| | DC4 | DC5 | DC6 |
| 1 | GOLGA7 | GOLGA7 | GOLGA7 |
| 2 | ZNF37A | ITGAE | ALG10B |
| 3 | TPTE | ILF2 | SYNCRIP |
| 4 | WDR74 | POU3F3 | FCGR1B |
| 5 | FLJ21511 | WDR74 | ZNF33B |
| 6 | WDR74 | STAG3L4 | RCOR3 |
| 7 | NARF | BTRC | LYRM2 |
| 8 | ZIC3 | CDKL5 | SDCCAG1 |
| 9 | MDM4 | LPHN3 | UQCRFS1 |
| 10 | C1orf38 | MIA3 | PRIM2 |
| All other IS | 428 | 592 | 492 |

FIG. 23D cont'd

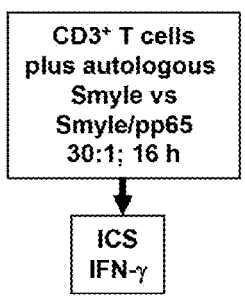
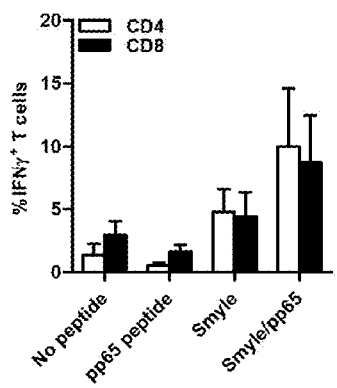
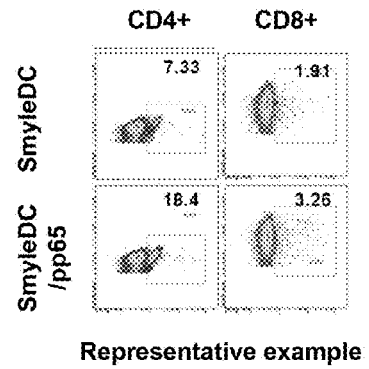
FIG. 25A
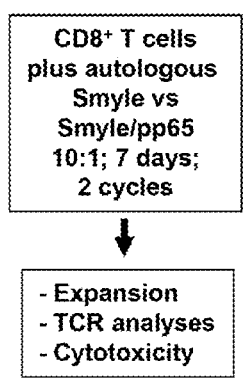
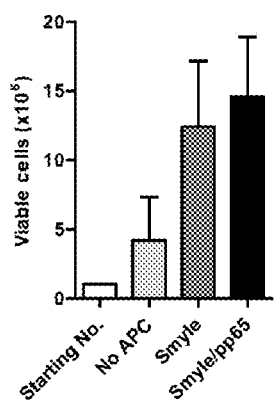
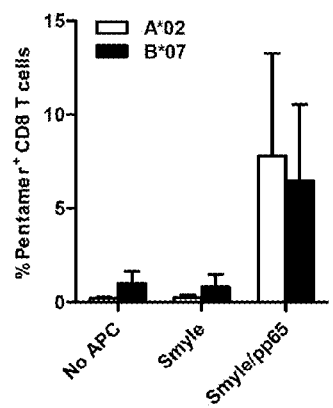
FIG. 25B
FIG. 25C
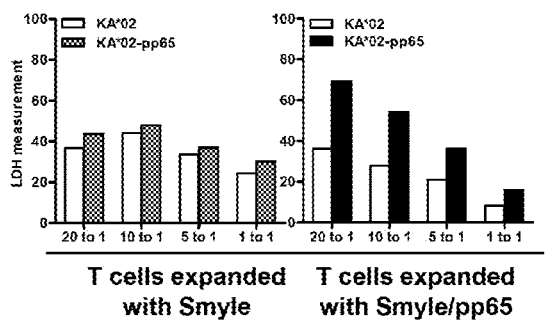
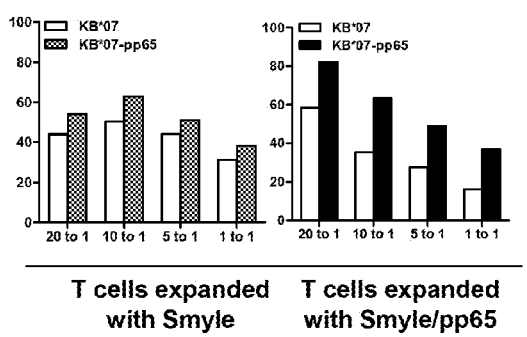

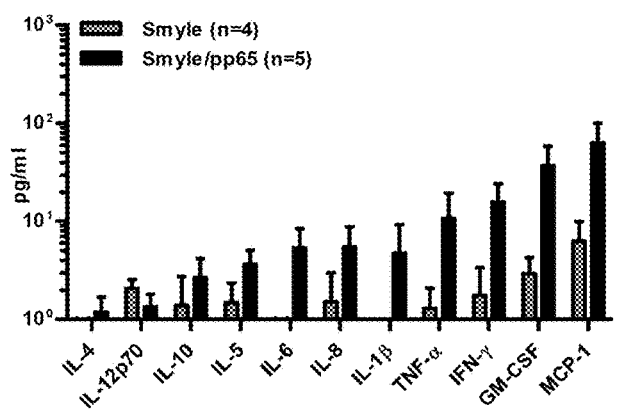
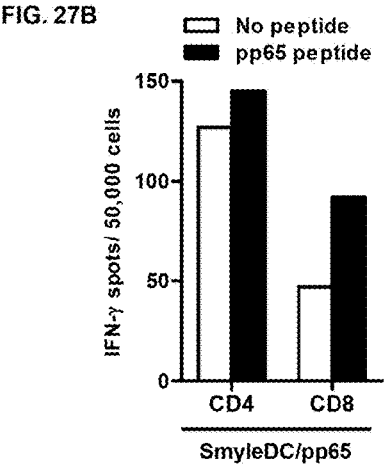
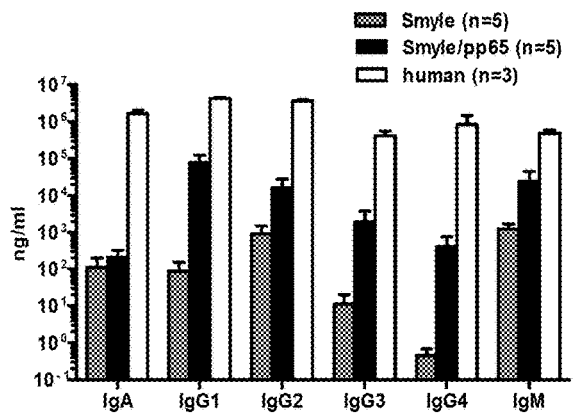
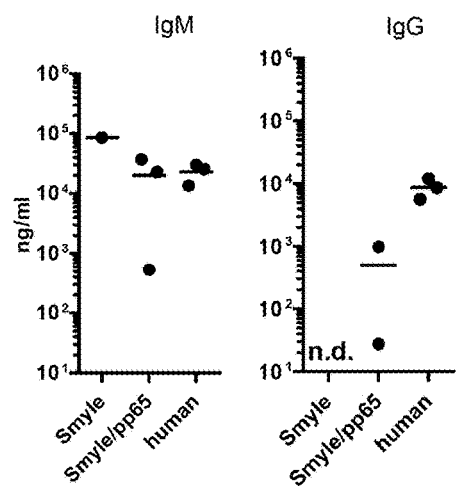

INDUCED DENDRITIC CELLS AND USES THEREOF

RELATED APPLICATIONS

This application is a continuation of International Application No. PCT/EP2014/051422, which designated the United States and was filed on Jan. 24, 2014, published in English, which claims priority to International Application No. PCT/EP2013/052485, which designated the United States and was filed on Feb. 7, 2013, published in English. The entire teachings of the above applications are incorporated herein by reference.

The present invention relates to cells engineered to express at least one cytokine and at least one antigen which induces the self differentiation of dendritic cell (DC) progenitor cells into functional antigen-presenting induced DC (iDC). Moreover, therapeutic uses of said iDC for regenerating the immune system after transplantation of hematopoietic stem cells are disclosed. Said iDC are also useful for generating mice with a functional endogenously regenerated humanized immune system producing antigen-specific T and B cell responses which can be used as animal models for the study of the human adaptive immune responses.

BACKGROUND OF THE INVENTION

Hematopoietic stem cell transplantation (HSCT) has become the standard therapeutic approach for diverse malignant hematopoietic disorders, accounting with high rates of clinical success for chronic (80%) and acute myeloid leukemia (65%) due to long term hematopoietic engraftment and graft versus leukemia effects of the donor graft. However, post-HSCT subjects suffer from profound cellular immunodeficiency the first 100 days post-transplantation and reach full T and B cell reconstitution only after 1 year post-HSCT. Longer periods of cell immune deficiency are associated with subsequent increase of risk for opportunistic viral and fungal infections and relapse (up to 40%) (Seggewiss, R., and H. Einsele, 2010, "Immune reconstitution after allogeneic transplantation and expanding options for immunomodulation: an update." *Blood* 115: 3861-3868; Roncarolo, M. G. et al., 2011, "Clinical tolerance in allogeneic hematopoietic stem cell transplantation." *Immunological reviews* 241: 145-163; Mori, T., and J. Kato, 2010, "Cytomegalovirus infection/disease after hematopoietic stem cell transplantation" *International journal of hematology* 91: 588-595). Thus, strategies to accelerate the recovery of the lymphocyte pool with a broad repertoire of T cell and B cell responses and induce optimal viral immunity in post-HSCT transplanted subjects are required.

Novel advanced therapeutic approaches to induce immune reconstitution in immunodeficient hosts based on passive and active immunization have been developed over the past decade. Yet, suitable in vivo experimental models to address efficacy and biosafety of such therapies are still under development. In order to experimentally recapitulate human immune reconstitution after HSCT in vivo, CD34+ human hematopoietic stem cells (HSC) are transplanted into diverse immunodeficient mouse strains lacking the common interleukin-2 receptor gamma chain (IL2Rγ) (NOD-Rag1nullIL2Rγ$^{null}$-NRG, NOD/LtSz-scid/IL2Rγ$^{null}$-NSG, or NOD/SCID/IL2Rγ$^{null}$-NOG) after sublethal total body irradiation (TBI), resulting in reconstitution of human hematopoietic lineages 8 to 10 weeks after CD34+ cell transfer (Ishikawa, F., et al., 2005, "Development of functional human blood and immune systems in NOD/SCID/IL2 receptor γ chainnull mice." *Blood* 106: 1565-1573). Importantly, regardless the source of HSCs and the method of cell transplantation, humanized mice displayed suboptimal levels of T and B mature lymphocyte reconstitution, lack of antigen specific cellular and humoral responses and overall anergy (Lepus, C. M. et al., 2009, "Comparison of Human Fetal Liver, Umbilical Cord Blood, and Adult Blood Hematopoietic Stem Cell Engraftment in NOD-scid/γc−/−, Balb/c-Rag1−/−γc−/−, and C.B-17-scid/bg Immunodeficient Mice." *Human immunology* 70: 790-802; Andre, M. C. et al, 2010, "Long-term human CD34+ stem cell-engrafted non-obese diabetic/SCID/IL-2R gamma(null) mice show impaired CD8+ T cell maintenance and a functional arrest of immature NK cells." *J Immunol* 185: 2710-2720). Factors that determine the inefficient lymphatic development in humanized mice include the absence of human histocompatibility molecules, impaired thymic function and poor human cytokine environment.

Attempts to solve this problem included delivery of cytokines (O'Connell, R. M. et al., 2010, "Lentiviral Vector Delivery of Human Interleukin-7 (hIL-7) to Human Immune System (HIS) Mice Expands T Lymphocyte Populations." *PLoS One* 5; Chen, Q. et al., 2009, "Expression of human cytokines dramatically improves reconstitution of specific human-blood lineage cells in humanized mice." *Proc Natl Acad Sci USA* 106: 21783-21788), transplantation of fetal lymphatic tissue along with HPCs (Hu, Z., and Y. G. Yang, 2012, "Human lymphohematopoietic reconstitution and immune function in immunodeficient mice receiving cotransplantation of human thymic tissue and CD34+ cells" *Cell Mol Immunol* 9: 232-236; Biswas, S. et al., 2011, "Humoral immune responses in humanized BLT mice immunized with West Nile virus and HIV-1 envelope proteins are largely mediated via human CD5+ B cells." *Immunology* 134: 419-433) and the use of transgenic strains constitutively expressing the major histocompatibility molecules (MHC) class I (Shultz, L. D. et al, 2010, "Generation of functional human T-cell subsets with HLA-restricted immune responses in HLA class I expressing NOD/SCID/IL2rγnull humanized mice." *Proc Natl Acad Sci USA* 107: 13022-13027) and HLA class II (Danner, R. et al., 2011, "Expression of HLA Class II Molecules in Humanized NOD.Rag1KO.IL2RgcKO Mice Is Critical for Development and Function of Human T and B Cells" *PLoS One* 6) or critical hematopoietic cytokines (Willinger, T. et al., 2011, "Human IL-3/GM-CSF knock-in mice support human alveolar macrophage development and human immune responses in the lung" *Proc Natl Acad Sci USA* 108: 2390-2395) have been recently described. These strategies allowed a limited improvement in B and T cell responses against human viral challenges. Importantly, only few reports have described the presence of reconstituted lymphatic structures in HSC-transplanted mice (Singh, M. et al., 2012, "An Improved Protocol for Efficient Engraftment in NOD/LTSZ-SCIDIL-2RγNULL Mice Allows HIV Replication and Development of Anti-HIV Immune Responses" *PLoS One* 7; Marodon, G. et al., 2009, "High diversity of the immune repertoire in humanized NOD.SCID.gamma c−/− mice" *European journal of immunology* 39: 2136-2145; Sun, Z. et al., 2007, "Intrarectal transmission, systemic infection, and CD4+ T cell depletion in humanized mice infected with HIV-1" *J Exp Med* 204: 705-714). Although high quality CD34+HPC from human cord blood or fetal liver were used, thereby reaching high rates of human cell engraftment and reasonable levels of human lymphatic cells, lymph nodes (LN) were barely observed. These data suggest that lack of lymphatic organ regeneration could be playing an important role in the poor lymphoid cell reconstitution observed in humanized mouse models.

DCs play a central role in the induction of adaptive immune responses. Importantly, DC trigger the regeneration and remodeling of tertiary lymphatic structures and play a fundamental role in maintaining the function of LN during active immune responses.

Using lentivirus (LV)-mediated gene transfer, we have developed a method to generate highly viable and potent DCs for cancer immunotherapy (Pincha, M. et al., 2011, "Lentiviral vectors for induction of self-differentiation and conditional ablation of dendritic cells" *Gene therapy* 18: 750-764; Koya, R. C. et al., 2007 "Lentiviral vector-mediated autonomous differentiation of mouse bone marrow cells into immunologically potent dendritic cell vaccines" *Molecular Therapy* 15: 971-980". LV-induced DC showed high levels of engraftment and potent capacity to stimulate antigen specific responses and protect against melanoma in vivo. Recently, we demonstrated that integrase-defective (ID) LV gene delivery of human granulocyte-macrophage colony stimulation factor (GM-CSF) and interferon (IFN)-α into human monocytes resulted in autonomous differentiated and highly viable dendritic cells (Daenthanasanmak, A. et al., 2012, "Integrase-defective lentiviral vectors encoding cytokines induce differentiation of human dendritic cells and stimulate multivalent immune responses in vitro and in vivo" *Vaccine* 30: 5118-5131).

Thus, the problem underlying the present invention can be viewed as the provision of means and methods which improve the regeneration of the immune system after transplantation of hematopoietic stem cells.

The problem is solved by the embodiments described in the claims and the description below.

SUMMARY OF THE INVENTION

In one aspect, the present invention relates to an induced dendritic cell (iDC) engineered to express
 a) at least one cytokine which induces the self-differentiation of human DC progenitor cells into DCs; and
 b) at least one antigen;
for use as a medicament.

In another aspect, the present invention relates to an iDC engineered to express
 a) at least one cytokine which induces the self-differentiation of human DC progenitor cells into DCs; and
 b) at least one antigen;
for use in the regeneration of the immune system of an immunodeficient subject following transplantation of HSC.

In yet another aspect, the present invention relates to an iDC engineered to express
 a) at least one cytokine which induces the self-differentiation of human DC progenitor cells into DCs; and
 b) at least one antigen;
for use as a medicament for the treatment of cancer which spreads lymphatically or a disease caused by a lymphotrophic pathogen.

In yet another aspect, the present invention relates to a method for regenerating an immune system in an immunodeficient subject comprising the steps of
 a) transplanting hematopoietic stem cells to the subject; and
 b) administering to the subject an iDC engineered to express at least one antigen and at least one cytokine which induces the self-differentiation of DC progenitor cells into DCs.

In yet another aspect, the present invention relates to an animal model with a functional xenogeneic immune system produced by the method of the present invention.

In yet another aspect, the present invention relates to the use of a mouse with a humanized immune system produced by the method of the present invention for the study of the human immune system or for the testing of drugs, implants or devices for their use in humans.

In yet another aspect, the present invention relates to an iDC comprising at least one integrase-defective lentiviral vector, wherein said vector mediates expression of
 a) at least one cytokine which induces the self-differentiation of human DC progenitor cells into DCs; and
 b) at least one antigen.

In yet another embodiment, the present invention relates to a method for generating iDCs comprising the steps of
 a) isolating progenitor cells from a sample derived from a suitable donor;
 b) engineering the cells to achieve expression of at least one cytokine which induces the self-differentiation of human dendritic cell (DC) progenitor cells into DCs and at least one antigen.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

Description of the iDC of the Present Invention

The present invention relates to an iDC engineered to express
 a) at least one cytokine which induces the self-differentiation of human dendritic cell (DC) progenitor cells into DCs; and
 b) at least one antigen.

An iDC useful for the methods and uses described further below in this application is a dendritic cell which is induced to self-differentiate by the expression of at least one cytokine and at least one antigen.

The term "self-differentiation" of a dendritic cell refers the development of a dendritic cell from a suitable progenitor cell which is stimulated by endogenous expression of at least one cytokine and at least one antigen. The term "self-differentiation" does not exclude the addition of cytokines to the growth medium during the process of differentiation. However, the endogenous expression of at least one cytokine, which induces the self-differentiation of DC progenitors into DCs is required for this process, i.e. self-differentiation does not take place if the iDC is not engineered to achieve expression of the at least one cytokine. The engineering of iDCs is, preferably, a process which is performed in vitro.

In a preferred embodiment, all cytokines and antigens required for the differentiation of a progenitor cell into a dendritic cell are endogenously expressed by the progenitor cell and the resulting iDC.

Any cell which can differentiate into a dendritic cell is a suitable progenitor for an iDC according to the present invention. Thus, the term "progenitor cell" encompasses pluripotent stem cells and hematopietic stem cells. Preferably, the progenitor cell to the dendritic cell is a monocyte, more preferably a peripheral blood monocyte. Preferably, said monocyte is characterized by presence of CD14 on its cell surface. Human monocytes that are $CD14^+CD16^-$ are considered classical monocytes, whereas $CD14^+CD16^-$ cells are non-classical monocytes. Both types of monocytes are preferred. Monocytes express receptors for: GM-CSF, M-CSF, G-CSF and chemokine receptors CCR1, CCR2 and CCR5. Therefore, a progenitor cell is defined by the expression of at least one gene selected from the group consisting of CD14, CD16, GM-CSF, M-CSF, G-CSF, CCR1, CCR2 and CCR5. More preferably, the progenitor cell is characterized by the expression of at least 2, 3 or 4 of the aforementioned genes. Moreover, the progenitor does, preferably, not express CD3, CD19, CD20 and CD56 as these are markers for T-lymphocytes, B-lymphocytes and natural killer cells. Expression of a receptor or surface marker can be determined by art known methods including the use of labelled antibodies that specifically bind to the receptor or surface marker and detection of the label. The label may be detected and/or quantified by various art known methods including confocal microscopy or fluorescent activated cell sorting (FACS).

The progenitor cell to the iDC is, preferably, derived from an organism selected from the group consisting of primate, rodent, cat, dog, pig, cow and sheep. The primate is, preferably, a human, a chimpanzee or a macaque, most preferably a human. The rodent is, preferably, a mouse or rat, most preferably a mouse.

In an especially preferred embodiment, the iDCs are derived from the donor or donors of the hematopoietic stem cells.

Preferably, a suitable progenitor cell is derived from bone marrow or from blood (peripheral or umbilical cord blood) by selecting cells which express CD14 on their surface.

The term "engineering" is used to refer to a process, which leads to the expression of one or more cytokines and/or one or more antigens, which are not naturally expressed by the DC progenitor or the DC or not naturally expressed at the level. In a preferred embodiment the cell is engineered by the introduction of a vector comprising nucleic acid sequences encoding the one or more cytokines and/or the one or more antigens. It is possible that these encoding nucleic acids sequences are comprised in one vector or on separate vectors, e.g. nucleic acid sequences encoding one or more cytokines are comprised on one vector and nucleic acid sequences encoding one or more antigens are comprised on another vector. In another preferred embodiment the DC progenitor or DC is engineered to express a cytokine and/or antigen, which is naturally encoded in the human genome but the expression of which is usually silenced or repressed in DC progenitors or DCs. This may be achieved by art known methods including the introduction of promoter and/or enhancer sequences in the vicinity of the gene encoding the respective cytokine and/or antigen. If promoters are introduced, it is preferred to introduce them upstream of the coding region of the respective gene in a way that these promoters direct the expression of the endogenous cytokine and/or antigen. Preferably, strong constitutive promoters are introduced like viral promoters, e.g. CMV immediate early promoter or SV40 promoter or promoters of housekeeping genes. In an alternative embodiment regulable promoter systems are used, which allow adaptation of the expression and of the expression level of the cytokine and/or antigen as required. Such regulatable promoter systems comprise, e.g. the $Tet^{on}$, $Tet^{off}$ or lac repressor system. Again different promoter systems may be used for the cytokines and the antigens, e.g. regulatable promoter for the cytokines and constitutive promoter for the antigen. The approach of using a vector can be combined with the approach of introducing a heterologous promoter/enhancer, e.g. the cell can be engineered to express one or more cytokines which are encoded in the human genome by introduction of a suitable promoter/enhancer into the vicinity of the respective cytokine gene and can be transfected with a vector comprising a nucleic acid sequence encoding one or more antigens.

The term "endogenous expression" of an antigen or a cytokine refers to production of said molecules by the dendritic cell itself and/or its progenitor cell. Said endogenous expression is either mediated by up-regulation of a cellular gene encoding said cytokine or antigen or by recombinant expression of the cytokine or antigen as outlined above.

Up-regulation of a cellular gene is, preferably, achieved by transcriptional activation of a cellular gene under the control of a tissue-specific, inducible or constitutive promoter. It is also preferred to transfect the cell with a nucleic acid that can activate transcription of a specific gene or a nucleic acid encoding a regulatory protein, such as a transcription factor which—if it is expressed in the cell—induces transcription of the endogenous cytokine gene. However, it is generally easier—and therefore preferred—to use recombinant expression the cytokine or antigen.

The term "recombinant expression" refers to the expression of a gene in the dendritic cell or its progenitor cell, wherein the gene is comprised by a nucleic acid molecule introduced into the cell. Methods for introducing foreign nucleic acid molecules into eukaryotic cells are well known in the art. In principle, any such method can be used as long as it results in the desired expression of the at least one cytokine and the at least one antigen by the cell without impairing the development or function of the dendritic cell.

Thus, in a preferred embodiment of the present invention the engineering of the iDC to induce expression of at least one cytokine which induces the self-differentiation of human dendritic cell (DC) progenitor cells into DCs and at least one antigen is the introduction of a vector encoding said proteins into the DC or its progenitor cell.

Vectors

Preferably the genes encoding the cytokine and the antigens are introduced using an expression vector for use in mammalian cells. Such vectors ordinarily include an origin of replication (as necessary, see below), a promoter located in front of the gene to be expressed, optionally an enhancer in trans, along with any necessary ribosome binding sites, RNA splice sites, polyadenylation site, and transcriptional terminator sequences. Such an expression vector may then be used to mediate expression of the at least one antigen and the at least one cytokine In a preferred embodiment the expression vector of the present invention comprises, essentially consists or consists of plasmids; phagemids; phages; cosmids; artificial chromosomes, in particular artificial mammalian chromosomes; knock-out or knock-in constructs; viruses, in particular adenovirus, vaccinia virus, attenuated vaccinia virus, canary pox virus, herpes virus, in particular Herpes simplex virus, retrovirus, adeno-associated-virus, rhinovirus, filovirus, and engineered versions of above mentioned viruses; virosomes; "naked" DNA, liposomes; virus-like particles; and nucleic acid coated particles, in particular gold spheres. The retrovirus is, preferably, a lentivirus.

Examples of plasmids, which allow the generation of such recombinant viral vectors include pFastBac1 (Invitrogen Corp., Carlsbad Calif.), pDCCMV (Wiznerowicz et al., "Double-copy bicistronic retroviral vector platform for gene therapy and tissue engineering: application to melanoma vaccine development." GeneTher. 1997 Oct.; 4(10):1061-8) and pShuttle-CMV (Q-biogene, Carlsbad, Calif.). Particularly preferred are viral vectors like lentiviral vectors (LV), retroviral vectors, adenoviral vectors.

LV offer an approach by which efficient, long lasting, non-toxic, and non-immunogenic gene delivery into monocytes and DC may be obtained. Lentiviruses can infect non-proliferating cells, due to the karyophilic properties of the lentiviral pre-integration complex, which allows recognition by the cell nuclear import machinery. LV can transduce primary quiescent cells, cells that are growth-arrested in culture, as well as terminally differentiated cells. The lentiviral packaging system was originally developed by Naldini et al. following a tripartite transient transfection procedure Naldini L et al. "In vivo gene delivery and stable transduction of nondividing cells by a lentiviral vector". *Science.* Apr. 12 1996; 272(5259):263-267) and later evolved into the "second generation" LV, where the four accessory genes of HIV (vif, vpr, vpu and nef) were deleted from the viral packaging system without affecting viral titers or transduction efficiency (Dull T et al. "A third-generation lentivirus vector with a conditional packaging system". *J Virol.* 1998; 72(11):8463-8471). The only remaining auxiliary gene in this system is therefore rev, which, along with the Rev response element (RRE), as its cognate binding sequence, is required for efficient export of the vector and packaging construct RNAs from the nucleus during virus production. Thus both toxicity as well as the likelihood of recombination are reduced in the "second-generation" LV. In parallel with improvements in the packaging system, has been the development of self-inactivating (SIN) LV designs which generally contain a 400 nucleotide deletion in the 3+ long terminal repeat (LTR) (Zufferey R et al. "Self-inactivating lentivirus vector for safe and efficient in vivo gene delivery". *J Virol.* December 1998; 72(12):9873-9880). The risk of vector mobilization with the wild type virus and subsequent production of replication competent LV is drastically reduced for the SIN vectors. The self-inactivating vectors with a tat-independent promoter have been termed "third generation" LV. In most cases, LV are pseudotyped (i.e., encoated with a heterologous envelope protein) with vesicular stomatitis virus glycoprotein (VSV-G), which is a rhabdovirus envelope protein that is reported to bind to ubiquitous cell surface phospholipids, thereby achieving a wide host range.

Thus, in a preferred embodiment of the present invention the lentiviral vector is a first generation LV, a second generation LV or a third generation LV. In an especially preferred embodiment, the LV is a third generation, i.e. self-inactivating, LV as this type of LV has a superior safety profile. The LV is, preferably pseudotyped with natural envelopes originated from other viruses or pseudotyped with engineered envelopes containing molecules to target the infection of specific cells. The use of a vector targeting infection of specific cells increases the safety avoiding the infection of off-target cells (non DCs or non DC precursors) and, therefore, especially preferred.

An especially preferred integrase-defective lentiviral vector has a mutated integrase with a nucleic acid sequence as defined by SEQ ID NO: 1.

The use of integrase-defective lentiviral vectors increases the safety of the iDC because integration events may cause insertional mutagenesis with consequences which are difficult to assess. Surprisingly, it has been found in the study underlying the present invention that integrase-defective vectors still allow for a stable and enduring expression of the antigen and the cytokine in differentiated DC even though the vectors may get lost during cell division and are unable to replicate on their own.

In cases where an adenovirus is used as an expression vector, the coding sequences may be ligated to an adenovirus transcription/translation control complex, e.g., the late promoter and tripartite leader sequence. The genes of interest may be inserted in the genome of an adenovirus by in vitro or in vivo recombination. Insertion in a non-essential region of the viral genome (e.g., region E1, E3, or E4) will result in a recombinant virus that is viable and capable of expressing the respective hypercytokine in infected cells. It is preferred that the viral vector used is modified to be replication incompetent.

To allow stable expression of a transgene the expression vector either has to be provided with an origin of replication, which allows replication independent from the genome of the cell, or has to be integrated into the genome of the first and/or second cells or it can be maintained stable as an episome in the nucleus of non-replicating cells. In the first case the expression vector is maintained episomally. Suitable origins of replication may be derived from SV40 or other viral (e. g., Polyoma, Adeno, CMV, VSV, BPV) source. In the second case, if the expression vector is integrated into the genome, e.g. a chromosome, it is not required to provide an origin of replication. In the later case, the episome corresponds to the pre-integration complex containing the double-stranded DNA copy of a retrovirus, lentivirus or more specifically HIV. Thus, it has been surprisingly found in the study underlying the present invention that integrase-defective lentiviral vectors which do neither replicate episomally nor integrate into the genome of the iDC are suitable for inducing self-differentiation of the iDC and maintaining their viability for several weeks and for supporting the regeneration of the immune system in an immunodeficient host following transplantation of HSC. Therefore, replication-incompetent vectors which do not integrate into the genome of the host cell are especially preferred.

To direct expression of the at least one cytokine and the at least one antigen, the genes encoding them are operationally linked to an internal promoter and/or enhancer that is recognized by the transcriptional machinery of the cell. Suitable promoters may be derived from the genome of mammalian cells (e.g., MHCII promoter, EF1alpha promoter) or from mammalian viruses (e.g., the cytomegalovirus promoter, the spleen focus-forming virus SFFV promoter). Especially preferred are promoters which enable the expression of the above-mentioned genes in dendritic cells or their progenitor cells.

In principle, every promoter which is transcriptionally active in antigen presenting cells can be used for the construction of lentiviral vectors which enable expression of antigens and cytokines in iDC or their progenitor cells. Thus, the promoter is, preferably, selected from the group consisting of costimulatory ligands (B7.1/CD80, B7.2/CD86, CD70), DC maturation markers (CD83) and DC markers (CD1c/BDCA-1, CD141/BDCA-3, CD209, CD40).

Mouse bone marrow progenitors transduced with LV expressing GM-CSF and IL-4 driven by the constitutive early cytomegalovirus (CMV) promoter or by the antigen-presenting cell restricted major histocompatibility complex class II (MHCII) promoter effectively induced DC self-differentiation in vitro and in vivo (Pincha et al, 2011) (Pincha M et al. Lentiviral vectors for induction of self-differentiation and conditional ablation of dendritic cells. *Gene Ther.* 2011, August; 18(8):750-764). Therefore, these two promoters are especially preferred.

Moreover, the use of other commonly used constitutive promoters (SV40, UBC, EF1α, PGK and CAGG) is preferred for the LV design for production of human iDC. Promoters that can be induced, for example, with doxycicline or tamoxifen can also be used.

The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the HindIII site toward the BglII site located in the viral origin of replication.

As used herein, "operatively linked" means incorporated into a genetic construct so that expression control sequences effectively control expression of a coding sequence of interest.

Specific initiation signals may also be required for efficient translation of coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic.

In order to allow co-expression of several cytokines and antigens in a single multicistronic RNA by mammalian cells, vector designs containing "2A" elements can be employed. The 2A-like sequences are highly conserved naturally occurring viral elements and are short polypeptide sequences (approximately 20 amino acid long) containing a consensus motif (2A, Asp-Val/Ile-Glu-X-Asn-Pro-Gly; 2B, Pro), resulting in cleavage between the 2A glycine and 2B proline. The cleavage is thought to occur by a ribosomal 'skipping' mechanism in which the 2A elements modify the ribosomal activity to skip a peptide bond formation between the glycine and the proline residues, resulting in the release of individual multiple protein products (Donnelly M L et al. "Analysis of the aphthovirus 2A/2B polyprotein 'cleavage' mechanism indicates not a proteolytic reaction, but a novel translational effect: a putative ribosomal 'skip'." *J Gen Virol.* May 2001; 82 (Pt 5):1013-1025). Recent studies have utilized the 2A-like cis-acting hydrolase elements (CHY-SEL) to create multicistronic vectors for simultaneous co-expression of multiple genes as individual proteins from a single open reading frame (ORF) transcript (Chinnasamy D et al. "Multicistronic lentiviral vectors containing the FMDV 2A cleavage factor demonstrate robust expression of encoded genes at limiting MOI". *Virol J.* 2006; 3:14; Szymczak A L, Vignali D A. "Development of 2A peptide-based strategies in the design of multicistronic vectors". *Expert Opin Biol Ther.* May 2005; 5(5):627-638). A particular advantage of the 2A system in construction of multicistronic vectors is the feasibility of using only a single promoter. Due to their small size, a single vector construct can utilize several 2A elements for expression of multiple proteins. 2A-like elements allow expression of multiple protein products at high efficiency of cleavage at equimolar ratios (de Felipe P. et al. "E unum pluribus: multiple proteins from a self-processing polyprotein". *Trends Biotechnol.* February 2006; 24(2):68-75). Heterologous 2A elements in the vector avoid homologous recombination, maintaining stability of the lentiviral vector. Different types of 2A-elements that can be used in the vector include: foot-and-mouth disease virus (F2A), equine rhinitis A virus (E2A), *Thosea asigna* virus (T2A) and porcine teschovirus-1 (P2A).

Alternatively, internal ribosome entry sites (IRES) can be used. Usually, in eukaryotes, translation can be initiated only at the 5' end of the mRNA molecule, since 5'-cap recognition is required for the assembly of the translation initiation complex. An IRES, is a nucleotide sequence that allows for translation initiation in the middle of a messenger RNA (mRNA) sequence by a process called internal translation initiation. Viral IRES are found for example in Picornavirus, hepatitis virus or poliovirus. Cellular IRES are found for example in the mRNAs encoding for fibroblast growth factor (FGF), platelet derived growth factor (PDGF), vascular endothelial growth factor (VEGF), insulin-like growth factor 2 (IGF-II), C-myc, L-myc, Pim-1, protein kinase, p58PITSLRE or p53. Similar to 2A elements, heterologous IRES can be combined in a vector for translation of one mRNA into several protein products.

Thus, in a vector encoding more than one polypeptide, e.g. an antigen and a cytokine, the nucleic acid sequence encoding the polypeptides are, preferably separated by a 2A element or an IRES. 2A elements which are especially preferred for use in the present invention are defined by SEQ ID NOs: 5 and 6.

The efficiency of expression may be enhanced by the inclusion of appropriate transcription enhancer elements and transcription terminators. In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

Inclusion of a suicide gene in the vector such as HSV-TK to allow pharmacologic ablation of iDC in vivo upon administration of pro-drugs such as Ganciclovir (Pincha M et al. Lentiviral vectors for induction of self-differentiation and conditional ablation of dendritic cells. *Gene Ther.* 2011, Aug.; 18(8):750-764) or, alternatively, use modified human caspase 9 fused to a human FK506 binding protein (FKBP) to allow conditional dimerization using a small molecule pharmaceutical (Strathoof et al, An inducible caspase 9 safety switch for T-cell therapy, Blood. 2005 Jun. 1; 105(11): 4247-4254) can be used to increase safety of the engineered iDCs in vivo. Therefore, in a preferred embodiment the vector additionally encodes a suicide gene. Said gene is, preferably, HSV-TK or modified human caspase 9 fused to a human FK506 binding protein.

Antigens

Preferably, the antigen expressed by the iDC is an antigen that can induce a cytotoxic or humoral immune response selected from the group consisting of xeno-reactivity, allo-reactivity, neo-reactivity or auto-immunity.

The term "xeno-reactivity" refers to the eliciting of an immune response against a protein expressed by an organism from another species, preferably a pathogen.

The term "allo-reactivity" refers to the eliciting of an immune response against a protein expressed by cells or tissues transplanted from a donor from the same species.

The term "neo-reactivity" refers to the eliciting of an immune response against a mutated protein of the subject receiving the iDCs. Preferably, neo-reactivity is directed at a cancer-antigen.

The term "auto-immunity" refers to the eliciting of an immune response against a protein expressed in the body of the organism from which the immune cells mediating said immune response are derived. Typically, auto-immunity is caused by the preclusion of mechanisms of immune tolerance. Preferably, auto-immunity is directed at a protein which is abnormally over-expressed by cancer cells without being mutated.

Especially preferred antigens inducing xeno-reactivity are selected from the group consisting of pp65 (derived from human cytomegalovirus), NS3 (derived from hepatitis C virus) and gag and env (derived from human immunodeficiency virus).

Especially preferred cancer-antigens, i.e. antigens eliciting neo-reactivity or auto-immunity, are selected from the group consisting of TRP2, MART1, WT1 and Tyrosinase (all derived from melanoma) and WT1, Her2/neu and BRCA1/2 (all derived from breast cancer).

Especially preferred is the use of pp65 as encoded by the nucleic acid represented by SEQ ID NO: 2. It is to be understood that the genetic code is degenerate so that different triplets encode the same amino. Hence, the invention also relates to all nucleic acid sequences encoding the same amino acid sequence as SEQ ID NO: 2. Since different triplets encoding the same amino acid are translated with different efficiency in different species, the optimization of the nucleic acid sequence by codon optimization is envisaged by the present application.

Especially preferred is the use of the experimental antigen chicken egg ovalbumin, also known as OVA, as full length protein or as immunogenic peptidic epitopes.

Moreover, at least one antigen encoded by the nucleic acid sequence comprised by the vector may be a variant of one of the aforementioned antigens which is immunologically identical to the antigen The term "variant" with respect to an antigen refers to proteins derived by deletion and/or substitution of at least 1, 2, 3, 4, 5, 8, 10, 15 or 20 amino acids from the antigen. Preferably, the variant has at least 80%, 85%, 90%, 95%, 96%, 97%, 98%, 99%, 99.5% 99.7%, 99.8% or 99.9% sequence identity to the antigen. Especially preferred are variants which are derived by C-terminal and/or N-terminal deletion of at least 1, 2, 3, 4, 5, 8, 10, 15 or 20 amino acids.

Moreover, the term "variant" refers to fragments of the above-described antigens which retain at least 5, 10, 15, 20, 25, 30, 40, 50, 60, 70, 80 or 90 amino acids of the full-length antigen.

It is preferred that all variants or fragments of the antigen are immunologically identical to the antigen. Two or more antigens are "immunologically identical" if they are recognized by the same antibody, T-cell or B-cell. The recognition of two or more immunogenic polypeptides by the same antibody, T-cell or B-cell is also known as "cross reactivity" of said antibody, T-cell or B-cell. Preferably, the recognition of two or more immunologically identical polypeptides by the same antibody, T-cell or B-cell is due to the presence of identical or similar epitopes in all polypeptides. Similar epitopes share enough structural and/or charge characteristics to be bound by the Fab region of the same antibody or B-cell receptor or by the V region of the same T-cell receptor. The binding characteristics of an antibody, T-cell receptor or B-cell receptor are, preferably, defined by the binding affinity of the receptor to the epitope in question. Two immunogenic polypeptides are "immunologically identical" as understood by the present application if the affinity constant of polypeptide with the lower affinity constant is at least 30%, at least 40%, at least 50%, at least 60%, at least 70%, at least 80%, at least 90%, at least 95% or at least 98% of the affinity constant of the polypeptide with the higher affinity constant. Methods for determining the binding affinity of a polypeptide to a receptor such as equilibrium dialysis or enzyme linked immunosorbent assay (ELISA) are well known in the art. Preferably, two or more "immunologicaly identical" polypeptides comprise at least on identical epitope.

Cytokines

The cytokine expressed by the iDC is any cytokine which is—on its own or in combination with one or more additional cytokines—able to induce the differentiation of progenitor cells into dendritic cells and/or stimulate T or B cells to develop, maintain viable or mount adaptive immune responses. Moreover, it is required that an iDC expressing the at least one cytokine and the at least one antigen is suitable for the methods and uses presented further below in the present application. Particularly, the DC must express all cytokines which support the regeneration of a functional immune system in an immunodeficient host after stem cell transplantation.

Preferably, the iDC expresses at least one cytokine selected from the group consisting of GM-CSF, IL-4, IFN-α, IL-15, TGF-B, TNF-α, FLT3L, IL-3 and CD40L.

More preferably, the iDC expresses a combination of cytokines selected from the group of combinations consisting of (i) FLT3L and IL-3; (ii) FLT3L and CD40L; (iii) FLT3L and IFN α; (iv) GM-CSF and IFN-α and IL-15; (v) GM-CSF and IFN-α and TNF-α; and (vi) GM-CSF and IFN-α and TGF-B.

Most preferably, the iDC expresses a combination of cytokines selected from the group of combinations consisting of (i) GM-CSF and IFN-α; (ii) GM-CSF and IL-4; and (iii) GM-CSF and IL-15.

A nucleic acid sequence GM-CSF is given in SEQ ID NO: 3 and a nucleic acid encoding IFNα is given in SEQ ID NO: 4. It is to be understood that the genetic code is degenerate so that different triplets encode the same amino. Hence, the invention also relates to all nucleic acid sequences encoding the same amino acid sequence as the amino acid sequences encoded by SEQ ID NOs: 3 and 4. Since different triplets encoding the same amino acid are translated with different efficiency in different species, the optimization of the nucleic acid sequence by codon optimization is envisaged by the present application.

Generation of iDCs

Moreover, the present invention relates to a method for generating iDCs comprising the steps of
a) isolating progenitor cells from a sample derived from a suitable donor;
b) engineering the cells to achieve expression of at least one cytokine which induces the self-differentiation of human DC progenitor cells into DCs and at least one antigen.

Preferably, the above-described method comprises the steps of
a) isolating progenitor cells from a sample derived from a suitable donor;
b) incubating the progenitor cells in a suitable medium in the presence of cytokines which enhance a gene transfer method and/or stimulate the development of the progenitor cells into dendritic cells.
c) transfecting or transducing the cells with at least one vector which is suitable for the expression of at least one cytokine which induces the self-differentiation of human DC progenitor cells into DCs and at least one antigen.

All the definitions given above, also apply to this embodiment.

A cytokine which enhances a gene transfer method is a cytokine which—when added to the growth medium before or during transfection—increases the efficiency of the uptake the foreign nucleic acid. Preferred for this purpose are GM-CSF, IL-4 or a combination thereof.

The iDCs generated by this method may be cultured until further use in a suitable medium. They may, however, also be stored frozen until they are administered to the patient. Methods for the cryopreservation of viable cells are known to the person skilled in the art.

In a preferred embodiment of the present invention, the progenitor cells are peripheral blood monocytes expressing CD14 derived from a human donor and the medium in method step a) is supplemented with GM-CSF and IL-4 or with GM-CSF and IFNα. This embodiment, preferably, involves use of integrase-defective lentiviral vectors for the expression of the aforementioned cytokines and at least one antigen are used in step c). Preferably, the antigen is pp65. This embodiment is described in greater detail in the examples section.

Therapeutic Uses of the iDCs of the Present Invention

Furthermore, the present invention relates to an iDC as described above for use as a medicament.

Moreover, the invention relates to an iDC as described above for use in the regeneration of the immune system of an immunodeficient subject following transplantation of hematopoietic stem cells (HSC).

Preferably, the subject is an organism selected from the group consisting of primate, rodent, cat, dog, pig, cow and sheep. The primate is, preferably, a human, a chimpanzee or a macaque, most preferably a human. The rodent is, preferably, a mouse or rat, most preferably a mouse.

The mouse belongs, preferably, to a strain selected from the group consisting of NOD-Rag1$^{null}$IL2Ry$^{null}$-NRG, NOD/LtSz-SCID/IL2Ry$^{null}$-NSG and NOD/SCID/IL2Ry$^{null}$-NOG. Older mouse strains that were used for generation of humanized mouse such as Balb/c-Rag1$^{null}$IL2Ry$^{null}$; NOD-SCID, NOD-SCID β2m$^{null}$ are also preferred. In addition, newer transgenic or knock-in mouse strains expressing human MHCI or MHCII or human cytokines critical for development of human cells in mice (such as GM-CSF, IL-3, IL-7, IL-15) could also be used.

In one especially preferred embodiment of the present invention, the mouse is characterized by:
(i) mutations in both alleles of the Prkdc-gene;
(ii) mutations in both alleles of the gene encoding IL2-receptor gamma chain; and
(iii) mutations in the gene encoding KITt receptor.

The mutations (i) and (ii) are, preferably, loss of function mutations, i.e. mutations that prevent the production of a gene product or cause the production of a non-functional gene product. The mutation (iii), preferably, results in a limited function of the KIT-receptor or is a conditional null-mutation which inhibits the formation of a gene product under defined conditions. Methods for generation conditional null-mutations are well known to the person skilled in the art.

Preferably, the mouse is a NOD mouse. More preferably, it carries the NOD Sirpa allele.

This mouse is also referred to as NSG mouse and is described in DE 10 2012 207 453 which is incorporated by reference as far as the mouse and its generation are concerned.

Immunodeficiency

The term "immunodeficiency" refers to any condition of the subject's immune system which is characterized by an impaired immune response as compared to an average individual of the same species which matches the subject with respect to age, sex and general living conditions such nutritional state. Said immunodeficiency is, preferably, caused by decreased numbers or an impaired function of at least one of the groups of immune cells defined below resulting in an increased susceptibility of the subject to infectious diseases caused by bacteria, viruses, fungi or other unicellular eukaryotes or increased susceptibility to malignancies.

In the art, it is differentiated between "immunocompromised" and "immunodeficient" patients, wherein the latter ones show a weaker immune response than the former ones. However, the term "immunodeficient" as used in the present application covers the whole spectrum of possible disturbances of the immune system from an increased frequency of mild infections to the almost complete lack of whole branches of the immune system as can be observed e.g. in X-linked severe combined immunodeficiency.

The immune system comprises two major branches, the adaptive immune system and the innate immune system.

The responses of the innate immune system against pathogens are not specific for a given pathogen. The innate immune system rather relies on pattern recognition receptors specific for molecular structures common to a large number of pathogens. Cells which mediate innate immune responses are mast cells, phagocytes (dendritic cells, macrophages and neutrophils) and natural killer cells.

The responses of the adaptive immune system are specific for a given antigen and, therefore, also restricted to this antigen. The cells of the adaptive immune system have antigen-receptors which are formed individually in each cell during its maturation in a random fashion. Thus, the adaptive immune system comprises a large pool of cells with many different receptors. If the subject encounters a pathogen, proliferation of those subpopulations of cells which carry a receptor specific for an antigen of the pathogen is induced. Later on, once the pathogen is eliminated from the body some of these cells form a population of memory cells, which allow for a more rapid build-up of an immune response if the pathogen is encountered again.

The adaptive immune response is mediated by T-lymphocytes and B-lymphocytes.

There are two major groups of T-lymphocytes: (i) T-helper cells, characterized by expression of the CD4-receptor on their surface, produce a variety of cytokines once their receptor binds a suitable antigen. This cytokines activate other cells of the immune system. Particularly, the microbicidal function of macrophages and the secretion of antibodies by B-lymphocytes is stimulated. (ii) Cytotoxic T cells (CTL), characterized by expression of the CD8-receptor on their surface, recognize and kill cells which are infected by viruses or other pathogens and recognize and kill tumor cells. CTL activation against an antigen presented by the major histocompatibility complex I (MHCI) is facilitated by T helper cells.

B-lymphocytes secrete antibodies which are specific for the antigen which is recognized by their receptor.

Depending on its cause, the immunodeficiency may be permanent or transient. A primary immunodeficiency results from inborn genetic aberrations is typically permanent. If the immunodeficiency is caused by ionizing radiation or a cytotoxic pharmaceutical, its duration depends on the dosage of the pharmaceutical or the radiation. If the dosage is sufficiently high to kill all hematopoietic stem cells in the subject, the immunodeficiency will be permanent. If only a part of the hematopoietic stem cells is killed, the immunodeficiency will resolve, once the remaining hematopoietic stem cells are able to repopulate the different hematopoietic lineages.

Preferably, the immunodeficiency of the subject is caused by is an immunodeficiency selected from the group consisting of immunodeficiency caused by ionizing radiation, immunodeficiency caused by the administration of at least one cytotoxic pharmaceutical, primary immunodeficiency and immunodeficiency caused by a pathogen. It is also envisaged that two or more of the aforementioned immunodeficiencies may be present in the subject.

An immunodeficiency caused by ionizing radiation may be caused by accidental or deliberate exposure to said radiation. Typically, deliberate exposure to ionizing radiation takes place as a treatment of cancer. Ionizing radiation predominantly kills those cells which are rapidly dividing. Thus, it is suited for the therapy of a variety of cancers as cancer cells are in many cases characterized by rapid proliferation. However, the cells of the immune system including the hematopoietic stem cells are also highly sensitive to ionizing radiation. Thus, they may be damaged in the course of radiotherapy of cancer. This damage may be an undesired side effect of organ- or tissue-specific irradiation of a solid cancer. However, especially in the case of leukemia which arises from the degeneration of stem cells of the immune system, a complete eradication of all hematopoietic stem cells is often the last option. In this case, transplantation of allogeneic hematopoietic stem cells after irradiation is required for the survival of the patient.

Typical types of ionizing radiation employed in the radiation therapy of cancer are X-rays, electron beams (energy range 4 to 20 MeV), particle radiation (protons, neutrons, ionized nuclei) and gamma radiation originating from sources such as cobalt-60, radium-226, caesium-137 or iridium-192.

A primary immunodeficiency is caused by genetic defect which impairs or completely inhibits the development of at least one type of immune cells in the subject.

Preferably, the primary immunodeficiency is selected from the group consisting of X-linked severe combined immunodeficiency (SCID), adenosine deaminase deficiency and IL-7Rα-chain deficiency. Preferably, X-linked SCID is caused by a mutation of IL-2RG.

It is to be understood that the immunodeficiency treated by the transplantation of hematopoietic stem cells may also be a primary immunodeficiency which is aggravated by ionizing radiation and/or the administration of at least one cytotoxic pharmaceutical.

Immunodeficiency caused by the administration of at least one cytotoxic pharmaceutical is also a typical effect of cancer therapy. Cytotoxic pharmaceuticals employed in cancer therapy frequently kill immune cells (including hematopoietic stem cells) in addition to cancer cells. With the dosages of cytotoxic pharmaceuticals usually employed, the immunodeficiency is, typically, transient as not all hematopietic stem cells in the patient are killed. Nevertheless, if hematopoietic stem cell transplantation is envisaged as a cure for this condition, the method of the present invention will be helpful.

In severe cases of certain cancers (e.g. Hodgkin's lymphoma) which do not respond to other types of treatment anymore a type of chemotherapy termed "high dosage chemotherapy" is employed. While the dosages of cytotoxic pharmaceuticals in other chemotherapy regimens are selected in order to minimize the resulting immunodeficiency, the complete destruction of the subject's immune system is a planned effect of high dosage chemotherapy. For this reason the subject receives an autologous or allogeneic hematopoietic stem cell transplant after completion of high dosage chemotherapy.

Typical cytotoxic pharmaceuticals include any inhibitors of topoisomerase I or II, such as camptothecin (topo I) or etoposide (topo II); any compound that interchelates DNA, such as doxorubicin. Particularly preferred are alkylating substances, anti-metabolites, antibiotics, epothilones, nuclear receptor agonists and antagonists, platinum compounds, interferons and inhibitors of cell cycle-dependent protein kinases (CDKs), inhibitors of cyclooxygenases and/or lipoxygenases, platinum coordination complexes, ethyleneimenes, methylmelamines, trazines, vinca alkaloids, pyrimidine analogs, purine analogs, alkylsulfonates, folic acid analogs, anthracendiones, substituted urea, methylhydrazin derivatives, in particular acediasulfone, aclarubicine, ambazone, aminoglutethimide, L-asparaginase, azathioprine, bleomycin, busulfan, calcium folinate, carboplatin, carpecitabine, carmustine, celecoxib, chlorambucil, cis-platin, cladribine, cyclophosphamide, cytarabine, dacarbazine, dactinomycin dapsone, daunorubicin, dibrompropamidine, diethylstilbestrole, docetaxel, doxorubicin, enediynes, epirubicin, epothilone B, epothilone D, estramucin phosphate, etoposide, flavopiridol, floxuridine, fludarabine, fluorouracil, fluoxymesterone, flutamide fosfestrol, furazolidone, gemcitabine, hexamethylmelamine, hydroxycarbamide, hydroxymethylnitrofurantoin, hydroxyprogesteronecaproat, hydroxyurea, idarubicin, idoxuridine, ifosfamide, irinotecan, leuprolide, lomustine, lurtotecan, mafenide sulfate olamide, mechlorethamine, megastrolacetate, melphalan, mepacrine, mercaptopurine, methotrexate, metronidazole, mitomycin C, mitopodozide, mitotane, mitoxantrone, mithramycin, nalidixic acid, nifuratel, nifuroxazide, nifuralazine, nifurtimox, nimustine, ninorazole, nitrofurantoin, nitrogen mustards, oleomucin, oxolinic acid, pentamidine, pentostatin, phenazopyridine, phthalylsulfathiazole, pipobroman, prednimustine, preussin, procarbazine, pyrimethamine, raltitrexed, rapamycin, rofecoxib, rosiglitazone, salazosulfapyridine, scriflavinium chloride, semustine streptozocine, sulfacarbamide, sulfacetamide, sulfachlopyridazine, sulfadiazine, sulfadicramide, sulfadimethoxine, sulfaethidole, sulfafurazole, sulfaguanidine, sulfaguanole, sulfamethizole, sulfamethoxazole, co-trimoxazole, sulfamethoxydiazine, sulfamethoxypyridazine, sulfamoxole, sulfanilamide, sulfaperin, sulfaphenazole, sulfathiazole, sulfisomidine, staurosporin, tamoxifen, taxol, teniposide, tertiposide, thioguanine, thiotepa, tinidazole, topotecan, triaziquone, treosulfan, trimethoprim, trofosfamide, UCN-01, vinblastine, vincristine, vindesine, vinblastine, vinorelbine, and zorubicin, or their respective derivatives or analogues thereof.

Immunodeficiency caused by pathogen is caused by infection of the subject with a virus or a bacterium. Said pathogen causes an immunodeficiency if it interacts directly with cell of the immune system, e.g. by using them as host cells, or by indirect means. Indirect means include the secretion of substances which modulate the activity of immune cells or the generation of mature immune cells from their progenitor cells. Moreover, a pathogen may induce secretion of such compounds by cells of the host organism. Immunodeficiency caused by a pathogen as referred to in this application is preferably caused by an infection with the human immunodeficiency virus (HIV).

Regeneration of the Immune System

The term "regenerating the immune system in an immunodeficient subject" relates to the improvement of the overall function of the immune system of an immunodeficient subject.

Preferably, the number and/or activity of at least one type of immune cells are increased. More, preferably, the activity of the adaptive or the innate immune system is increased. Also preferably, the activity and/or number of B-lymphocytes or T-lymphocytes are increased.

Even more preferably, the number of immune cells in and/or the activity of both branches of the immune system are increased.

Most preferably, as a result of the regeneration of the immune system, there are no significant differences between the function of the immune system of a healthy individual matched for age, sex and nutritional state and the subject whose immune system has been regenerated by transplantation of HSC and administration of the iDC of the present invention. Thus, most preferably, the regeneration of the immune system fully cures the immunodeficiency.

However, it is envisaged that the recipient of the transplanted HSC may be in need of immunosuppressive therapy in order to suppress a rejection of the transplanted HSC by the remainder of the host's immune system or to counter graft-versus-host disease. The necessity of such immunosuppressive therapy does not render the regeneration of the immune system less complete as this term as understood in this application only refers to the potential function of the immune system resulting from the transplanted HSC.

Transplantation of HSC

The term "transplanting hematopoietic stem cells" refers to the process of deriving material comprising hematopoietic stem cells (HSC) from one subject ("donor") and administering a preparation comprising HSC to the same or a different subject ("recipient").

In the simplest case, the material comprising HSC produced from the donor is administered to the recipient without further treatment steps. HSC preparations derived from peripheral blood, umbilical cord blood and bone marrow may be administered to the subject directly without enrichment or depletion of cell types comprised therein. In these cases, the preparation comprising HSC is identical to the material taken from the donor.

However, it is preferred to produce the preparation administered to the recipient by depleting T-lymphocytes from the material derived from the donor. This can be achieved by removing cells which are CD8-positive and/or CD3-positive from the material produced from the donor. It is also preferred that cells which are CD34-positive are enriched the preparation of HSC administered to the subject. If the HSC are derived from peripheral blood, it is preferred to enrich cells which are CD34-positive prior to administration to the subject. Means and methods for depletion or enrichment of cells carrying specific surface antigens are conventional in the art and, e.g. described in the examples section.

The HSC transplanted to the subject may be produced by every method known in the art. Typically, bone marrow of the donor has been the source of HSC for transplantation. In this method, the HSC are removed from a large bone of the donor.

However, production of stem cells from peripheral blood by apheresis has become the most common method. Before the HSC are produced, the donor receives granulocyte colony stimulating factor in order to increase the amount of HSC in peripheral blood. Apheresis is used to separate the white blood cells (including the HSC) from the whole blood. The white blood cells are stored for use in transplantation while plasma and erythrocytes returned to the donor's circulation.

A further source of HSC is umbilical cord blood. Umbilical cord blood is produced from the placenta and the umbilical cord after birth. Umbilical cord blood has a higher concentration of HSC than normally found in adult peripheral blood.

In the context of the present invention it is preferred that the stem cells are derived from one of the three aforementioned sources.

The transplantation of HSC is autologous or allogeneic.

In autologous stem cell transplantation donor and recipient of the HSC are identical, i.e. the HSC comprised by the preparation administered to the subject are derived from the same subject. Autologous transplantation of HSC is preferred if the immunodeficiency of the subject is caused by high dosage chemotherapy. In this case, material comprising HSC can be produced from the subject before the onset of high dosage chemotherapy and the preparation comprising HSC can be administered to the subject after completion of high dosage chemotherapy.

Allogeneic transplantation of HSC is involves the production of material comprising HSC from one or more subjects and the administration of a preparation comprising HSC of the first subject to a different subject. Thus, donor and recipient are not identical. A special case of allogeneic transplantation of HSC is xenogeneic transplantation of HSC. In this case, donor and recipient of the HSC belong to different species. Allogeneic transplantation of HSC is performed experimentally, for example, to model the human immune system in humanized mice.

Heterologous transplantation of HSC is, typically, performed if the subject suffers from leukemia, myeloma, severe combined immunodeficiency, aplastic anemia or congenital neutropenia. In these cases, a donor is selected who shares as many immunological properties with the recipient as possible. Especially important are identical HLA-A, HLA-B, HLA-C, HLA-DR and HLA-DQB1 genes. Thus, in one preferred embodiment of the present invention, the transplantation of HSC is allogeneic transplantation, wherein the donor and recipient are human.

One significant risk associated with the transplantation of hematopoietic stem cells is graft-versus-host disease (GVHD). This condition is characterized by a reaction of the transplanted immune cells against tissue of the recipient. There are two subtypes of GVHD, acute and chronic GVHD.

Acute GVHD occurs during the first 3 months after transplantation, while chronic GVHD has a later onset. Both types differ by the types of immune cells involved and by the cytokine pattern. Typically, acute GVHD is more severe than chronic GVDH. Acute GVHD may necessitate powerful medication which suppresses the immune system. As a consequence, many patients suffering from acute GVHD and treated for it develop life-threatening infections.

GVHD affects several tissues and organs: skin, mucosa, gastrointestinal tract, liver and lung. Chronic GVHD may additionally damage exocrine glands and connective tissue. GVHD can be mild (grade 1), moderate (grade 2) or severe (grades 3 and 4), depending on the number and extent of organ involvement. Patients with grade 1 GVHD normally requires no treatment, while the other grades require pharmacologic immunosupression.

The risk of GVHD increases with the number of mismatches of human leukocyte antigens (HLA) between donor and recipient. For this reason, the HLA type of donors and recipients of HSC transplants has to be carefully matched. Unfortunately, the high variability of human HLA molecules and the need for a good match make the search for a suitable donor for a given recipient quite difficult. In some cases, as suitable donor cannot be found before the disease to be treated by HSC transplantation progresses beyond curability.

The best donor is an individual having the same human leukocyte antigens (HLA)-A, -B, -C and -DRB1 as the recipient. However, a mismatch at one of the aforementioned loci is tolerable, especially in patients not having low-risk disease. Low-risk disease is, preferably, chronic myelogenous leukaemia in the first chronic phase, myelodysplastic syndrome subtype refractory anaemia or acute leukaemia in first remission. If additional HLA loci are analysed, single mismatches of HLA-DQ, -DP, -DRB3, -DRB4 or -DRB5 are acceptable, while multiple mismatches at these secondary loci decrease survival rates (Spellman et al., 2012, "A perspective on the selection of unrelated donors and cord blood units for transplantation", Blood 120: 259-265).

Surprisingly, the mice used in the study underlying the present invention showed only mild (grade 1) signs of GVHD upon histological examination, although no clinical signs by macroscopic or clinical observation (weight, activity, quality of the fur). These results showed that, even though the transplantation of HSC was xenogeneic, i.e. the mismatch of HLA molecules between donor (human) and recipient (mouse) was immense (see example 4), no severe GVHD was observed. Apparently, the presence of the iDCs of the present invention increases the tolerance of transplanted immune cells for the tissue of the recipient.

Therefore, in another preferred embodiment of the present invention, the transplantation of HSC is allogeneic, wherein donor and recipient are human and have a lower HLA match than required by the methods of HSC transplantation known in the art.

Particularly, at least 2 or 3 mismatches of loci selected from the group consisting of HLA-A, HLA-B, HLA-C and HLA-DRB1 are acceptable. This group will also be referred to as "primary group" of HLA loci. More preferably, 2 or 3 mismatches within the aforementioned group are acceptable. Most preferably 2 mismatches of the aforementioned HLA loci are acceptable.

With regard to the group consisting of HLA-DQ, HLA-DP, HLA-DRB3, HLA-DRB4 and HLA-DRB5 at least 2, at least 3, at least 4 or at least 4 mismatches are, preferably, acceptable.

This group will be referred to as "secondary group" of HLA loci. More preferably, 2 or three mismatches are acceptable. And, most preferably, 2 mismatches are acceptable.

In an especially preferred embodiments of the invention, at least 2 mismatches of loci selected from the primary group and at least 2 mismatches of loci selected from the secondary group are acceptable.

In yet another especially preferred embodiments of the invention, at least 2 mismatches of loci selected from the primary group and at least 3 mismatches of loci selected from the secondary group are acceptable.

In yet another especially preferred embodiments of the invention, at least 2 mismatches of loci selected from the primary group and at least 4 mismatches of loci selected from the secondary group are acceptable.

In another especially preferred embodiments of the invention, at least 3 mismatches of loci selected from the primary group and at least 2 mismatches of loci selected from the secondary group are acceptable.

In yet another especially preferred embodiments of the invention, at least 3 mismatches of loci selected from the primary group and at least 3 mismatches of loci selected from the secondary group are acceptable.

In yet another especially preferred embodiments of the invention, at least 3 mismatches of loci selected from the primary group and at least 4 mismatches of loci selected from the secondary group are acceptable.

In another preferred embodiment, the transplantation of HSC is xenogeneic, wherein the donor is a human and the recipient is a rodent, preferably a mouse having a primary immunodeficiency, most preferably severe combined immune deficiencies SCID such as X-linked SCID (with mutations in IL-2RG) or in enzymes derived from the recombination activating genes (RAG-1 and RAG-2).

In a preferred embodiment of xenogeneic HSC transplantation, the recipient is the NRG mouse described above in this application and the donor of the HSC is a primate, more preferably a human.

Moreover, the present invention relates to an iDC as described above for enabling the endogenous regeneration of Regulatory T cells (Tregs) after stem cell transplantation. Tregs, formerly known as suppressor T cells, are a subpopulation of T cells which modulate the immune system, maintain tolerance to self antigens and abrogate autoimmune disease. Mouse models have suggested that modulation of Tregs can treat autoimmune diseases facilitate organ transplantation. Mouse studies have revealed efficiency of therapeutic vaccination with in vitro generated and manipulated tolerogenic DC in inhibition of experimental autoimmunity. Adoptive transfer of donor-derived CD4(+)CD25(+)FOXP3(+) regulatory T cells (Treg) protected mice from graft-versus-host disease in mismatched bone marrow transplantation models. Results from first clinical trials in humans exploring similar strategies have been documented by some groups and seem to confirm the efficacy of Tregs for the prevention of severe complication, such as graft-versus-host disease, after allogeneic stem cell transplantation. In humans, Tregs can be defined immunophenotypically as $CD4^+/CD127^-CD25^{hi}$ or $CD4^+/CD127^-CD25^{hi}FOXP3^+$ cells. Thus, the iDCs of the present invention may be used for treating graft-versus-host disease experienced by the recipient of an HSC transplant.

Moreover, the present invention relates to an iDC as described above for use as a medicament for the treatment of cancer which spreads lymphatically or a disease caused by a lymphotrophic pathogen.

The iDC of the invention migrate preferentially through the lymphatic vessels to the lymph nodes. For this reason, they are especially suited for the treatment of diseases which involve the lymph nodes.

One hallmark of cancer is its ability to spread systemically throughout the body resulting in the formation of metastases. Once metastases are present, surgical resection or irradiation of the primary tumor are not sufficient to cure the disease. If there are few metastases, surgery and/or radiotherapy may be used to remove said metastases. However, in most cases, the number of metastases is too disseminated to allow for a removal by the aforementioned means. At that point of a cancer disease, systemic therapy such as chemotherapy is the only means of treatment left which maintains the chance of a cure. However, in many cases chemotherapy fails to kill all cancer cells or the cancer acquires resistance against the drug. Therefore, it is of pivotal importance to prevent the systemic spread of cancer cells.

Two major routes exist for the systemic spread of cancer: the circulatory system and the lymphatic system. In the latter case cells of the tumor migrate into the lymphatic vessels draining the area, where the tumor is located. The cells than migrate to the regional lymph nodes. These lymph nodes are also known as "sentinel lymph nodes". The analysis of lymph nodes draining a specific area is routine part of the surgical resection of a tumor and the presence or absence of cancer cells in the sentinel lymph nodes is an important parameter for the staging of the disease and the selection of the appropriate treatment. The presence of cancer cells in the sentinel lymph nodes is associated with a bad prognosis.

The iDC of the present invention have the potential to mediate the killing of cancer cells which are present in the lymph nodes, thus blocking further lymphatic spread of the disease. For this use of the iDC it is preferred that they express an antigen presented by the cancer cells in question.

Preferred cancers that are treated according to the invention are selected from the group consisting of melanoma and breast cancer, hematologic malignancies (leukemia, lymphoma), neurologic malignancies (glioma, glioblastoma), prostate cancer, lung cancer, colon cancer and liver cancer. The treatment of melanoma and breast cancer is especially preferred.

Preferably, an iDC for the treatment of cancer which spreads lymphatically expresses at least one antigen which is selected from the group consisting of TRP2, MART1, WT1 and Tyrosinase (all derived from melanoma) and WT1, Her2/neu and BRCA1/2 (all derived from breast cancer).

There are pathogens which are primarily or even exclusively found in the lymphatic system. For the use in the therapy of such a disease, the iDC, preferably, expresses at least one antigen also expressed by the respective pathogen.

The pathogen is, preferably, selected from the group consisting of viruses, bacteria, fungi and unicellular eukaryotes. More preferably, it is a virus, most preferably HIV. Preferably, iDC for use in the treatment of HIV express the antigens gag and env.

Method for Regenerating an Immune System

Furthermore, the present invention relates to a method for regenerating an immune system in an immunodeficient subject comprising the steps of
a) transplanting hematopoietic stem cells to the subject; and
b) administering to the subject an iDC engineered to express at least one antigen and at least one cytokine which induces the self-differentiation of human DC progenitor cells into DCs.

All definitions given above for the iDCs and their therapeutic uses also apply to this embodiment.

The above-described method is, preferably, used to generate mice with a humanized immune system. Therefore, the subject is, preferably, a mouse. More preferably, the mouse belongs to a strain selected from the group consisting of NOD-Rag1$^{null}$IL2Rγ$^{null}$-NRG, NOD/LtSz-SCID/IL2Rγ$^{null}$-NSG and NOD/SCID/IL2Rγ$^{null}$-NOG.

Preferably, the HSC are derived from a human and the antigen is pp65. Moreover, it is preferred that the iDC express the antigen pp65 and the cytokines (i) GM-CSF and (ii) interferon-α or interleukin-4 or interleukin-15. More preferably, this expression is mediated by a vector and, most preferably, it is mediated by an integrase-defective lentiviral vector.

The mice generated by this embodiment have humanized immune system which has an improved function as compared to mice that did not receive the iDC of the present invention before or after transplantation of HSC.

This type of xenogeneic HSC transplantation creates a human immune system in a rodent, preferably a mouse. Such an animal with a human immune system is a valuable tool for research which can be used for certain experiments which are—for ethical or logistic reasons—not possible in humans. Unfortunately, this animal model has some deficiencies. After transplantation of human HSC lymphatic tissue develops only poorly. Surprisingly, administration of human iDC of the present invention to mice after transplantation of human HSC lead to improved reconstitution of lymph nodes containing human T cells and DC in the treated mice, thus, making these mice a better model of the human immune system.

Currently available mouse models based on the humanized immune systems (HIS) show poor development of functional T cells, particularly functional cytotoxic T cells, capable of recognizing and lysing target cells presenting antigenic epitopes through the major histocompatibility complex (MHC). In contrast to this, mice with a human immune system generated according to the present invention show an increase in the frequency and an improved T-lymphocyte activity. In addition, mice with a human immune system generated according to the present invention showed an increase in the frequency of mature B cells correlated with the production of human immunoglobulins (such as IgM, IgG) and antigen-specific human antibodies. In addition, mice with a human immune system generated according to the present invention showed enhanced development of human T cells in the thymus and normal development of Tregs.

Therefore, another preferred embodiment of the present invention relates to a mouse with a humanized immune system generated by the method described above and the use of this mouse for the study of the human immune system or for the testing of drugs, implants or devices for their use in humans. A preferred use is the study of the human adaptive immune system with this mouse model.

Since it is not desirable that implants cause inflammation in the human body, the testing of implants in the humanized mouse model of the present invention is an especially preferred use.

BRIEF DESCRIPTION OF THE FIGURES

FIGS. 13A-13F: SmyleDC immunization augments the detection of human cytokines in plasma and expansion of human T cells. (A) Human cytokines were detected in plasma from control, ConvDC or SmyleDC-immunized HIS-mice (week 20 after HCT). Bars represent average of cytokine concentration (pg/mL) and error bars represent SEM. (B) Analyses of engraftment of human $CD45^+$, hematopoietic cells and subfractions relative to expression of (C) $CD3^+$, (D) $CD19^+$, (E) $CD4^+$ and (F) $CD8^+$ cells in peripheral blood of control, ConvDC or SmyleDC-immunized HIS-mice before prime/boost immunization (week 10), two weeks after immunization (week 13) and eight weeks after immunization (week 20). Data represents the distribution of control (n=10), ConvDC (n=7) and SmyleDC (n=22) immunized mice.

FIGS. 14A-14H: Regeneration of draining lymph nodes and lymphatic flow in HIS-NRG after SmyleDC immunization and characterization of human cells present in regenerated LN. (A) Macroscopic detection of inguinal and axillary LN eight weeks after the last SmyleDC immunization. Images were acquired with an Axiocam fluorescence microscope (Zeiss) at 10× of magnification and analyzed using Axiowert software (Zeiss). (B) Frequency of mice with regenerated LN at the same side of SmyleDC injection side (IS, black bars) or contralateral side (CL, empty bars), demonstrating both local and systemic lymphatic regeneration. (C) Averaged frequency of human $CD45^+$, $CD3^+$ and $CD19^+$ cells and (D) $CD4^+$ and $CD8^+$ T cells in LN (n=4) recovered from SmyleDC-immunized mice. (E, F) Characterization of $CD45RA^+/CD62L^+$ naïve, $CD45RA^-CD62L^+$ central memory and $CD45RA^-CD62L^-$ effector memory subpopulations in $CD4^+$ and $CD8^+$ LN T cells (n=4), respectively. (G) Frequency of follicular T helper cells (expressing $CD4^+CXCR5^{+hi}D-1^+ICOS^+$) in CD3 were analyzed in pooled LN (n=8) obtained from SmyleDC-injected HIS mice, confirming endogenous generation of human T cells in the mice. Human tonsil cells were used as positive control. (H) Relative frequencies of $CD24^{hi}CD38^{hi}$transitional, $IgD^+ CD24^{int}CD38^{int}$ mature and $CD27^{hi}CD38^{hi}$plasmablasts in $CD19^+$ cells from pooled humanized LN and human tonsil cells, showing endogenous generation of human B cells in the mice.

Bioluminescent signal spreading to the pre-formed regenerated LN (detectable by external imaging or by analyses of the explanted LN) demonstrated the migratory capacity of SmyleDC and the high viability of the cells in LN (up to 21 days).

Figure 16:
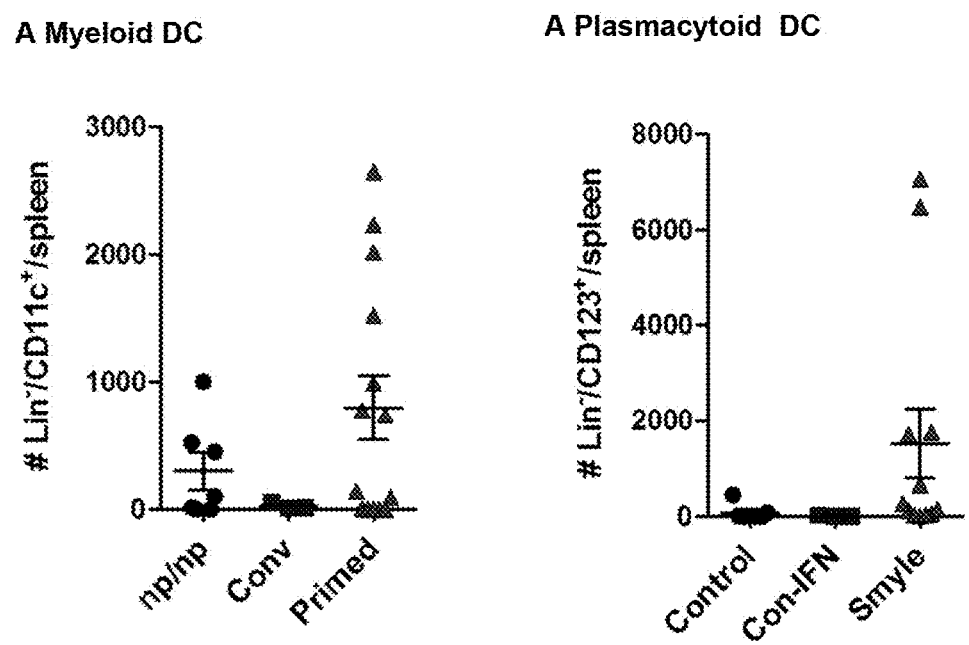

FIG. 16: Detection of human DCs in spleen of mice. Spleens were collected from NRG mice transplanted with human $CD34^+$ cells and immunized with SmyleDC or ConvDC (weeks 10, 11) or non-immunized controls and sacrificed on week 20. Splenocytes were analyzed by immunostaining and flow cytometry for the presence of myeloid DC ($Lin^-$, $HLA-DR^+$ $CD11c^+$) and plasmacytoid DC ($Lin^-$, $HLA-DR^+$ $CD123^+$). The data shows the endogenous generation of human dendritic cells in the mice.

FIGS. 17A-17E: Expansion of the absolute numbers of human cell populations in spleen or HIS-NRG mice SmyleDC. (A) Scatter plots representing total cell numbers of human $CD45^+$, $CD3^+$ and $CD19^+$ cells per spleens from control, ConvDC and SmyleDC-immunized mice on week 20 after HCT. Cell counts per spleen from total, $CD45RA^+/CD62L^+$ naïve and $CD45RA^-CD62L^-$ effector memory subpopulations in (B) $CD4^+$ and (C) $CD8^+$ T cells. (D) Total cell numbers of $CD3^+CD4^+CXCR5^{+hi}PD-1^+ICOS^+$ follicular T helper cells and (E) total cell counts of CD19+ $CD24^{hi}CD38^{hi}$transitional, $CD19^+IgD^+CD24^{int}CD38^{int}$ mature and $CD19^+CD27^{hi}CD38^{hi}$plasmablasts per spleens from control, ConvDC and SmyleDC-immunized mice. Bars and error bars represent means and SEM respectively. * represents p<0.05. The data demonstrates that SmyleDC expands quantitatively and potentially qualitatively (broader T cell receptor and B cell receptor repertoires) the pool of mature human T and B cells in HIS-NRG mice.

FIGS. 18A-18G: Human T cell and humoral responses against pp65 HIS-NRG after SmyleDC immunization. (A) Human $CD3^+$ cells were sorted from splenocytes from control (n=4), ConvDC and (n=4) SmyleDC-immunized (n=6) HIS-mice eight weeks after immunization. Following ex-vivo expansion for 10 days with SmyleDC, re-stimulation in the presence (pp65pp) or absence (NoAg) of CMV-pp65 overlapping pooled-peptides was performed overnight on anti-IFN-γ-coated plates. Bars represent average of IFN-γ positive spots for $2 \times 10^4$ cells. (B) Similar procedures were performed with effector cells recovered from LN obtained from SmyleDC-immunized HIS-NRG (n=4 mice), that were assayed in parallel with PBMNC obtained from a CMV seropositive human donor. Data represents averaged IFN-γ positive spots in $2 \times 10^4$ cells. (C) Frequency of cells expressing $CD27^+CD38^+IgG^+$ within human $CD19^+$ cells. (D) Quantification of total immunoglobulin (Ig) G and (E) IgM in plasma from control and DC-immunized mice eight weeks after immunization. (F) Quantification of pp65-specific IgG and (G) pp65-specific IgM in plasma from control, ConvDC and SmyleDC-injected mice 8 weeks after immunization. Plasma samples from systemic lupus erythematosus (SLE) patients were used as positive controls for both pp65-specific IgG and IgM. Bars and error bars represent means and SEM respectively. "nd" stands for not detected. * represents p<0.05. The data demonstrates functionally human adaptive antigen-specific T and B cell responses in the mice.

Figure 19A:
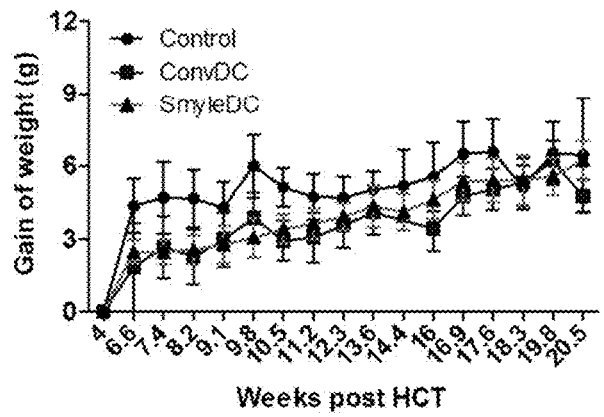
Figure 19B:
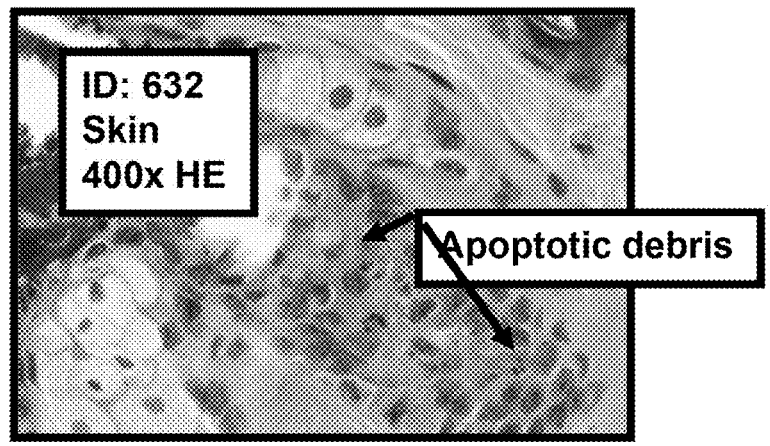
Figure 19C:
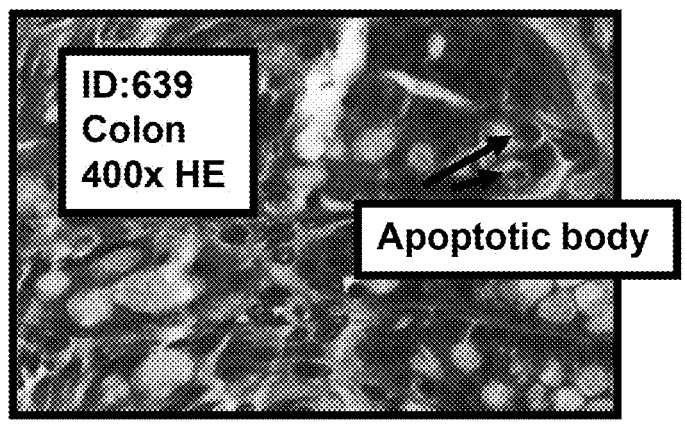

FIGS. 19A-19C: Monitoring Graft Versus Host Disease (GVHD) by weight and histological analyses. (A) 4 weeks-old NRG mice transplanted with human $CD34^+$ cells and immunized with SmyleDC or ConvDC (on weeks 10, 11) or non-immunized controls were monitored over time for gain of weight. No significant differences were observed. After sacrifice, skin and colon specimens were harvested and analyzed for signs of GVHD (B) and (C) Histological analyses (400× H&E staining) of skin and colon showed mild Grade 1 GVHD in 2 out of 4 and 3 out of 4 immunized with SmyleDC, respectively. Some apoptotic debris were detectable, but focal and sparse infiltrates of lymphocytes indicated no inflammation. This data demonstrates that despite the regeneration of a fully adaptive human xenograft immune system in the mice, no severe or moderate graft-versus-host disease was observed.

Figure 20A:
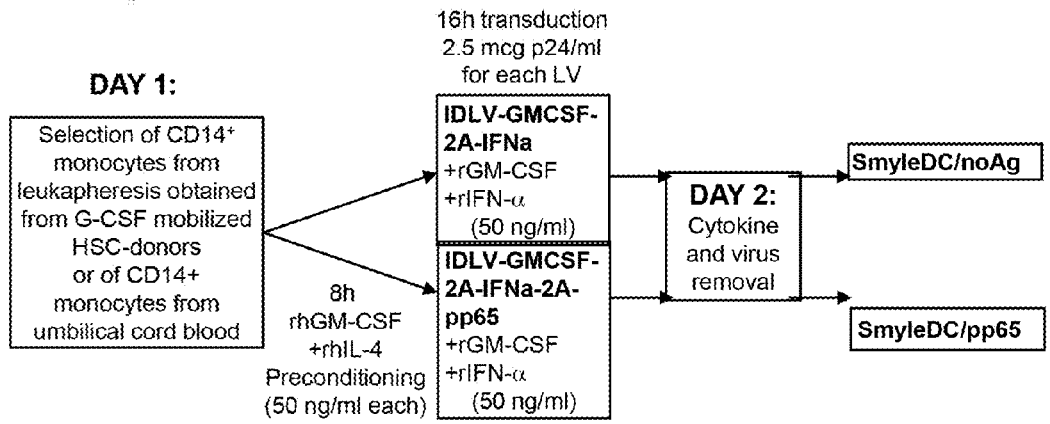
Figure 20B:
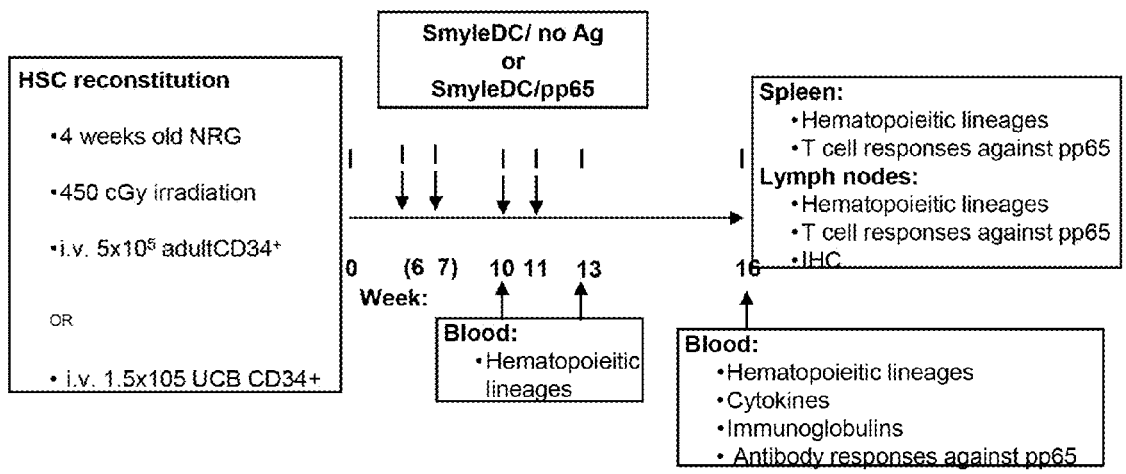
Figure 20C:
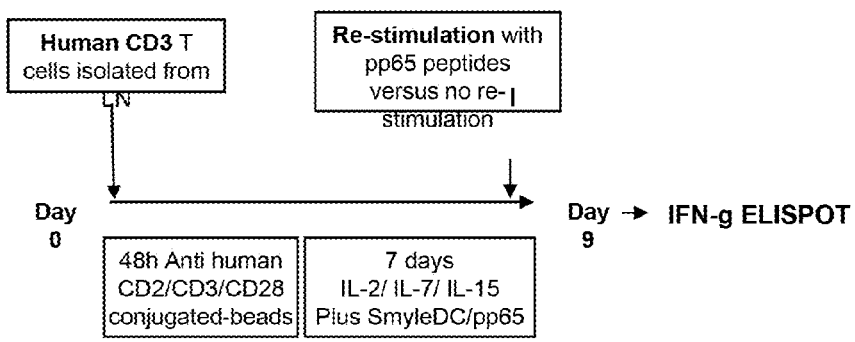

FIGS. 20A-20C: Experimental schemes for SmyleDC produced by transduction of monocytes with a bicistronic vector lacking antigen (IDLV-GMCSF-2A-IFNa) or for SmyleDC/pp65 produced by transduction of monocytes with a tricistronic vector co-expressing the pp65 antigen (IDLV-GMCSF-2A-IFNa-2A-pp65). (A) Scheme of SmyleDC/pp65 production. (B) Schedule of immunizations and analyses. (C) Analyses of human T cell responses generated in immunized mice.

FIGS. 21A-21F: Generation of SmyleDC and SmyleDC/pp65. a) Schematic representation of the bicistronic and tricistronic lentiviral vectors. b) Recovery of viable cells: Total viable SmyleDC (grey) and SmyleDC/pp65 (black) recovered on days 7, 14 and 21 as percentage relative to input of transduced monocytes on day 0. c) Stability of expression of DC surface antigens by FACS analyses of $CD86^+/HLA-DR^+$ cells on days 7, 14 and 21. d) Persistency of pp65 expression analyzed by intracellular staining of SmyleDC/pp65 on days 7, 14 and 21. e) Expression of relevant DC immunophenotypic markers (CD14, HLA-DR, HLA-ABC, CD80, CD86, CD83, CD11c and CD123) as percentage on day 7. f) Secreted cytokines detectable in SmyleDC and SmyleDC/pp65 supernatants on day 7 (IL-1β, IL-2, IL-4, IL-5, IL-6, IL-7, IL-8, IL-10, IL-12p70, IFN-γ, MCP-1, TNF-α) and transgenic cytokines (GM-CSF and IFN-α) using cytokine bead arrays. All analyses were performed as independent triplicates with monocytes obtained from three different donors. The data demonstrate that the co-expression of the full pp65 antigen did not alter the characteristics of the iDC.

Figure 22A:
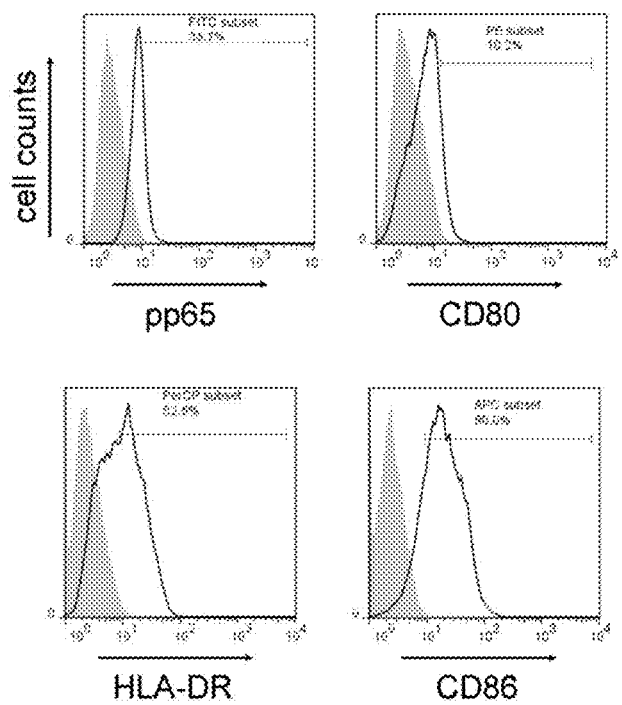
Figure 22B:
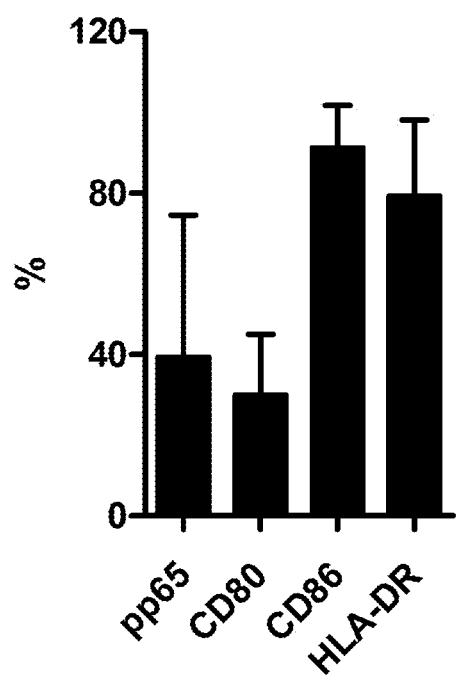
Figure 23A:
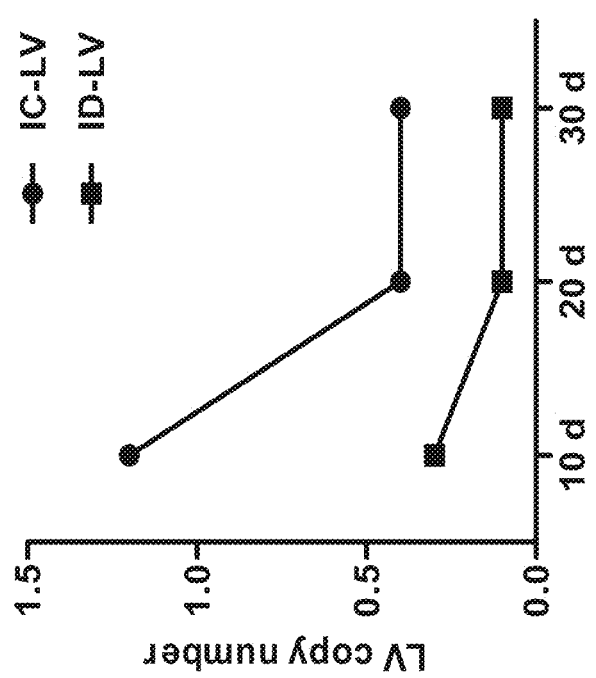
Figure 23B:
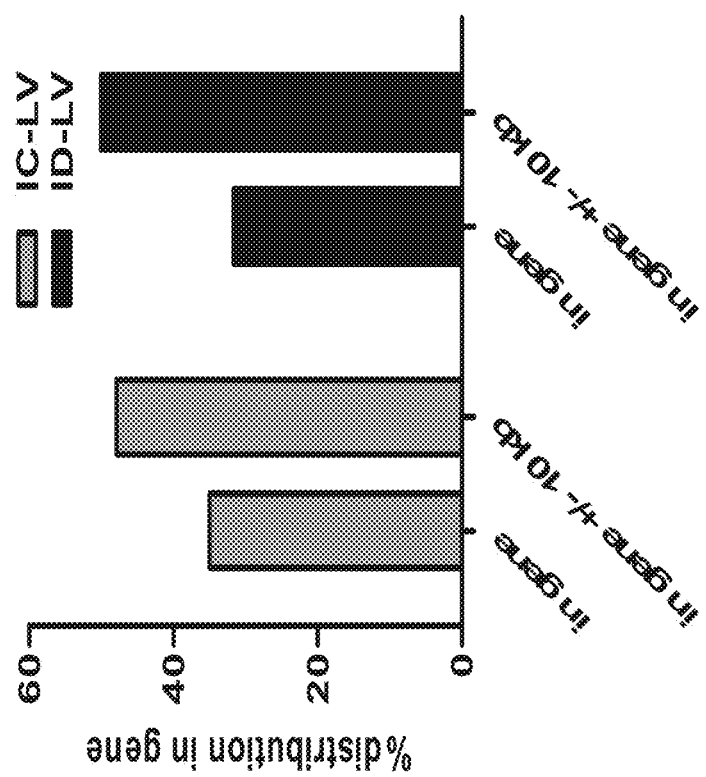
Figure 23C:
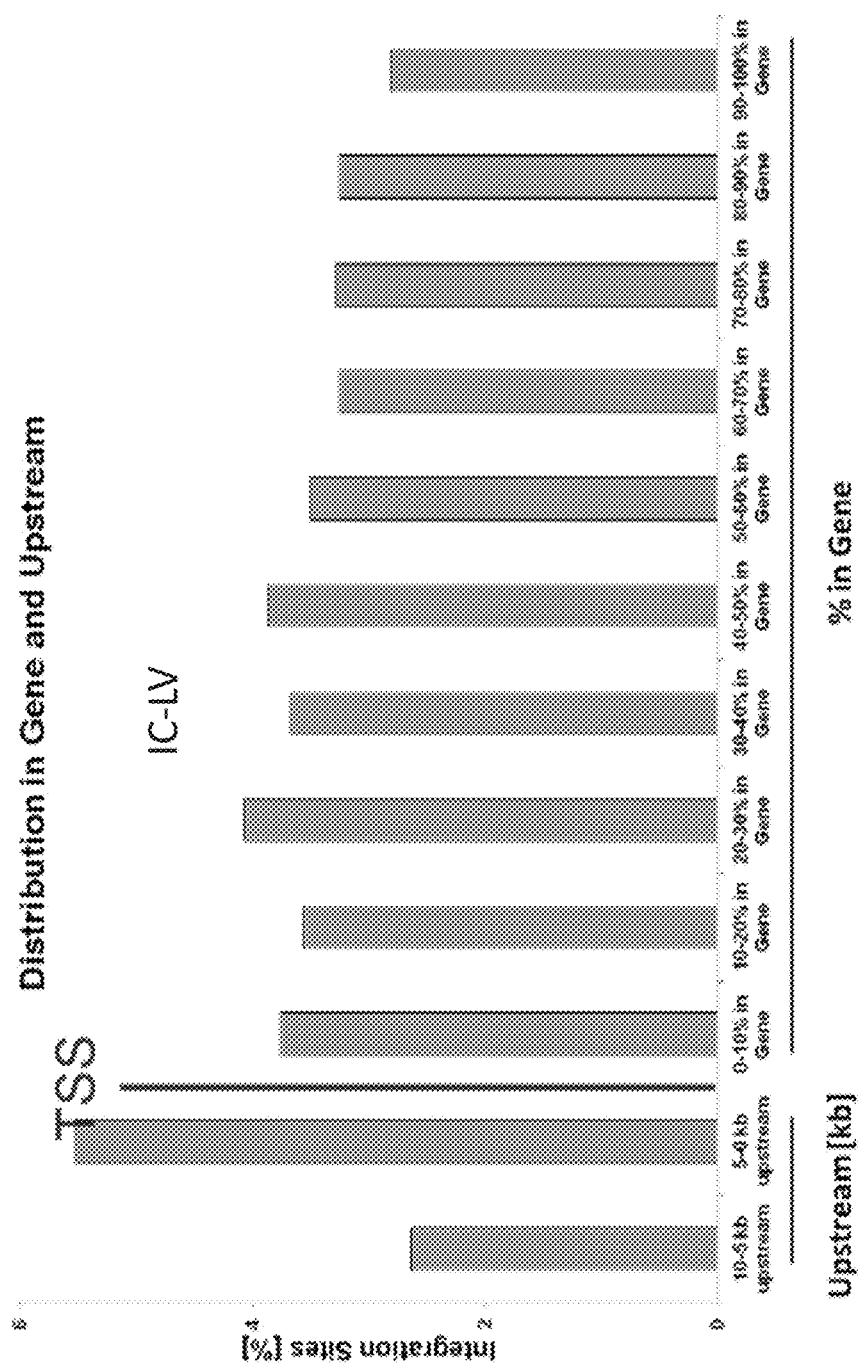
Figure 23C:
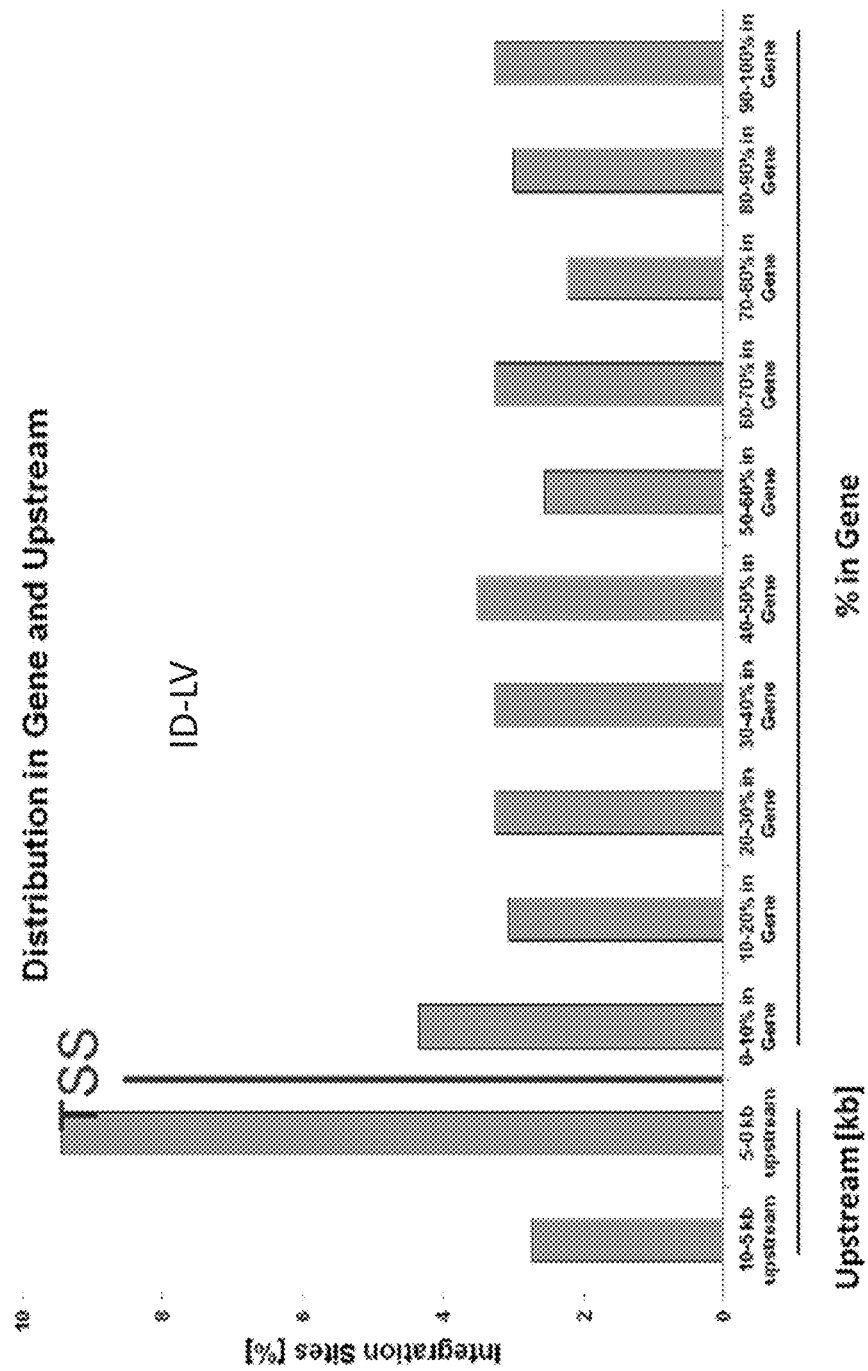
Figure 23D:
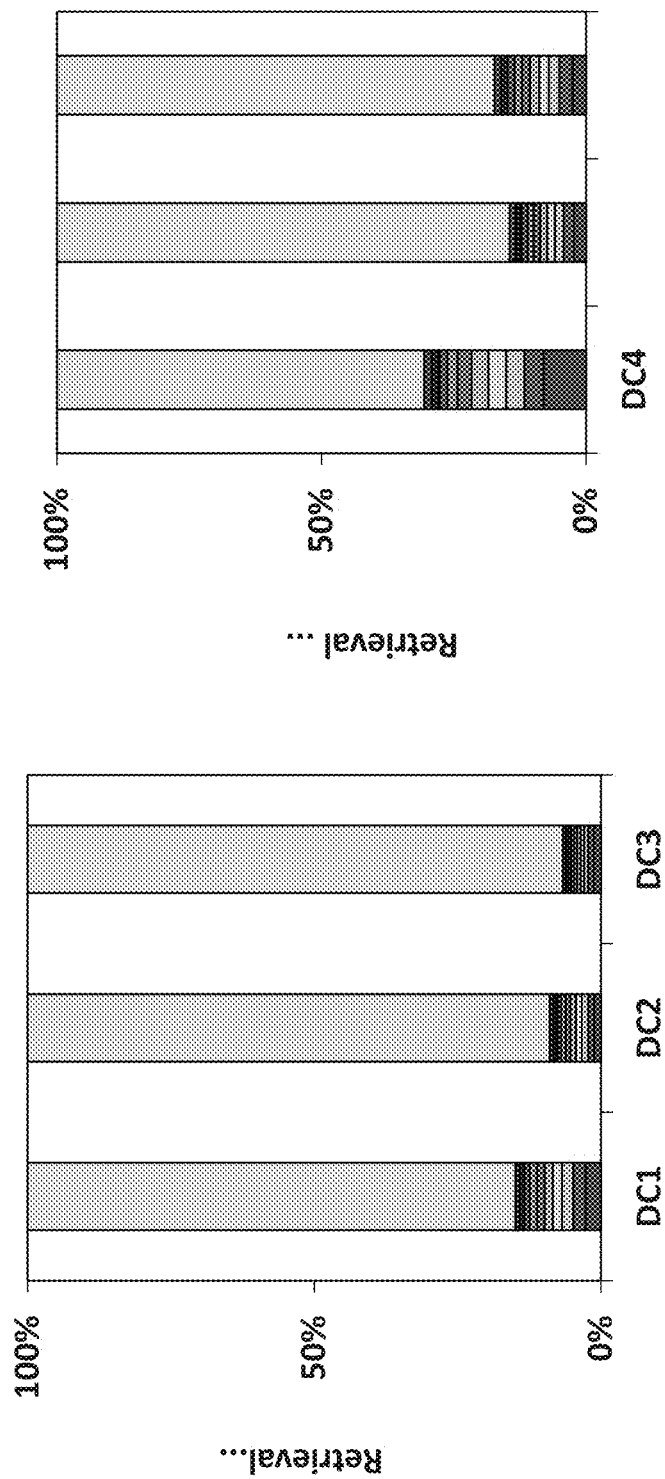

FIGS. 22A-22B: Generation of SmyleDC/pp65 with monocytes obtained from umbilical cord blood and immunophenotype analyses. (a) Representative examples of flow cytometry analyses performed with day 7 SmyleDC/pp65. (b) Frequency of immunophenotypic marker positive cells (n=4). The data demonstrate that production of SmyleDC from human cord blood material used for stem cell transplantation is feasible and reproducible.

FIGS. 23A-23D: Integration analysis of integrase competent (IC) and integrase defective (ID) lentiviral vector a) Number of integrated LV copies per cell for SmyleDC/pp65 generated with IC-LV or ID-LV, harvested on days 10, 20 and 30 and DNA analyzed by qPCR. b) LAM-PCR was used to analyze frequencies of integration site distributed +/−10 kb from genes. IC-LV (gray) and ID-LV (black). c) Frequency of integration sites relative to transcription start site (TSS), either upstream in gene reading frame. d) 10 dominant integration sites detectable in gene locus (grey boxes represent recurrent genes inter or intra analyses) and kinetic analyses depicting relative frequencies of insertions in each gene. The data demonstrate that fewer lentiviral integrations are observed for ID-LV and that the integration pattern does not indicate hot-spots for oncogenic development.

Figure 24A:
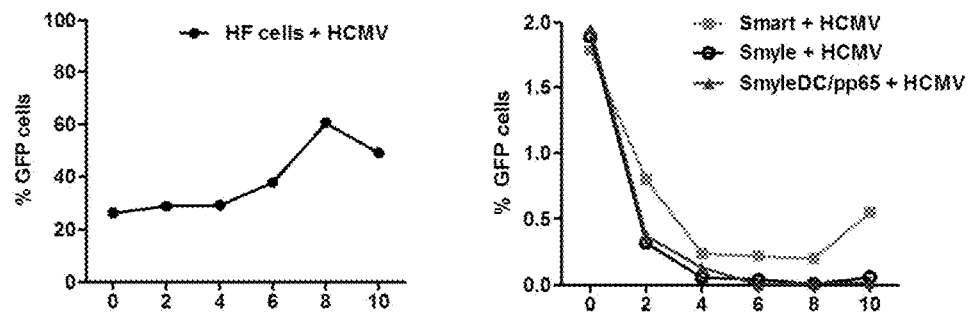
Figure 24B:
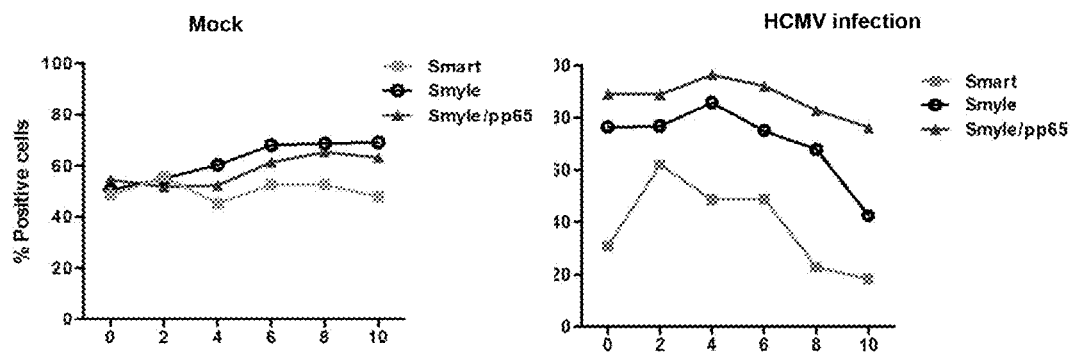
Figure 24C:
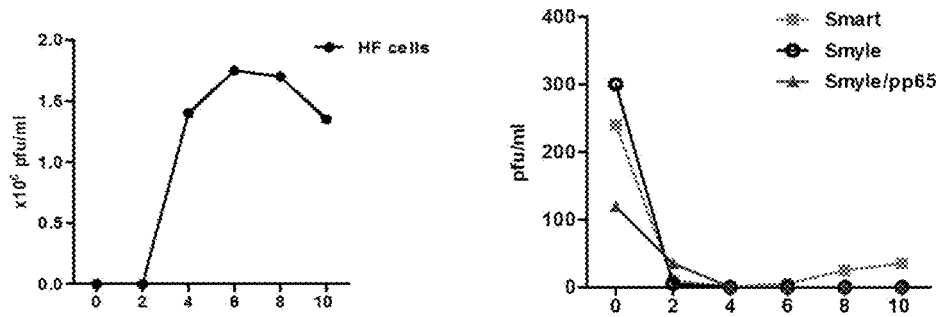

FIGS. 24A-24C: Infection of lentivirus-vectored DCs with HCMV. a) Flow cytometry analyses showing kinetics of HCMV infection (MOI=1) by GFP expression from 0-10 d.p.i. Human fibroblasts (HF) are positive controls and the comparison included iDC expressing GMCSF/IL4 (SmartDC), iDC expressing GMCSF/IFNa, (SmyleDC) or expressing GMCSF/IFNa/pp65 (SmyleDC/pp65). b) Flow cytometry analyses showing changes in CD80 expression at several d.p.i. after HCMV infection. Percentages represent analyses of CD80$^+$ cells comparing with uninfected cells (mock, left graph) and HCMV infected (right graph). c) Detection of HCMV virions released in the cell supernatants. Supernatants from each infected cell cultures were collected on day 0, 2, 4, 6, 8 and 10 and used to infect HF cells. The newly produced virus was determined by plaque forming assays. Numbers of plaque were determined on each time points and represented as pfu/ml. The data demonstrate that SmyleDC do not spread HCMV due to the expression of IFN-a in the cell.

FIGS. 25A-25C: T cell in vitro stimulation with SmyleDC/pp65. a) CD3$^+$ T cells obtained from HCMV sero-positive donors (n=3) were not stimulated, stimulated with pp65 peptide or SmyleDC or SmyleDC/pp65 in vitro for 16 h. Average frequencies of CD4$^+$ and CD8$^+$ T cells producing IFN-γ$^+$. (n=3), *$p<0.05$ and a representative dot blot analyses from one donor are shown. b) CD8$^+$ T cell expansion in microculture. CD8$^+$ T cells were stimulated with APCs (SmyleDC or SmyleDC/pp65) in vitro at a ratio of 10:1 for two cycles in the presence of IL-2, IL-7, IL-15 cytokines and irradiated feeder cells. T cells with no APCs were used as controls. Left bar graph: Absolute numbers of expanded T cells in each group were determined by trypan blue exclusion. Right bar graph: Expanded T cells were stained with pentamers reactive against pp65 epitopes (A*0201-NLVPMVATA: white/B*07-TPRVTGGGAM: black), *$p<0.05$. c) Cytotoxic assay. CD8$^+$ T cells that were expanded with SmyleDC or SmyleDC/pp65 were seeded at different effector: target (E:T) ratios with targets cells (K562 expressing HLA*A2 or HLA*B7+/−pp65) and co-cultured for 4 hours. Cell supernatants were evaluated for LDH release by measuring a coupled enzymatic assay. The data confirms the functionality of SmyleDC/pp65 to expand memory T cells in vitro reactive against pp65.

FIGS. 26A-26D: Immunization of NRG mice engrafted with CD34$^+$ HSC from G-CSF donors to evaluate the effects of pp65 co-expression in SmyleDC/pp65. a) Experimental scheme. 4 week-old irradiated NRG mice transplanted with G-CSF mobilized stem cells were immunized with either SmyleDC or SmyleDC/pp65 at weeks 10 and 11 after transplantation. Blood, plasma, spleen and bone marrow were collected on week 20. b) Kinetics of human lymphocyte expansion in peripheral blood. Frequencies of human T helper (CD45$^+$/CD4$^+$) and CTL (CD45$^+$/CD8$^+$) in blood were determined before and after DC immunizations at weeks 10, 13 and 20. c) Kinetics of human B cell expansion in peripheral blood. Frequency of human B cells (CD45$^+$/CD19$^+$) cells was determined in blood of immunized NRG mice by FACS analyses. d) Left bar graphs: Absolute numbers of CD4$^+$, CD8$^+$ and CD19$^+$ cells in spleen determined by FACS; Right bar graphs: T cell subsets determined in CD4$^+$ and CD8$^+$ populations recovered from mice immunized with SmyleDC (n=5) and SmyleDC/pp65 (n=2): Naïve (N, white), T Central Memory (TCM, grey) and T Effector Memory (TEM, black). The data indicates the capacity of SmyleDC/pp65 to generate endogenous regeneration of mature helper and cytotoxic T cells.

FIGS. 27A-27D: Functional effects of NRG mice engrafted with adult CD34+ cells and immunized with SmyleDC/pp65. a) Human cytokines detectable in plasma (pg/ml) of NRG mice transplanted with adult HSC and immunized with SmyleDC or SmyleDC/pp65. b) Pooled and sorted CD4$^+$ or CD8$^+$ splenocytes obtained from mice (n=3) transplanted with adult HSC and immunized with SmyleDC/pp65 were expanded in vitro with SmyleDC/pp65 and pulsed with an irrelevant peptide pool (TRP2) or with a pp65 peptide pool on an IFN-γ ELISPOT plate assay. c) Human immunoglobulins (ng/ml) detectable in plasma of NRG mice transplanted with adult HSC and immunized with SmyleDC (n=5) or SmyleDC/pp65 (n=5) in comparison with plasma obtained from human donors (n=3): IgA, IgG$_1$, IgG$_2$, IgG$_3$, IgG$_4$ and IgM. d) Reactivity of mouse plasma IgM and IgG obtained from mice immunized with SmyleDC (n=3) or SmyleDC/pp65 (n=3) against pp65 measured by ELISA. The data demonstrate the requirement of the pp65 to regenerate functional human immune responses (cytokines and immunoglobulins) and antigen-specific responses (T helper, CTL, IgG).

FIGS. 28A-28D and FIG. 28F: Immunization of NRG mice engrafted with UCB CD34$^+$ HSC. a) Experimental scheme. 4 week-old irradiated NRG mice transplanted with UCB stem cells controls (n=7), immunized twice with SmyleDC/pp65 at weeks 10 and 11 (n=8) or four times at weeks 6, 7, 10 and 11 (n=4) after transplantation. Non-immunized mice were used as controls. Blood, plasma, spleen and thymus were collected on week 16. b) Kinetics of human lymphocyte reconstitution in peripheral blood. Frequencies of human T helper (CD45$^+$/CD4$^+$), CTL (CD45$^+$/CD8$^+$) and B cells (CD45$^+$/CD19$^+$) were determined in blood of immunized mice by FACS analyses. c) Kinetics of development of T cell subsets in spleen determined as absolute numbers for human T helper cells or CTLs: Naïve (N), T Central Memory (TCM) and T Effector Memory (TEM).d) Analyses of T cells at different stages of development in thymus. DP: CD45$^+$/CD4$^+$/CD8$^+$, CD4SP:

CD45+/CD4+/CD8−, CD8SP: CD45+/CD4−CD8+ CD3$^{lo}$: CD45+/TCRαβ−/TCRγδ−CD3αβ$^{hi}$: CD45+/TCRαβ+, CD3γδ$^{hi}$: CD45+/TCRγδ+. f) Frequency of Tregs determined in blood as CD4+/CD127−CD25$^{hi}$ or CD4+/CD127−CD25$^{hi}$FOXP3+. The data demonstrates that SmyleDC immunization also stimulates the regeneration of the immune system originated from cord blood neonate stem cells. This effect includes the early development of T cells in the thymus and does not affect the frequency of tolerizing cells as γδT cells and Tregs.

FIGS. 29A-29D: Functional effects of NRG mice engrafted with cord blood CD34+ cells and immunized with different doses of SmyleDC/pp65. Sorted CD3+ splenocytes obtained from mice (n=2) transplanted with cord blood HSC and non-immunized (control), immunized 2 times with SmyleDC/pp65 (2×) or immunized 4 times with SmyleDC/pp65 (4×) were expanded in vitro with SmyleDC/pp65 and not stimulated or pulsed with an irrelevant peptide pool (TRP2) or with a pp65 peptide pool. a) Intracellular analyses of CD4+/IFN-γ+ and b) Intracellular analyses of CD8+/IFN-γ+ were performed to determine the frequencies of reactive T cells. c) Human immunoglobulins (ng/ml) detectable in plasma of control NRG mice transplanted with cord blood HSC (n=5) compared with transplanted mice immunized 4 times with SmyleDC/pp65 (n=5): IgA, IgG$_1$, IgG$_2$, IgG$_3$, IgG$_4$ and IgM. d) Reactivity of mouse plasma IgG obtained from control mice or mice immunized 4 times with SmyleDC/pp65 (n=3) against pp65 measured by ELISA. Human plasma was included as a positive control. The data demonstrates endogenous regeneration of a functional human immune system derived from stem cells of the cord blood, as both T cell and B cell responses against the antigen can be produced.

In a first aspect, the present invention relates to an induced dendritic cell (iDC) engineered to express
   a) at least one cytokine which induces the self-differentiation of human dendritic cell (DC) progenitor cells into DCs; and
   b) at least one antigen;
   for use as a medicament.

In a second aspect, the present invention relates to n iDC engineered to express
   a) at least one cytokine which induces the self-differentiation of human dendritic cell (DC) progenitor cells into DCs; and
   b) at least one antigen;
   for use in the regeneration of the immune system of an immunodeficient subject following transplantation of hematopoietic stem cells (HSC).

In a third aspect, the present invention relates to the iDC according to aspect 2, wherein the vector is a lentiviral vector.

In a fourth aspect, the present invention relates to the iDC according to aspect 3, wherein the lentiviral vector is integrase defective.

In a fifth aspect, the present invention relates to the iDC according to any one of aspects 2 to 4, wherein the iDC expressing at least one antigen expresses at least one cytokine which induces the self-differentiation of human dendritic cell (DC) progenitor cells into DCs.

In a sixth aspect, the present invention relates to the method according to aspect 5, wherein the cytokine is selected from the group consisting of GM-CSF, IL-4, IFN-α, IL-15, TGF-B, TNF-α, FLT3L, IL-3 and CD40L.

In a seventh aspect, the present invention relates to the iDC according to aspect 6, wherein the iDC expresses a combination of cytokines selected from the group consisting of (i) FLT3L and IL-3; (ii) FLT3L and CD40L; (iii) FLT3L and IFN α; (iv) GM-CSF and IFN-α and IL-15; (v) GM-CSF and IFN-α and TNF-α; and (vi) GM-CSF and IFN-α and TGF-B.

In an eighth aspect, the present invention relates to the iDC according to any one of aspects 2 to 7, wherein one antigen is expressed by the iDC is an antigen which can induce a cytotoxic or humoral immune response selected from the group consisting of xeno-reactivity, allo-reactivity, neo-reactivity or auto-immunity In a ninth aspect, the present invention relates to the iDC according to any one of aspects 2 to 8, wherein the immunodeficiency of the subject is an immunodeficiency selected from the group consisting of immunodeficiency caused by ionizing radiation, immunodeficiency caused by the administration of at least one cytotoxic pharmaceutical, primary immunodeficiency and immunodeficiency caused by a pathogen.

In a tenth aspect, the present invention relates to the iDC according to any one of aspects 2 to 9, wherein the hematopoietic stem cell transplant is autologous.

In an eleventh aspect, the present invention relates to the iDC according to any one of aspects 2 to 9, wherein the stem cell transplant is heterologous.

In a twelfth aspect, the present invention relates to the iDC according to any one of aspects 2 to 11, wherein the subject is human.

In a thirteenth aspect, the present invention relates to an iDC engineered to express
   a) at least one cytokine which induces the self-differentiation of human dendritic cell (DC) progenitor cells into DCs; and
   b) at least one antigen;
for use as a medicament for the treatment of cancer which spreads lymphatically or a disease caused by a lymphotrophic pathogen.

In a fourteenth aspect, the present invention relates to an iDC comprising at least one integrase-defective lentiviral vector, wherein said vector mediates expression of
   a) at least one cytokine which induces the self-differentiation of human dendritic cell (DC) progenitor cells into DCs; and
   b) at least one antigen.

In a fifteenth aspect, the present invention relates to a method for regenerating an immune system in an immunodeficient subject comprising the steps of
   a) transplanting hematopoietic stem cells to the subject; and
   b) administering to the subject an induced dendritic cell (iDC) engineered to express at least one antigen and at least one cytokine which induces the self-differentiation of human dendritic cell (DC) progenitor cells into DCs.

In a sixteenth aspect, the present invention relates to the method according the aspect 15, wherein the subject is a mouse and the HSC are derived from a human.

In a seventeenth aspect, the present invention relates to the method according to the aspect 16, wherein the mouse is characterized by the presence of endogenous T-cells and endogenous progenitors of dendritic cells.

In an eighteenth aspect, the method according to aspects 16 or 17, wherein the mouse strain has a primary immune deficiency that leads to dysfunction or absence of adaptive immune system (including T and B cells).

In a nineteenth aspect, the present invention relates to the method according to any one of aspects 16 to 18, wherein the mouse is selected from the group of strains consisting of NOD-Rag1$^{null}$IL2Ry$^{null}$-NRG, NOD/LtSz-SCID/IL2Ry$^{null}$-NSG and NOD/SCID/IL2Ry$^{null}$-NOG.

In a twentieth aspect, the present invention relates to the method according to any one of aspects 15 to 19, wherein the vector mediates the expression of the antigen pp65 and the cytokines (i) GM-CSF and (ii) interferon-α and/or interleukin-4

In a twenty-first aspect, the present invention relates to a mouse with a regenerated immune system produced by a method according to any one of aspects 16 to 20.

In a twenty-second aspect, the present invention relates to use of the mouse according to aspect 21 for the study of the human immune system or for the testing of drugs, implants or devices for their use in humans.

The following example is merely intended to illustrate the invention. They shall not limit the scope of the claims in any way.

EXAMPLES

Example 1

Materials and Methods

Lentiviral Vector Construction and Integrase-defective Lentivirus Production

The self-inactivating (SIN) lentiviral backbone vector and the monocistronic vectors expressing the CMV-pp65 and firefly luciferase, LV-fLUC were previously described (Salguero, G. et al., 2011, "Preconditioning therapy with lentiviral vector-programmed dendritic cells accelerates the homeostatic expansion of antigen-reactive human T cells in NOD.Rag1−/−.IL-2rgammac−/− mice." Hum Gene Ther 22: 1209-1224). Construction of the bicistronic lentiviral vector expressing the human granulocyte-macrophage colony stimulating factor and of the human interferon alpha (LV-G2α) interspaced with a P2A element (RRL-cPPT-CMV-hGMCSF-P2A-hIL4) was constructed and extensively characterized as previously described (Daenthanasanmak, A. et al., 2012, "Integrase-defective lentiviral vectors encoding cytokines induce differentiation of human dendritic cells and stimulate multivalent immune responses in vitro and in vivo." Vaccine 30: 5118-5131). The structural integrity of all constructs was reconfirmed by restriction digestion and sequencing analysis of the promoters and transgenes. Large scale lentivirus production was performed by transient co-transfection of human embryonic kidney 293T cells as formerly described (Stripecke, R., 2009, "Lentiviral vector-mediated genetic programming of mouse and human dendritic cells." Methods Mol Biol 506: 139-158). To generate integrase-defective lentivirus, four packaging plasmids were used in the co-transfection: the plasmid containing the lentiviral vector expressing the cytokines, the plasmid expressing gag/pol containing a D64V point mutation in the integrase gene (pcDNA3g/pD64V.4xCTE), the plasmid expressing rev (pRSV-REV) and the plasmid encoding the VSV-G envelope (pMD.G). Virus supernatants were collected and concentrated by ultracentrifugation and the titers were evaluated by assessing p24 antigen concentration with enzyme-linked immunoabsorbent assay (ELISA) (Cell Biolabs, Inc. San Diego, USA). One µg of p24 equivalent/ml corresponds to approximately $1\times10^7$ infective viral particles/ml.

Human CD34 Positive Peripheral Blood Stem Cell Isolation

Peripheral blood mononuclear cells (PBMCs) were obtained from leukapheresis of hematopoietic adult stem cell transplantation adult donors subjected to haematopoietic stem cell mobilization regimen with G-CSF (Granocyte, Chugai Pharma). All studies were performed in accordance with protocols approved by the Hannover Medical School Ethics Review Board. CD34+ cells were positively selected by MACS using a CD34 magnetic cell isolation kit (Miltenyi Biotech, Bergisch-Gladbach, Germany). After two rounds of positive magnetic selection, cell purity obtained was above 97% with a contamination of CD3+ T cells bellow 0.2% as evaluated by flow cytometry.

Generation of Human Conventional-IFNα and Smyle DCs,

The autologous CD34 negative PBMC fraction was used for further positive selection of CD14$^+$ monocytes using CD14 isolation beads (Miltenyi Biotech). For lentiviral gene transfer, monocytes were kept in culture with serum-free Cellgro medium in the presence of recombinant human GM-CSF and IL-4 (50 ng/ml each, Cellgenix, Freiburg, Germany) for 8 h prior to transduction. For generation of SmyleDC/pp65, $5\times10^6$ CD14$^+$ monocytes were transduced at a multiplicity of infection (M.O.I.) of 5 (corresponding to 2.5 µg/mL p24 equivalent) of both ID-LV-G2α and in the presence of 5 µg/ml protamine sulfate (Valeant, Dusseldorf, Germany) for 16 h. After transduction, Smyle/pp65 DC were washed twice with phosphate-buffered saline (PBS) and further maintained in culture with serum-free Cellgro medium. For production of conventional IFN-α-DCs monocytes were incubated with ID-LV-pp65 as described above. Following 16 h transduction, LV was removed and cells were maintained in culture in the presence of recombinant human GM-CSF (50 ng/ml), and IFN-α (1000 U/ml, PBL InterferonSource, New Jersey, USA). Cytokines for Con-IFN/pp65 were replenished every 3 days, while SmyleDC were incubated without cytokines in the medium. iDC were harvested after 7, 14 and 21 days of culture. For mouse immunizations, Smyle/pp65 at day 1 or Con-IFN/pp65 DC at day 7 after transduction were resuspended in PBS, used for s.c. injection. The number of viable counts was determined with trypan blue exclusion.

Mouse Transplantation with Human HSC

NOD.Cg-Rag1$^{tm1Mom}$Il2rg$^{tm1Wjl}$ (NOD; Rag1$^{-/-}$; IL-2ry$^{-/-}$, NRG) mice were bred and maintained under pathogen free conditions in an IVC system (BioZone, United Kingdom). All procedures involving mice were reviewed and approved by the Lower Saxony and followed the guidelines provided by the Animal Facility at Hannover Medical School. For HSC transplantation, 4-week old mice were sublethally irradiated (450 cGy) using a $^{137}$Cs column irradiator (gammacell, company, country). Mouse recipients were intravenously injected with $5\times10^5$ human CD34+ peripheral blood HSC into the tail vein. Mice were bled at different time points (6, 10 and 13) after human HSC transplantation to monitor the status of human hematopoietic cell engraftment and were sacrificed at week 20 for final analyses. For DC immunizations, Smyle/pp65 or Con-IFN/pp65 DC were collected from culture plates and resuspended at a concentration of $5\times10^5$ cells in 100 µL of PBS. HSC-reconstituted mice were injected at 10 and 11 week after HSC transplantation with DC suspensions by subcutaneously injection into the mouse right hind limb using a 27-gauge needle.

Flow Cytometry Analysis

Engraftment of human hematopoietic cells in human HSC-reconstituted mice was evaluated in peripheral blood and spleens using the following mouse anti-human antibodies: PerCP anti-CD45, Alexa700 anti-CD19, Pacific blue anti-CD4, APC anti-CD3, PE-Cy7 anti-CD8, FITC anti-CD45RA, PE anti-CD62L (Biolegend), PE anti-CD14, FITC anti-Lineage positive, APC anti-CD11c, PE anti-CD123 (Becton Dickinson). For peripheral blood analyses, blood was lysed by two rounds of incubation with erythrocyte lysis buffer (0.83% ammonium chloride/20mMHepes, pH 7.2) for 5 min at room temperature followed by stabilization with cold phosphate buffered saline (PBS) and centrifugation for 5 min at 300 g. Cells were incubated with antibodies for 30 min at 4° C. Harvested spleen cells were treated with erythrocyte lysis buffer (0.83% ammonium chloride/20mMHepes, pH 7.2) for 5 min, washed with phosphate buffered saline (PBS) and incubated with antibodies for 30 min on ice. After a washing step, cells were resuspended in PBS and acquired in LSR flow cytometer (Becton Dickinson). For DC phenotypic characterization the following anti-human antibodies were used: PE anti-CD80, PerCP anti-HLA-DR, APC anti-CD86, APC anti-CD83 (Becton Dickinson). For DC staining, cells were collected, washed once with PBS and incubated with mouse IgG (50 μg/mL) on ice for 15 min followed by incubation with the antibodies. Cells were washed, resuspended in cell fix solution (Becton Dickinson) and further analyzed using a FACSCalibur cytometer. Analyses were performed using FlowJo software (Tree Star, Inc.).

Histology and Immunohistochemistry Analysis of Human T Cell Engraftment

LN from human HSC-reconstituted NRG or C57B16 wild type mice were harvested and embedded in optimal cutting temperature compound (O.C.T. Sakura Finetek, Torrance, Calif., USA) for cryopreservation. Frozen sections (5 μm) were fixed by acetone and stained with monoclonal anti-mouse or human CD3 (eBioscience, San Diego, Calif., USA), anti mouse or human CD11c (eBioscience), anti-mouse LYVE-1 (Dako), anti-CD31 mouse (BD Bioscience). Immunofluorescence analyses were performed in a AXIO-CAM fluorescence microscope (Zeiss).

In Vivo Bio-luminescence Imaging Analyses

Mice were anesthetized with ketamine (100 mg/kg intraperitoneally) and xylazine (10 mg/kg intraperitoneally), and an aqueous solution of d-luciferin (150 mg/kg intraperitoneally) was injected 5 minutes before imaging. Mice were placed into a dark chamber of the charge-coupled device camera (IVIS 200, Xenogen, Cranbury, N.J., USA), and grayscale body surface reference images (digital photograph) were taken under weak illumination. After the light source was switched off, photons emitted from luciferase-expressing cells within the animal body and transmitted through the tissue were quantified over a defined time of up to 5 minutes using the software program Living Image (Xenogen) as an overlay on Igor (Wavemetrics, Seattle, Wash., USA). For anatomical localization, a pseudocolor image representing light intensity (blue, least intense; red, most intense) was generated in Living Image and superimposed over the grayscale reference image. Quantified luminescence consists in averaged photon radiance on the surface of the animal and is expressed as photons/sec/cm$^2$/sr where sr=steradian.

Functional Analyses of pp65-CTLs Recovered from Mouse LN and Spleen

For evaluation of immune responses against CMV-pp65, splenocytes from each group were harvested, pooled stained with APC-conjugated anti-human CD3 and sorted using a XDP cell sorter (Beckman Coulter). Human CD3$^+$ cells were seeded at a density of 10.000 cells per well in anti-human IFN-γ-coated 96-well ELISPOT plate and incubated overnight in the presence of 10 μg/mL of pp65 overlapping peptide pool (Miltenyi). CEF recall peptide pool corresponding to a mixture of CMV, Epstein-Barr virus and influenza virus epitopes (PANA Tecs GmbH, Tuebingen, Germany) was used as positive control. Next day, cells were washed and plates were further incubated with biotin-conjugated anti-human IFN-γ antibodies followed by alkaline phosphatase-conjugated streptavidine. Plates were developed using NBT/BCIP liquid substrate and analyzed in an AELVIS ELISPOT reader (AELVIS GmbH, Hannover, Germany). For analyses of lymphocytes obtained from LN, cells were expanded ex vivo for seven days in the presence of SmyleDC or SmyleDC/pp65 and exposed to pp65 overlapping peptide pool on a ELISPT plate and IFN-γ spots were counted.

Immunoglobulin Production in HSC-NRG Mice

Plasma was harvested from HSC-NRG mice 20 weeks after reconstitution (8 weeks after second Smyle or IFN-conDC) and screened by ELISA for the presence of total human IgM an total human IgG as described elsewhere (Becker, P. D. et al., 2010, "Generation of human antigen-specific monoclonal IgM antibodies using vaccinated "human immune system" mice" *PLoS One* 5). Total IgM and IgG determination was performed by coating 96-well plates either with AffiniPure F(ab')$_2$ fragment goat anti-human IgM (Fc5μ-specific, Jackson ImmunoResearch) or AffiniPure goat anti-human IgG (Fcγ fragment-specific; Jackson ImmunoResearch). Control human serum protein calibrator (Dako) with known IgM (0.8 mg/ml) and IgG (10.4 mg/ml) concentrations was used as a standard to be compared to the samples. After coating, the plates were washed in ELISA wash buffer (PBS, 0.5% Tween-20), blocked with 4% of milk and further incubated with serial dilution of mouse plasma (starting at a dilution of 1:5). Enzyme-conjugated detection antibodies were added at a dilution of 1:2500 for HRP-conjugated anti-IgG and a dilution of 1:5000 for HRP-conjugated anti-IgM (both from Jackson ImmunoResearch). TMB substrate/stop solution (Biosource) was used for the development of the ELISA assay.

Statistical Analysis

Parametric (t test) and non-parametric (Kruskall-Wallis) statistical analyses were performed to compare the differences among groups for engrarftment of hematopoietic lineages in HIS-NRG mice. Analyses were performed in Graph prism 5$^{th}$ version software. All tests were two-sided, and P<0.05 was considered significant.

Results

LV-induced Smyle/pp65 DC Generation and Characterization

Figure 1A:
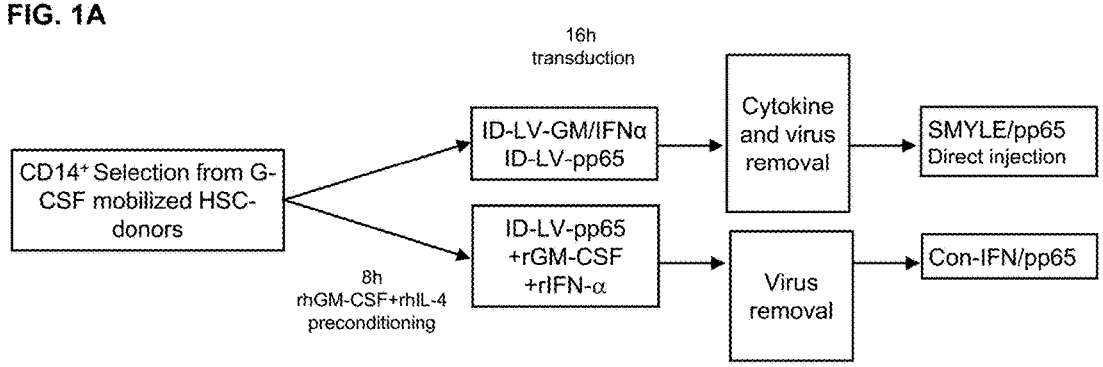
FIGS. 1A-1D: Smyle/pp65 generation and characterization. (a) CD14+ monocytes from GCSF-mobilized healthy donors were isolated by magnetic selection and co-transduced with LV-GM-IFNα and LV-pp65 for Smyle/pp65 or LV-pp65 alone for conventional DC (Con-IFN/pp65) generation. Con-IFN/pp65 DC were maintained throughout the culture in the presence of recombinant cytokines, i.e., GM-CSF and IFN-α (b) Cell viability represented by averaged percentage of recovery was assessed in cultured Smyle/pp65 or Con-IFN/pp65 at different time points (7, 14 and 21 days). (c) Expression of CMV-pp65 and (d) Stability of dendritic cell phenotype was analyzed by flow cytometry in Smyle/pp65 and Con-IFN/pp65 cultured for up to three weeks. Data represent the average of at least three different donors for every time point. *p<0.05.
Figure 1B:
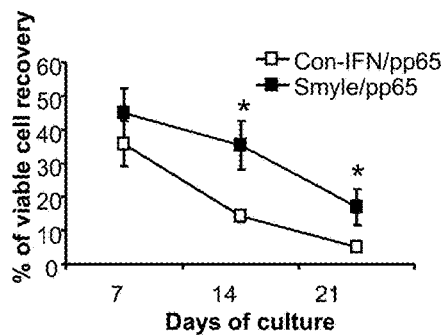
Figure 1C:
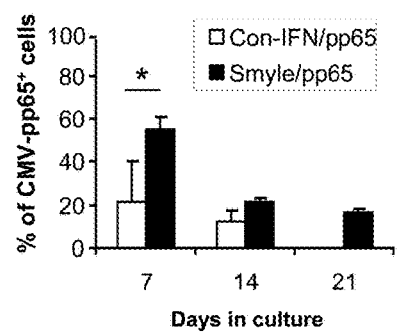
Figure 1D:
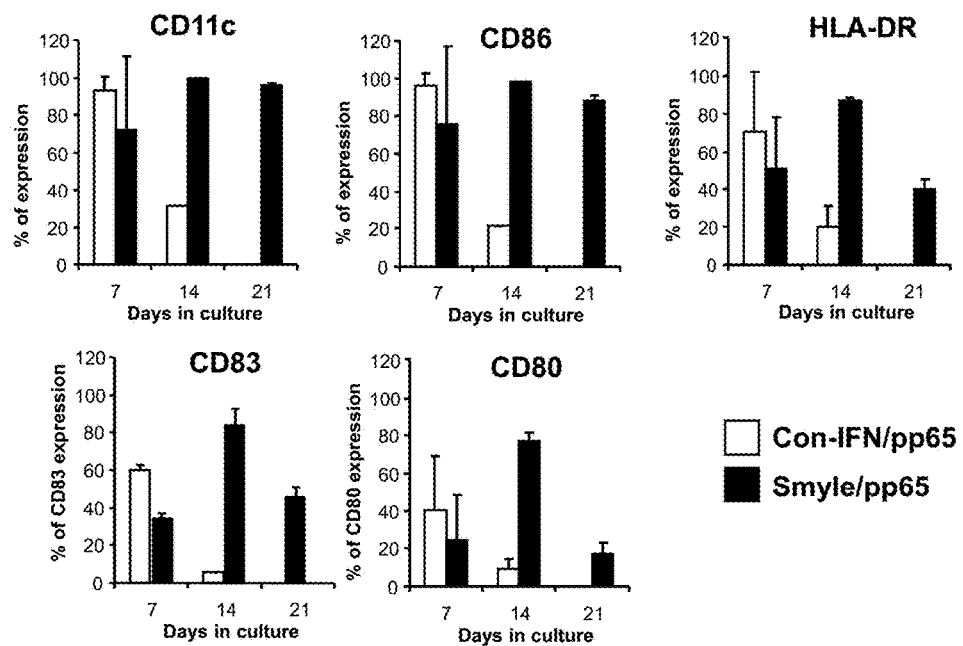

We have recently shown that integrase-defective (ID)-LV used to promote constitutive expression of human GM-CSF and IFNα in human monocytes induced highly viable IFNα-DC with high activating status and high viability and engraftment properties in vivo (Daenthanasanmak, A. et al., 2012, "Integrase-defective lentiviral vectors encoding cytokines induce differentiation of human dendritic cells and stimulate multivalent immune responses in vitro and in vivo" *Vaccine* 30: 5118-5131). These LV-induced DC, named as "Smyle" (Self-differentiated, myeloid-derived, lentivirus-induced) DC, could be additionally co-transduced with a ID-LV for expression of the CMV tegument viral protein pp65. Smyle/pp65 potently stimulated anti CMV-specific CTL responses in vitro and in vivo. Here, we aimed to test the feasibility of Smyle/pp65 DC generation using leukapheresis obtained from GCSF-mobilized hematopoietic stem cell donors (FIG. 1A). Briefly, for Smyle/pp65 generation, CD14$^+$ cells were isolated by magnetic selection of PBMC obtained from GCSF-mobilized HSCT donor leukapheresis and preconditioned with GM-CSF and IL-4 followed by overnight LV co-transduction with bicistronic LV expressing GM-CSF and IFN-α and LV expressing CMV-pp65. After LV removal, Smyle/pp65 were maintained in culture without cytokine supplement. Conventional IFNα_DC expressing pp65 (Con-IFN/pp65) were produced with monoytes similarly transduced with LV-pp65 and maintained in culture supplemented every third day with recombinant human GM-CSF and IFNα. Cells were cultured for up to three weeks to determine their differentiation status, viability and phenotype stability. We were able to recover comparable levels of Con-IFN/pp65 and Smyle/pp65 DC (45 vs. 35.6%, p>0.05) at day 7 of culture (FIG. 1B). Importantly, Smyle/pp65 showed 3-fold higher levels of recovery than Con-IFN already at day 14 of culture (35.4 vs. 14.2% p=0.021). Three weeks after DC culture, both Smyle/pp65 and Con-IFN/pp65 significantly lost viability, yet Smyle/pp65 showed higher levels compared to Con-IFN/pp65 (17 vs. 5%, p<0.05). We also evaluated the differentiation status of Smyle/pp65 and Con-IFN/5pp65 throughout the culture period. Co-expression of pp65 was confirmed by intracellular staining and flow cytometry analyses. Levels of CMV-pp65 expression were maintained higher in Smyle/pp65 than in Con-IFN/pp65 DC (55 vs. 21.2%, p=0.014) (FIG. 1C). On day 7 of culture, both Smyle/pp65 and Con-IFN/pp65 displayed typical DC differentiated phenotype, characterized by high expression levels of CD11c, CD86 and MHC-II (HLA-DR) (FIG. 1D). Both cell types presented comparable maturation status, as shown by CD80 and CD83 expression. Smyle/pp65 maintained a stable expression of immunophenotypic markers at longer culture periods of 14 and 21 days. Despite culture in the presence of recombinant cytokines, Con-IFN/pp65 DC de-differentiated, losing the expression of differentiation and maturation markers.

Figure 2A:
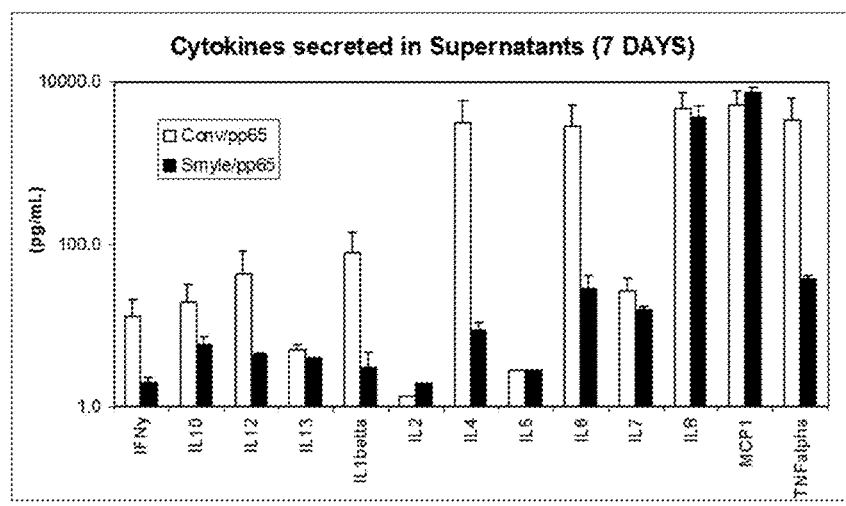
FIGS. 2A-2C: Cytokines accumulated in Smyle/pp65 (not supplemented with recombinant cytokines) and Con-IFN/pp65 (supplemented with recombinant GM-CSF and IFN-α) cell culture supernatants. (a) Cytokine pattern after 7 days. (b) Cytokine pattern after 14 days. (c) Cytokine pattern after 21 days.
Figure 2B:
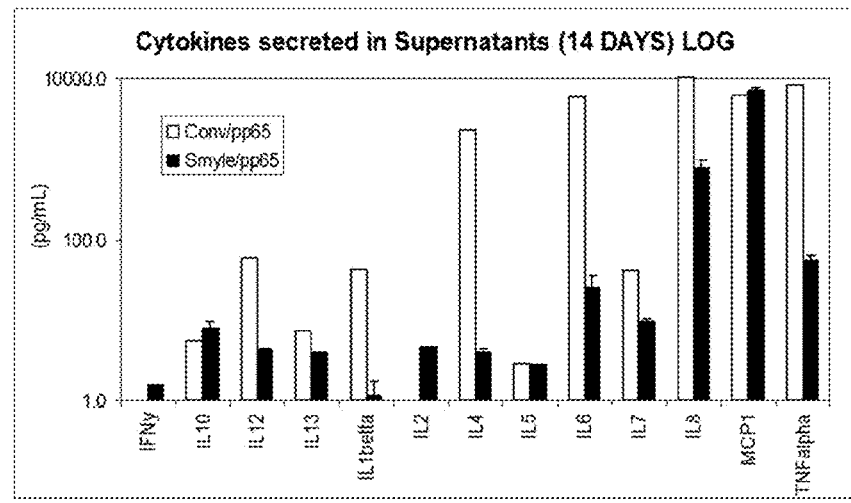
Figure 2C:
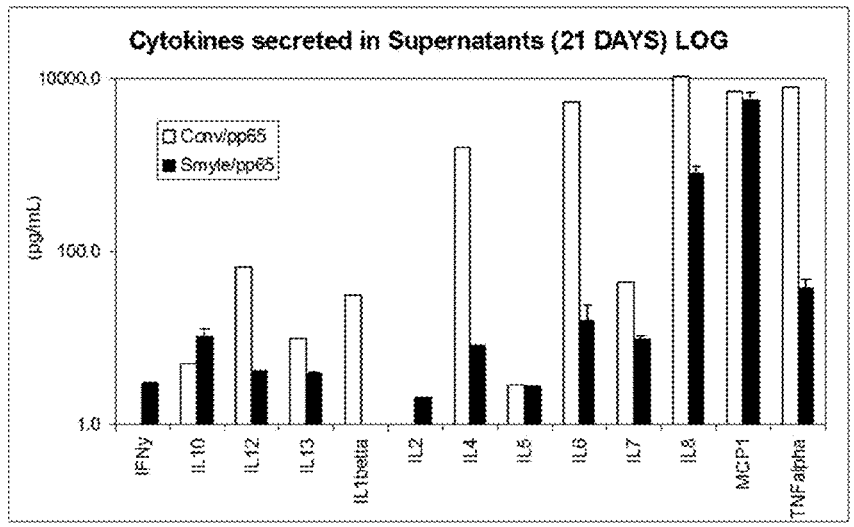

Both Smyle/pp65 and Con-IFN/pp65 maintained in culture secreted several endogenously up-regulated cytokines, that accumulated in the culture supernatants and were detectable by cytokine array analyses: IFN-g, IL-10, IL-12, IL-13, IL-1β, IL-2, IL-4, IL-5, IL-6, IL-7, IL-8, MCP-1 and TNF-α showed an overall enhanced activation of Con-IFN/pp65 (FIG. 2). Accumulated levels of IL-1β, 4, 6, 8, 12 were higher for Con-IFN/pp65 cultures, which implies that, although these cells were continuously exposed to high levels of several cytokines, their functionality in terms of maintaining expression of relevant immunophenotypic markers was reduced.

Smyle/pp65 Supports Recovery of Lymphocyte Compartment after Human HSC Transplantation In order to evaluate the potential of Smyle/pp65 to induce immune-reconstitution in a HSC transplantation setting, we first established a humanized immune system model of (HIS) by transferring human CD34$^+$ cells into four-week old, sub-lethally irradiated NOD.Rag1$^{-/-}$.IL2rγ$^{-/-}$ (NRG) mice. We detected CD3$^+$ human T cells in peripheral blood already at six weeks post HSCT (0.35%), reaching average frequencies of 8.6% twenty weeks after CD34$^+$ HSC transfer (data not shown). Human CD19$^+$ B cells predominated within detectable human CD45$^+$ cells, with levels ranging from 84% (week 6) up to 77% (week 20) (data not shown). 20 weeks after HSC reconstitution of HIS-NRG, human CD45$^+$ cells corresponded to 3.9% of total splenocytes and CD19$^+$ B cells represented to the majority of the human cell content (84%). Human CD3$^+$ T lymphocytes corresponded to 7.8% of human CD45-expressing cells and contained CD4$^+$ and CD8$^+$ at a ratio of 1:1 (data not shown).

Figure 3A:
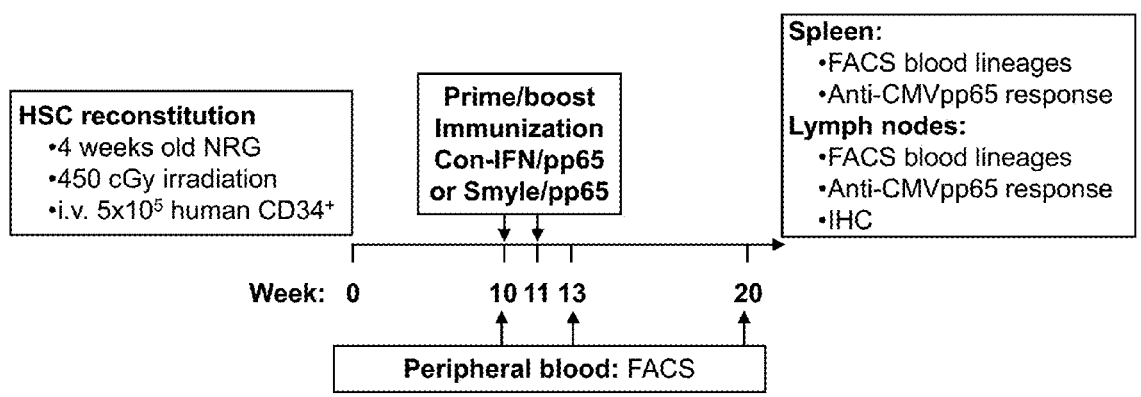
FIGS. 3A-3B: Smyle/pp65 immunization significantly enhances the frequency of human CD3+ T cells in peripheral blood of HIS-NRG mice. (a) HIS-NRG mice were generated by transfer of human $CD34^+$ hematopoietic stem cells (HSC). Mice were subcutaneously injected with Smyle/pp65 or Con/pp65 in the right flanks at week 10 and 11 after HSC-reconstitution. (b) Frequency of CD45+/CD3+ human T cells in peripheral blood of control, Smyle/pp65 or Con-IFN/pp65-immunized HIS-mice in weeks 10, 13 and 20 after HSCT.
Figure 3B:
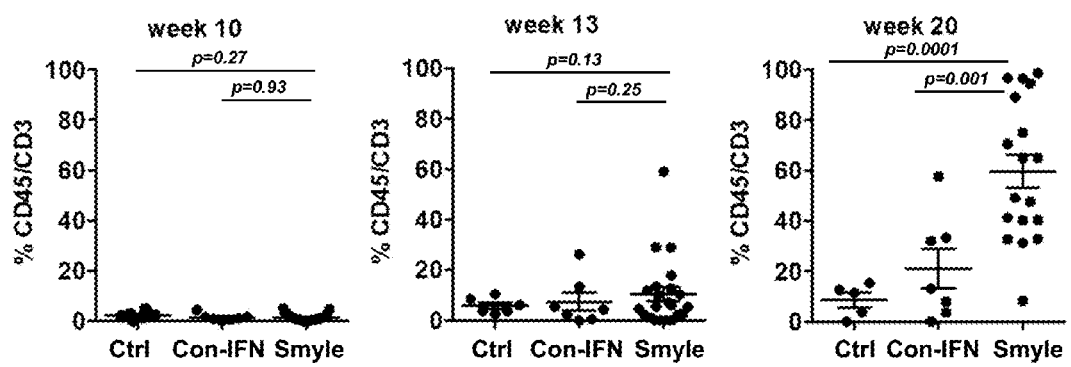

We next assessed whether immunization with Smyle/pp65 improved immune reconstitution in HIS-NRG mice. We followed a prime/boost immunization scheme consisting in one injection of DC in week 10 after HSCT followed by a boost injection one week later. Immunizations were performed by subcutaneous injections of Smyle/pp65 harvested immediately after LV-transduction or 7 days-cultured Con-IFN/pp65. DC cell suspensions (5×10$^5$) were injected into the right flank, as previously described (Salguero, G. et al., 2011, "Preconditioning therapy with lentiviral vector-programmed dendritic cells accelerates the homeostatic expansion of antigen-reactive human T cells in NOD.Rag1–/–.IL-2rgammac–/– mice" Hum Gene Ther 22: 1209-1224). Non-immunized mice served as controls (FIG. 3A). We first evaluated the effect of DC injections on the reconstitution of the human CD45$^+$ cells in peripheral blood. Frequencies of human CD45$^+$ were similar in all groups before immunization at week 10. One week after prime/boost immunization, mice immunized with Smyle/pp65 showed significantly enhanced levels of human CD45$^+$ cells as compared with non-immunized controls (1.7% vs. 0.64%, p=0.01). CD45$^+$ cell frequencies were not significantly higher in Con-IFN/pp65-immunized mice (1.6% compared to controls, p=0.09). Importantly, significant enhanced levels of CD45$^+$ were maintained 8 weeks after Smyle/pp65 immunization compared with mouse controls (1.9% vs. 0.2%, p=0.03). Mice vaccinated with Con-IFN/pp65 also showed higher but no significant levels of CD45$^+$ cells in blood (1.3% vs, 0.2%, p=0.08). We next analyzed the T cell compartment after DC immunization. Smyle/pp65 immunization led to early significant increase of CD3$^+$ frequency in peripheral blood compared to control mice (0.16% vs. 0.03%, p<0.04) and supported long term engraftment of human T cells compared with controls (1.8% vs. 0.03%, p=0.04) 20 weeks after HSCT. (FIG. 3B). Remarkably, Con-IFN/pp65-immunization did not induce neither early, nor long term increased levels of human CD3$^+$ T cells in HIS-NRG mice (0.15%, p=0.26+1 week; 0.37%, p=0.31+8 weeks after DC injection, compared to controls). Analysis of the relative frequency of human T lymphocytes among CD45$^+$ cells 8 week after DC immunization, showed significant enhanced frequency of CD3$^+$ compartment in Smyle/pp65 immunized mice compared to controls (59.7% vs. 8.6%, p=0.0001) and Con-IFN/pp65 (59.7% vs. 21.7%, p=0.001) and confirmed that long term engraftment of human CD45$^+$ cells was determined by expansion of the human T cell compartment in these mice.

Figure 4A:
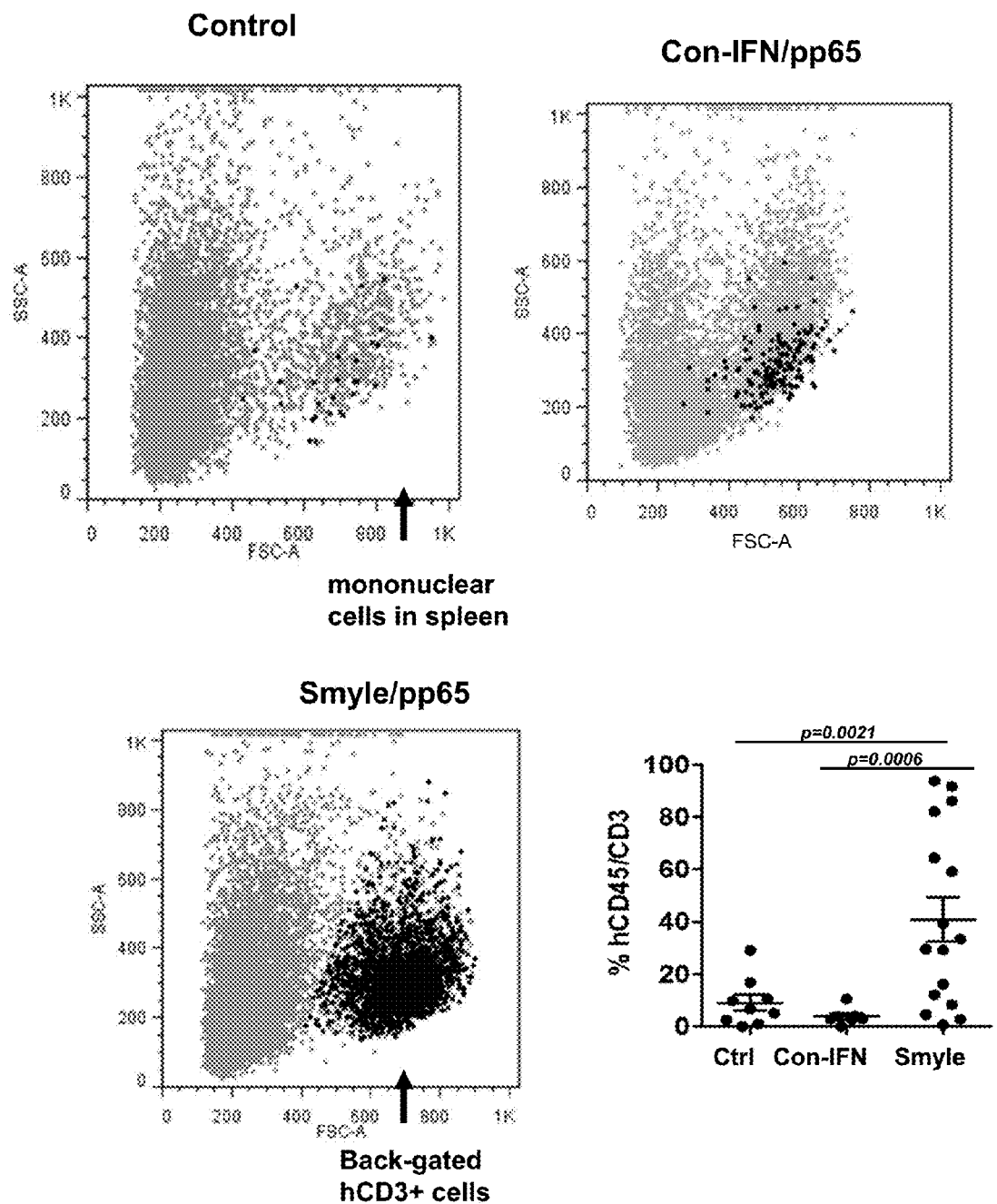
FIGS. 4A-4B: Smyle/pp65 immunization significantly enhances the frequency of human CD3+ T cells and effector memory cytotoxic T cells in HIS-NRG mice (a) Frequency of human $CD45^+$ and $CD3^+$ cells in mononuclear cells obtained from spleen of HIS-NRG mice. (b) Relative frequency of human $CD4^+$ and $CD8^+$ lymphocyte subsets and the corresponding frequencies of $CD45RA^+/CD62L^+$ naïve and effector memory $CD45RA^-$ $CD62L^-$ subsets in spleens from HIS-mice twenty weeks after HSCT. *p<0.05.
Figure 4B:
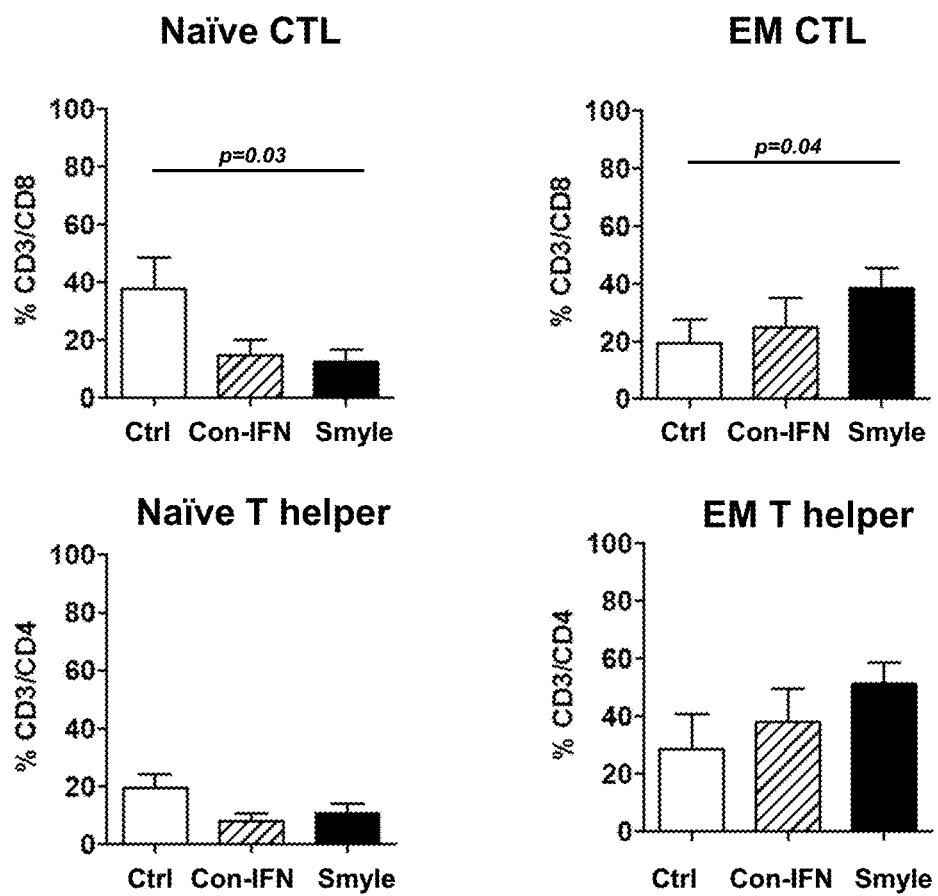

We further analyzed the cell content of spleens from vaccinated and control mice 20 week after HSC reconstitution (FIG. 4). Smyle/pp65 immunized mice showed significantly higher engraftment levels of human CD45$^+$ compared to non-immunized (19.1% vs. 3.1%, p=0.007) and Con-IFN/pp65-immunized (19.1% vs. 5.9%, p=0.01) mice. Accordingly, higher frequencies of human CD3$^+$ cells were observed in Smyle/pp65 immunized mice as compared to control mice (10.1% vs. 0.31%, p=0.007), corresponding to 40.8% of total human CD45$^+$ cells (FIG. 4A). Con-IFN/pp65 immunization failed to enhance the frequency of CD3$^+$ cells (0.17%, p=0.5 vs. control), corresponding to only 3.9% of CD45$^+$ cells in spleen. Distribution of lymphocyte subsets within CD3$^+$ T cells were further analyzed in reconstituted NRG mice spleens (FIG. 4B). Although we did not observe significant differences among CD3$^+$/CD8$^+$ cells in the three groups (control, 51%; Con-IFN/pp65 40.9%; Smyle/pp65 44.2%, p>0.05), we found significant reduced levels of CD8$^+$/CD45RA$^+$/CD62L$^+$ naïve cells in Smyle/pp65-immunized spleenocytes, compared to non-immunized controls (12.3%. vs. 37.49%, p=0.03).

Conversely, frequencies of CD8$^+$/CD45RA$^-$CD62L$^-$ effector memory T cells in Smyle/pp65 were significantly higher than control NRG mice (38.5% vs. 19.5%, p=0.04).

Similar but not significant distribution of CD8$^+$ T cells subsets was found in mice injected with Con-IFN/pp65 DCs for Naïve (14.5%) and effector memory (24.7%) populations. Analysis of CD3$^+$/CD4$^+$ frequencies did not show statistical differences among mouse groups for total CD4$^+$ T cells (control, 44.7%; Con-IFN/pp65 34.7%; Smyle/pp65 50%, p>0.05). Nevertheless, reduction in Naïve and increase in effector memory T cells due to Con-IFN/pp65 and Smyle/pp65 immunizations compared to controls were also seen but were not significant. Taken these data together, human Smyle/pp65 immunization after HSCT promoted a rapid and sustained reconstitution of the T cell compartment and significantly favoured the expansion of CD8$^+$ T- and in less extent CD4$^+$, with a predominantly effector memory phenotype.

Smyle/pp65 Immunization Induces Reconstitution of Peripheral Lymph Nodes.

Figure 5A:
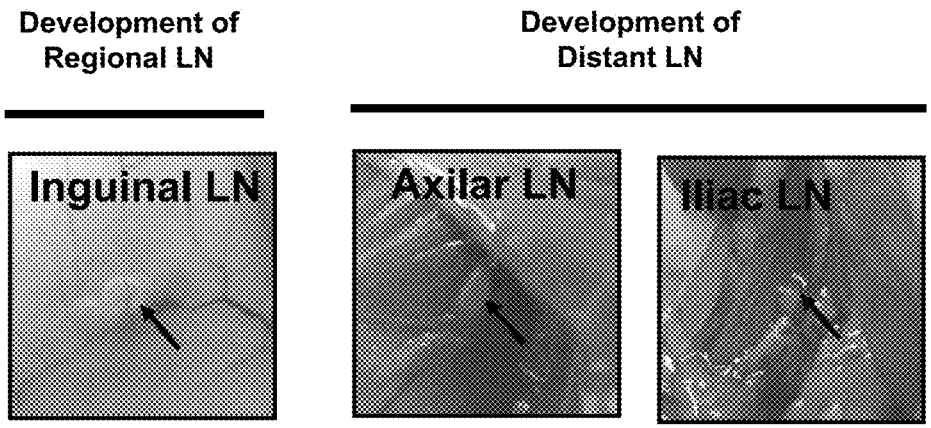
FIGS. 5A-5B: Macroscopic detection of lymph nodes after immunization of HIS-NRG with Smyle/pp65. (a) Macroscopic detection of peripheral lymph nodes (LN) in mice immunized with Smyle/pp65 cells. (b) Frequency of mice showing detectable LN in different parts of the body.
Figure 5B:
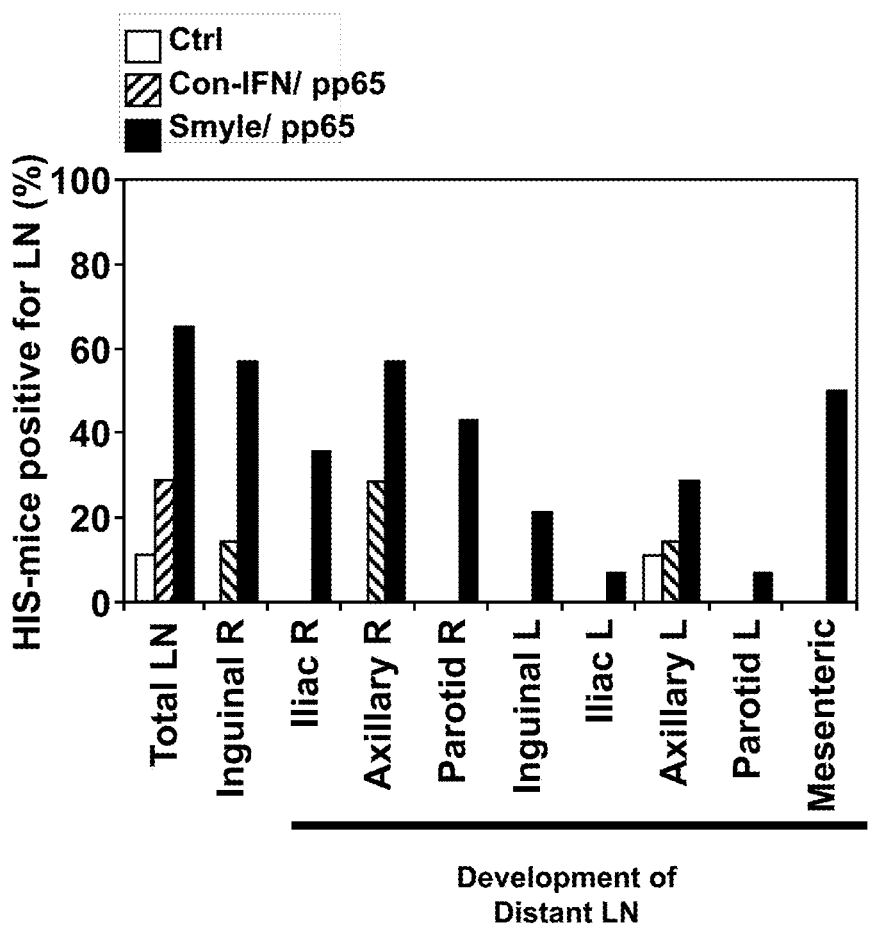

We next analyzed mice injected with Smyle/pp65 or Con-IFN/pp65 DCs for the presence of lymph nodes (LN) 20 weeks after HSC reconstitution. We detected a high frequency of LN formation in mice injected with Smyle/pp65 (65%), whereas control mice or mice injected with Con-IFN/pp65 showed low occurrence of LN structures (11% and 28%, respectively) (FIG. 5A). Quantification of the frequency of LN in different regions of be animal body revealed a strong correlation between the DC injection site and the formation of LN at the corresponding draining site (FIG. 5B). Inguinal (57%), iliac (35%) and axillary (56%) LNs were observed in mice immunized with Smyle/pp65, compared to complete absence of LN in control mice at the same side. Importantly, Con-IFN/pp65 injection did not induce iliac LN formation and only induced formation of inguinal and axillary LN in 14% and 28% mice, respectively.

Figure 6:
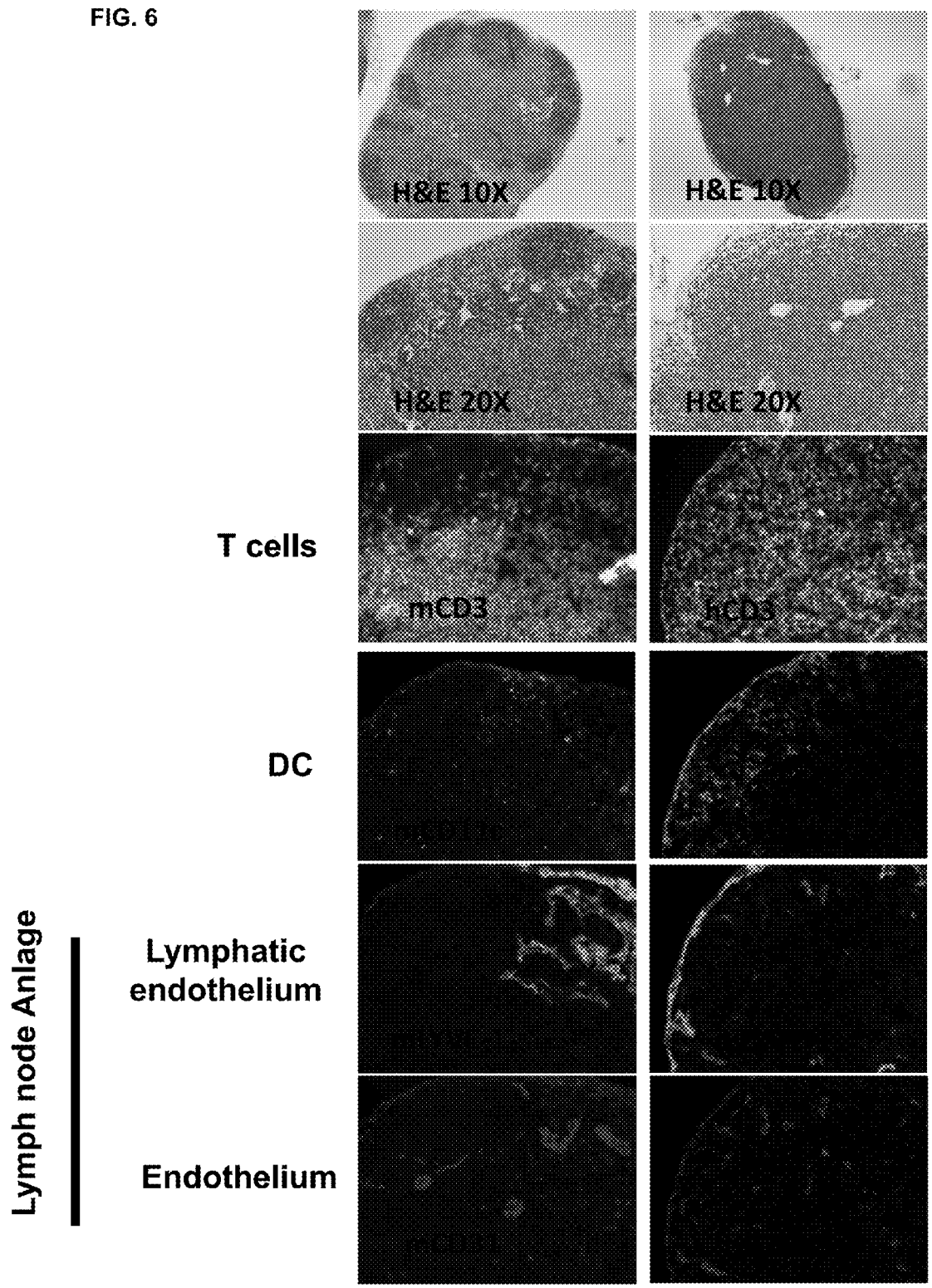
FIG. 6: Immunofluorescence analyses of LN obtained from wild type C57BL/6 and Smyle/pp65 immunized HIS-mice. Human T cells and DC fill up the LN Anlage in HIS-NRG mice immunized mice.

We next performed immunohistological analyses of LN obtained from Smyle/pp65-imunized NRG mice. LN architecture in LN from reconstituted NRG showed lack of B cell follicles compared to normal wild type LNs obtained from wild type C57BL/6 (FIG. 6). Humanized LN were predominantly populated by human CD3$^+$ T cells and we also observed the presence of human DC (CD11c+). LN were encapsulated by a layer of cells positive for mouse lymphatic vascular cell (LYVE-1) and mouse endothelial vascular CD31 marker. Importantly, we also observed the presence of structures resembling high endothelial venules (HEV) that were positive for mouse CD31, suggesting a rudimentary vascular organization process within the forming LN.

Figure 7A:
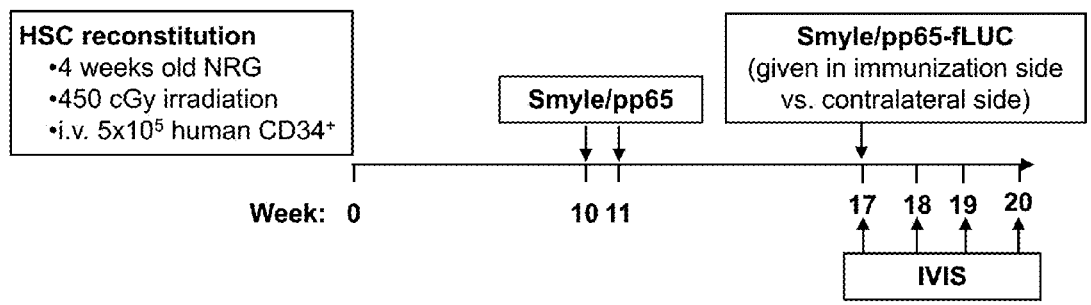
FIGS. 7A-7C: Optical imaging analyses for monitoring the migration of SmyleDC/pp65-fLUC administered s.c. into HIS-NRG mice previously immunized with SmyleDC/pp65. (a) Scheme of experiment. (b) Detection of bioluminescence signal in HIS-NRG mice. (c) Quantified bioluminescence signal detected on the same side versus contra-lateral side, where SmyledC/pp65-fLUC was injected.
Figure 7B:
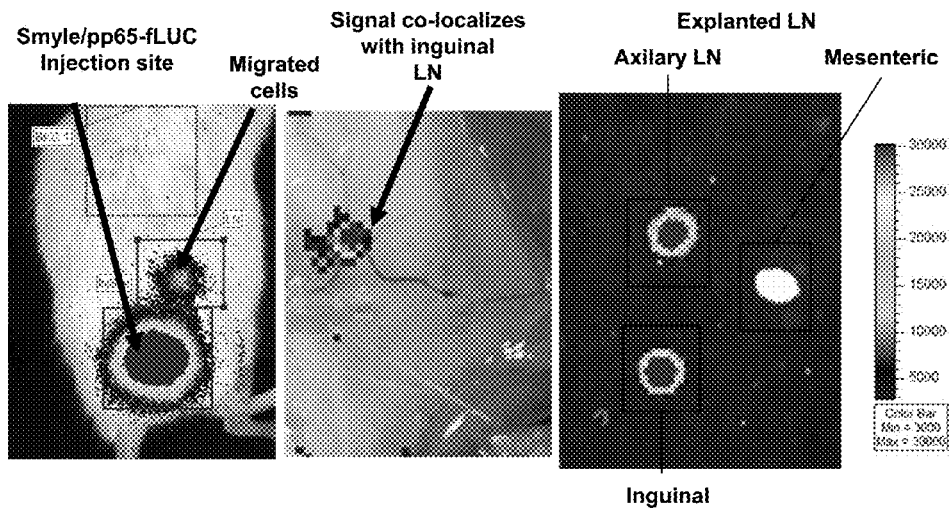
Figure 7C:
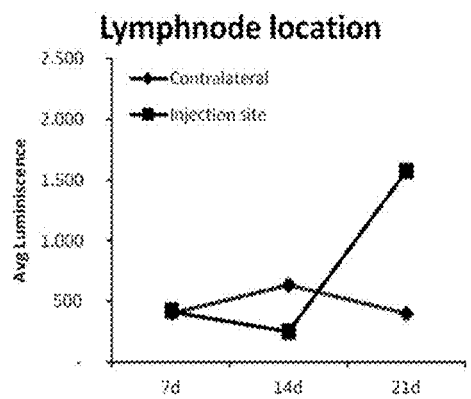

We next evaluated whether injected Smyle/pp65 DC were able to migrate to the reconstituted LN formed in HIS-NRG mice. Smyle/pp65 were co-transduced with a LV expressing firefly luciferase (LV-fLUC), such that they could produce bioluminescence upon exposure to Luciferin. Smyle/pp65-fLUC were injected into the hind limb of HSC-NRG mice 6 weeks after immunization at the right side, where LNs were more frequently found (FIG. 7). As a control for DC migration, we injected fLUC-Smyle/pp65 in the contralateral flank. Engraftment and migration of fLUC-Smyle/pp65 was followed weekly by in vivo bioluminescence imaging. We found accumulation of bioluminescence signal at the LN position in the injection side on day 21 after DC injection as compared to the same location in the contralateral flank. Furthermore, when mice were euthanized and LN were exposed, Smyle/pp65 luminescence was located in the formed inguinal LN, the ipsilateral axillary LN but not intraabdominal LN such as mesenteric (FIG. 7). This data indicates that Smyle/pp65 DC are able to migrate to sites were regional draining LN Anlage are located, and trigger LN formation.

Smyle/pp65 Induces Specific Immune Responses in HIS-NRG Mice

Figure 8A:
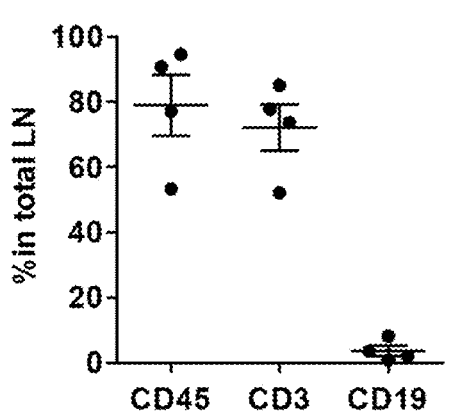
FIGS. 8A-8D: Characterization of CMV-specific cytotoxic T cell responses after HIS-NRG immunization (a) Frequency of human $CD45^+$, $CD3^+$ and $CD19^+$ cells in LN recovered from HIS-NRG immunized with Smyle/pp65. (b) Relative frequencies of human $CD4^+$ and $CD8^+$ T cells $CD45RA^+/CD62L^+$ naïve, effector memory (EM) $CD45RA^-CD62L^-$, central memory (CM) $CD45RA^-CD62L^+$ and $CD45RA^+/CD62L^-$ terminal effector (TE). (c) Cells were obtained from LN isolated from Smyle/pp65-immunized mice and co-cultured for 7 days with autologous Smyle/pp65 or Smyle (without antigen). Re-stimulation was performed by overnight incubation with CMV-pp65 overlapping peptides and IFNγ spots were counted. (d) Human $CD3^+$ cells sorted from splenocytes obtained from control, Con-IFN/pp65 and Smyle/pp65-immunized HIS-NRG, activated for 72 h with human anti-CD2, CD3 and CD28 antibodies in the presence of hIL-7 and hIL-15.
Figure 8B:
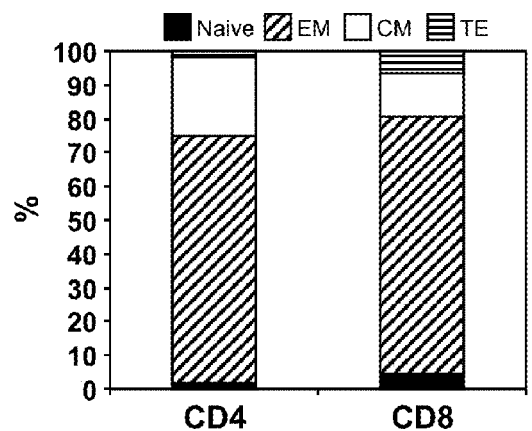
Figure 8C:
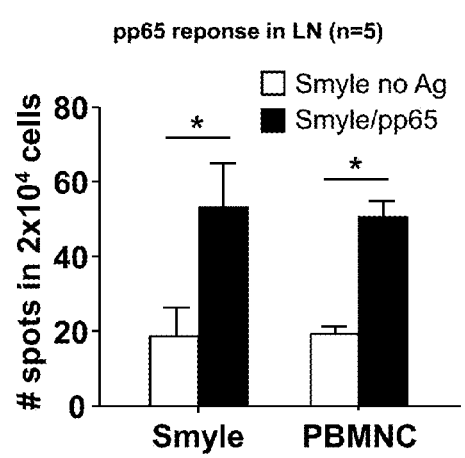
Figure 8D:
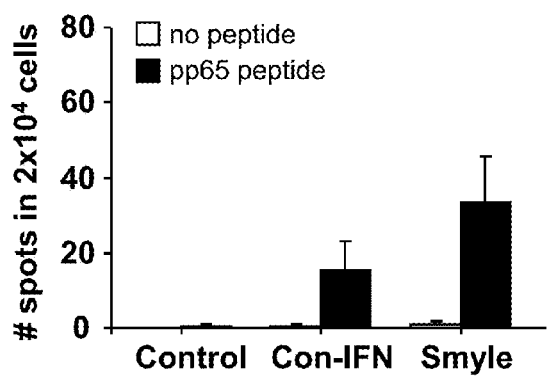

We have previously demonstrated that Smyle/pp65 stimulates anti-pp65 specific responses in a peripheral blood lymphocyte (PBL) mouse model (Daenthanasanmak, A. et al., 2012, "Integrase-defective lentiviral vectors encoding cytokines induce differentiation of human dendritic cells and stimulate multivalent immune responses in vitro and in vivo." Vaccine 30: 5118-5131). Here we evaluate whether Smyle/pp65 immunization reconstituted NRG mice could stimulate specific T cell responses against CMV-pp65. Since we observed a significant effect of Smyle/pp65 in LN formation, we first wanted to test if these findings correlated with enhanced antigen specific reactivity against CMV-pp65 in local LN. We first evaluated the cell content of reconstituted LN after Smyle/pp65 immunization by flow cytometry. The majority of LN cells were human CD45$^+$ (77%), with 73% corresponding to CD3$^+$ T lymphocytes and 3.8% corresponding to CD19$^+$ B cells (FIG. 8A). Among human CD3$^+$ cells we found that 42% were CD4$^+$ and 56% were CD8$^+$ 56%, with a predominance of effector memory phenotype for both T cell subsets (80% and 76% respectively) (FIG. 8B). In order to measure CMV-pp65 specific responses, LN cells were isolated 8 weeks after immunization and ex-vivo expanded in the presence of Smyle/pp65 DC for 7 days. SmyleDC not expressing the CMV-pp65 antigen served as controls (FIG. 8C). After DC co-culture, cells were collected and seeded in IFN-γ-coated plates, re-stimulated with CMV-pp65 overlapping pool peptide and analyzed by ELISPOT for IFN-γ production. PBMNC from CMV-reactive healthy donor were used as positive control for IFN-γ production. Remarkably, LN cells showed significant reactivity against CMV-pp65 after ex-vivo expansion as compared with LN cells in the presence of Smyle DC with out antigen (53 vs. 18.7 spots, p<0.021, n=5 mouse donors) (FIG. 8C). In addition, we evaluated systemic specific immune responses against CMV, by recovering human CD3$^+$ T cells from spleens of control, Smyle/pp65 and Con-IFN/pp65-immunized NRG mice (FIG. 8D). We first promoted T cell proliferation, by incubation for 48 h with human anti-CD2, anti-CD3 and anti-CD28 beads in the presence of human recombinant IL-7 and IL-15 followed by co-culture with Smyle/pp65 DC for additional 7 days in the presence of IL7/IL15. Cells co-cultured with Smyle DC lacking the expression of CMV-pp65 served as controls. T cells recovered from spleens of HSC-NRG mice immunized with Smyle/pp65 and further expanded with Smyle/pp65 showed significant increased of averaged of positive spots compared to controls (33.6 spots vs. 0.5, p<0.05) (FIG. 8D). Conversely, T cells recovered from spleens of Conv-IFN/pp65-injected mice had reduced CMV-pp65 (15.5 averaged spots, p>0.05 vs. Smyle/pp65).

Immunoglobulin Production in HSC-NRG Mice

Figure 9A:
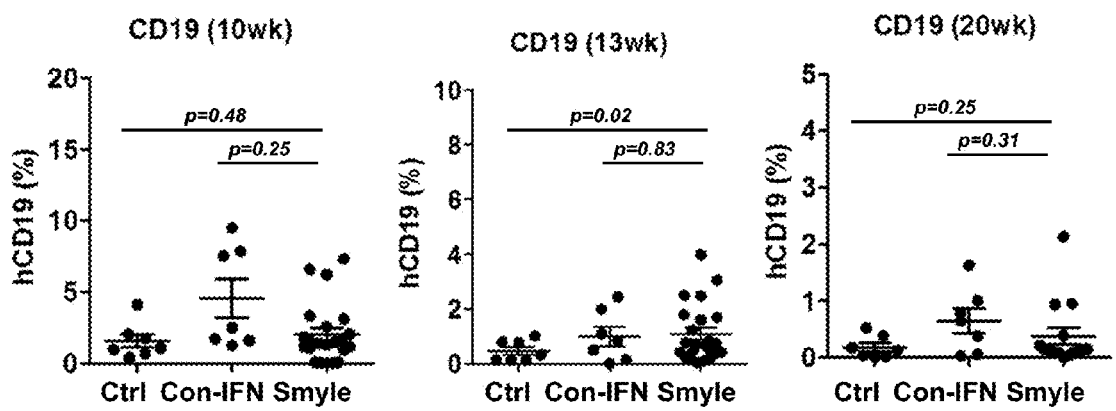
FIGS. 9A-9C: B cell responses in HIS-NRG mice. Frequency of human B cells in peripheral blood (A) and spleen (B) and detection of human immunoglobulin G and M in the sera of HIS-NRG (C).
Figure 9B:
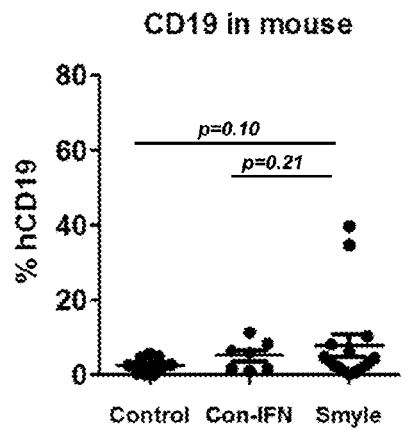
Figure 9C:
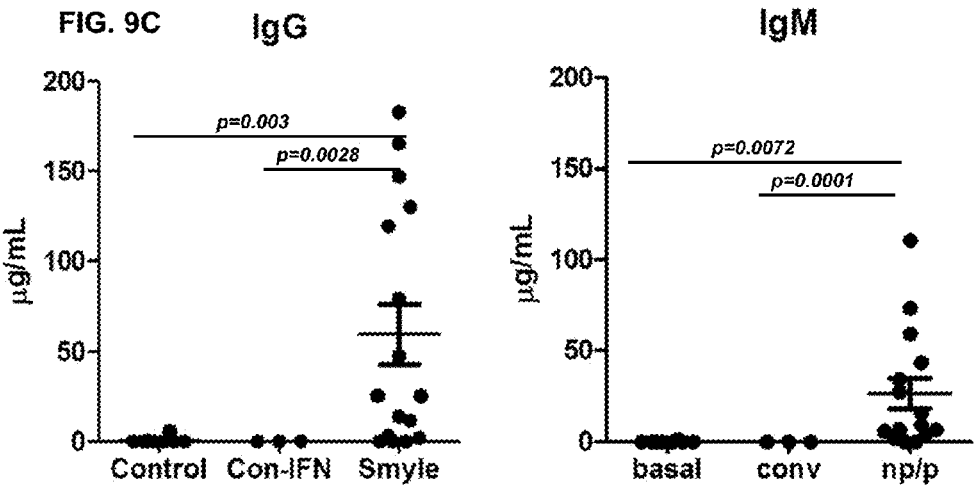

We characterized the B lymphocyte compartment in reconstituted NRG mice DC after immunization. Frequency of CD19$^+$ B lymphocytes (this is a relatively early B cell population) was not significantly different among all groups previous immunization (1.6%, 4.5% and 2% for control, Con-IFN/pp65 and Smyle/pp65 respectively) (FIG. 9A). One week after second DC immunization overall levels of CD19$^+$ B cells were decreased, however Smyle/pp65-injected NRG mice showed higher frequencies of B cells as compared with control and Con-IFN/pp65-injected mice (1.1% vs. 0.4% and 0.9% respectively, p=0.02). By week eight post immunization, overall frequencies of B cell were below 1% in all groups (control 0.18%; Con-IFN/pp65 0.1%; Smyle/pp65 0.37%). We were also able to recover B cells in spleens eight weeks post-immunization and observed non-significant differences of human CD19$^+$ cells among controls (2.5%), Con-IFN/pp65 (5.1%) and Smyle/pp65-immunized (7.8%) NRG mice. In order to evaluate the functionality of human B cells in reconstituted mice, we further measured immunoglobulin (Ig) G and M concentration in plasma from NRG mice eight weeks after DC immunization. Remarkably, we found significantly higher levels of IgG in Smyle/pp65-injected mice (59.6 µg/mL) compared with almost undetectable levels in control (0.78 µg/mL) and Con-IFN/pp65-immunized (0.047 µg/mL) mice. Similarly, IgM concentration was higher in plasma from Smyle/pp65-injected mice (26.6%) compared to control and Con-IFN/pp65 (0.15 and 0.01 µg/mL, respectively).

Discussion

DC are pivotal for "organizing" the development of LN, which are the most effective site for stimulation of adaptive T and B cell immune responses. Using a modality of iDC (IDLV-SmyleDC/pp65) described above, we evaluated the effects of DC vaccination in an immunodeficient mouse strain transplanted with human HSC. Lymphopenic mouse models making use of transplanted human hematopoieitic stem cell precursors/stem cells (such as CD34$^+$ cells) have been developed worldwide in order to reconstitute the human immune system in mice (Lepus C M et al. "Comparison of Human Fetal Liver, Umbilical Cord Blood, and Adult Blood Hematopoietic Stem Cell Engraftment in NOD-scid/γc−/−, Balb/c-Rag1$^{−/−}$γc$^{−/−}$, and C.B-17-scid/bg Immunodeficient Mice". *Human immunology*. October 2009; 70(10):790-802). These models have been explored to follow several steps of hematologic reconstitution such as HSC engraftment in bone marrow niches, mobilization, self-renewal, differentiation in several lineages. Long-term (16-20 weeks) follow-up of these mice after HSCT showed a generally impaired CD8$^+$ T cell maintenance (Andre M C et al. "Long-term human CD34+ stem cell-engrafted nonobese diabetic/SCID/IL-2R gamma(null) mice show impaired CD8$^+$ T cell maintenance and a functional arrest of immature NK cells". *J Immunol*. Sep. 1 2010; 185(5):2710-2720). Mice transplanted with human HSC did not develop regenerated LN containing viable and functional T cells. Lymph nodes are the specialized tissues where the drained lymph is "filtered" for immune surveillance of pathogenic conditions (such as infections, cancer). Due to its specialized architecture, lymph nodes allow optimization of antigen presentation to T cells for priming and amplification of adaptive immune responses. Demonstration of antigen-specific CTL responses generated from LN in humanized mice have not been described with the previously available approaches such as exploring transgenic expression of human cytokines that are critical for adaptive immune responses (for example IL-7, IL-15, GMCSF) or by transgenic approaches of single human MHC class I or II molecules. On the other hand, the iDC immunization approach described here brings together into the immune deficient host a highly viable human professional antigen presenting cell perfectly matched with all the MHC molecules expressed by human stem cell graft that expresses a combination of several human cytokines and a highly immunogenic antigen (known to stimulate several different MHC-restricted immune responses). Thus, based on these properties, SmyleDC/pp65 immunization produced a dramatic increase in the absolute frequency of human T cells circulating in the peripheral blood, CTL responses against the pp65 CMV viral antigen and high levels of human IgG in the plasma demonstrating that adaptive human immune responses in the mice have been regenerated.

Moreover, the ability of the iDC to promote regeneration of lymph nodes concomitantly with stimulation of adaptive T and B cell immune responses in immunodeficient mice reconstituted with human HSC indicates that iDC have properties that support a general regeneration of a functional immune system from transplanted human HSC. Thus, iDC may be used in human patients who were transplanted with HSC in order to accelerate the development of a fully functional immune system, thus decreasing the susceptibility to infectious diseases or relapse of the malignancy after HSC transplantation.

Example 2

(Based on Example 1 but Comprising Additional Data and Partially Expanded Analysis of the Results)

Material and Methods

Lentiviral Vector Construction and Integrase-defective Lentivirus Production

The self-inactivating (SIN) lentiviral backbone vector and the monocistronic vectors expressing the CMV-pp65 were previously described (Sato, Caux et al. 1993; Salguero, Sundarasetty et al. 2011). Construction of the bicistronic lentiviral vector expressing the human granulocyte-macrophage colony stimulating factor (huGM-CSF) and of the human interferon alpha (huIFN-α) (LV-G2α) interspaced with a P2A element (RRL-cPPT-CMV-hGMCSF-P2A-hIL4) was constructed and extensively characterized as previously described (Daenthanasanmak, Salguero et al. 2012). The structural integrity of all constructs was reconfirmed by restriction digestion and sequencing analysis of the promoters and transgenes. Large scale lentivirus production was performed by transient co-transfection of human embryonic kidney 293T cells as formerly described (Stripecke 2009). To generate integrase-defective lentivirus, four packaging plasmids were used in the co-transfection: the plasmid containing the lentiviral vector expressing the cytokines, the plasmid expressing gag/pol containing a D64V point mutation in the integrase gene (pcDNA3g/pD64V.4×CTE), the plasmid expressing rev (pRSV-REV) and the plasmid encoding the VSV-G envelope (pMD.G). Virus supernatants were collected and concentrated by ultracentrifugation and the titers were evaluated by assessing p24 antigen concentration with enzyme-linked immunoabsorbent assay (ELISA) (Cell Biolabs, Inc. San Diego, USA). One µg of p24 equivalent/ml corresponds to approximately $1 \times 10^7$ infective viral particles/ml.

Human CD34 Positive Peripheral Blood Stem Cell Isolation

Peripheral blood mononuclear cells (PBMCs) were obtained from leukapheresis of hematopoietic adult stem cell transplantation adult donors subjected to haematopoietic stem cell mobilization regimen with G-CSF (Granocyte, Chugai Pharma). All studies were performed in accordance with protocols approved by the Hannover Medical School Ethics Review Board. Hematopoietic stem cells (HSC) CD34 cells were positively selected by MACS using a CD34 magnetic cell isolation kit (Miltenyi Biotech, Bergisch-Gladbach, Germany). After two rounds of positive magnetic selection, cell purity obtained was above 99% with a contamination of CD3$^+$ T cells below 0.2%, as evaluated by flow cytometry.

Generation of Human Conventional and SmyleDCs,

The autologous CD34 negative PBMC fraction was used for further positive selection of CD14$^+$ monocytes using CD14 isolation beads (Miltenyi Biotech). For lentiviral gene transfer, monocytes were kept in culture with serum-free Cellgro medium in the presence of recombinant human GM-CSF and IL-4 (50 ng/ml each, Cellgenix, Freiburg, Germany) for 8 h prior to transduction. For generation of SmyleDC, 5×10$^6$ CD14$^+$ monocytes were transduced with 2.5 μg/mL p24 equivalent (multiplicity of infection, M.O.I. of 5) of both ID-LV-G2α and ID-LV-pp65 in the presence of 5 μg/ml protamine sulfate (Valeant, Dusseldorf, Germany). After 16 h transduction, SmyleDC were washed twice with phosphate-buffered saline (PBS) and further maintained in culture with serum-free Cellgro medium. For production of conventional (Cony) DC, monocytes were incubated with ID-LV-pp65 as described above. Following 16 h transduction, LV was removed and cells were further maintained in culture for 7 days in the presence of recombinant human GM-CSF (50 ng/ml), and IFN-α (1000 U/ml, PBL InterferonSource, New Jersey, USA). Cytokines were replenished every 3 days. For mouse immunizations, SmyleDC directly after transduction or ConvDC at day 7 of culture were resuspended in PBS and used for mice injection. Viability, DC immunophenotype and cytokine release were assessed in Smyle or ConvDCs after 7, 14 and 21 days of culture. The number of viable counts was determined by trypan blue exclusion.

Mouse Transplantation with Human HSC

NOD.Cg-Rag1$^{tm1Mom}$ Il2rg$^{tm1Wjl}$(NOD; Rag1$^{-/-}$; IL-2rγ$^{-/-}$, NRG) mice were bred and maintained under pathogen free conditions in an IVC system (BioZone, United Kingdom). All procedures involving mice were reviewed and approved by the Lower Saxony and followed the guidelines provided by the Animal Facility at Hannover Medical School. For HSC transplantation, 4-week old mice were sublethally irradiated (450 cGy) using a $^{137}$Cs column irradiator (Gammacell 3000 Elan, Canada). Mouse recipients were intravenously injected with 5×10$^5$ human CD34$^+$ cells into the tail vein. Mice were bled at different time points (6, 10 and 13) after human HSC transplantation to monitor the status of human hematopoietic cell engraftment and were sacrificed at week 20 for final analyses. DC injections were performed at 10 weeks after HSC transplantation followed by a boost on the week 11. Briefly, Smyle or ConvDC were collected from culture plates, resuspended at a concentration of 5×10$^5$ cells in 100 μL of PBS and subcutaneously injected into the mouse right hind limb using a 27-gauge needle.

Flow Cytometry Analysis

Engraftment of human hematopoietic cells in human HSC-reconstituted mice was evaluated in peripheral blood, spleens and LN using the following mouse anti-human antibodies: PerCP anti-CD45, Alexa700 anti-CD19, Pacific blue (PB) anti-CD4, APC anti-CD3, PE-Cy7 anti-CD8, FITC anti-CD45RA, PE anti-CD62L (Biolegend), PE anti-CD14, FITC anti-Lineage positive, APC anti-CD11c, PE anti-CD123 (Becton Dickinson). For characterization of human B cells subpopulations, the next fluorochrome-conjugated antibodies were used: PB anti-CD45, Brilliant Violet 605 anti-CD19, PE anti-CD27, PE-Cy7 anti-CD38, FITC anti-IgD, Alexa700 anti-IgG, APC anti-IgM, PerCP-Cy5.5 anti-CD24 and APC-C7 anti-CD3. Follicular T helper cells were characterized by staining with PB anti-CD45, Alexa700 anti-CD14/CD19, FITC anti-CD3, APC-C7 anti-CD4, PerCP-Cy5.5 anti-CXCR5, APC anti-PD1 and PE-Cy7 anti-ICOS. For peripheral blood analyses, blood was lysed by two rounds of incubation with erythrocyte lysis buffer (0.83% ammonium chloride/20mMHepes, pH 7.2) for 5 min at room temperature followed by stabilization with cold phosphate buffered saline (PBS) and centrifugation for 5 min at 300g. Cells were incubated with antibodies for 30 min at 4° C. Harvested spleen cells were treated with erythrocyte lysis buffer (0.83% ammonium chloride/20mM-Hepes, pH 7.2) for 5 min, washed with phosphate buffered saline (PBS) and incubated with antibodies for 30 min on ice. After a washing step, cells were resuspended in PBS and acquired in LSR-II or LSR Fortessa flow cytometers (Becton Dickinson). For DC phenotypic characterization the following anti-human antibodies were used: APC anti-CD11c, PE anti-CD14, APC anti-CD3, PE anti-CD80, PerCP anti-HLA-DR, APC anti-CD86, APC anti-CD83 (Becton Dickinson) and FITC anti-CMVpp65 (Pierce Biotechnology, Rockford, Ill.). For DC staining, cells were collected, washed once with PBS and incubated with mouse IgG (50 μg/mL) on ice for 15 min followed by incubation with antibodies. Cells were washed, resuspended in cell fix solution (Becton Dickinson) and further analyzed using a FACSCalibur cytometer. All analyses were performed using FloJo (Tree Star Inc., Ashland, Oreg.) software.

Lymph Node Drainage Analyses

Evaluation of the hind limb lymphatic drainage was adapted from a methodology previously described (Harrell, Iritani et al. 2008). Briefly, mice were subcutaneously injected with 20-30 μL of 5% Evans blue into the right hind limb. After injection dye was allowed to be taken up by lymphatic vessels for 30 min. Mice were euthanized and dissected to locate the inguinal and axillary draining LN and the lymphatic vessels.

Functional Analyses of pp65-CTLs Recovered from Mouse LNs and Spleen

For evaluation of T cell immune responses against CMV-pp65, splenocytes were harvested, stained with APC-conjugated anti-human CD3 and sorted using a XDP cell sorter (Beckman Coulter). Human CD3$^+$ cells were activated by human anti-CD2/CD3/CD28-conjugated magnetic beads (Myltenyi Biotec) in a bead-to-cell ratio of 1:2 and cultured in X-Vivo medium in the presence of 200 ng/mL of human (IL)-2, 5 ng/mL of human IL-7 and 5 ng/mL of IL-15. T cells were further expanded by co-culture with SmyleDC in a DC-T cell ratio of 1:10 for additional 7 days. LN cells were also harvested and directly incubated with SmyleDC as described above. For CMV-specific IFN-γ production, expanded T cells isolated from spleen, LN or PBMC from CMV-reactive healthy donors (20.000 cells) were seeded on an anti-human IFN-γ-coated 96-well ELISPOT plate and incubated overnight in the presence of 10 μg/mL of pp65 overlapping peptide pool (Miltenyi Biotec) or no peptide. Next day, cells were washed and plates were further incubated with biotin-conjugated anti-human IFN-γ antibodies followed by alkaline phosphatase-conjugated streptavidine. Plates were developed using NBT/BCIP liquid substrate and analyzed in an AELVIS ELISPOT reader (AELVIS GmbH, Hannover, Germany).

Histology and Immunohistochemistry Analysis of Human Hematopoietic Cell Engraftment LN from human HSC-reconstituted NRG or C57BL/6 wild type mice were harvested and embedded in optimal cutting temperature compound (O.C.T. Sakura Finetek, Torrance, Calif., USA) for cryopreservation. Frozen sections (5 μm) were fixed by acetone and stained with monoclonal anti-human CD3 (eBioscience, San Diego, Calif., USA), anti-human Pe-Texas Red-conjugated CD8, anti human CD11c (eBioscience), APC anti-human CD19 (eBioscience), anti-mouse LYVE-1 (Dako), anti-mouse CD31 (BD Bioscience). Immunofluorescence analyses were performed in an Axiocam fluorescence microscope (Zeiss) and images created using Axiowert software (Zeiss).

Immunoglobulin Production in HSC-NRG Mice

Plasma was harvested from HSC-NRG mice 20 weeks after reconstitution and screened by ELISA for the presence of total human IgM an total human IgG as described elsewhere (Becker, Legrand et al. 2010). Total IgM and IgG determination was performed by coating 96-well plates either with AffiniPure F(ab')$_2$ fragment goat anti-human IgM (Fc5μ-specific, Jackson ImmunoResearch) or AffiniPure goat anti-human IgG (Fcγ fragment-specific; Jackson ImmunoResearch). Control human serum protein calibrator (Dako) with known IgM (0.8 mg/ml) and IgG (10.4 mg/ml) concentrations was used as a standard to be compared to the samples. After coating, the plates were washed in ELISA wash buffer (PBS, 0.5% Tween-20), blocked with 4% of milk and further incubated with serial dilution of mouse plasma (starting at a dilution of 1:5). Enzyme-conjugated detection antibodies were added at a dilution of 1:2500 for HRP-conjugated anti-IgG and a dilution of 1:5000 for HRP-conjugated anti-IgM (both from Jackson ImmunoResearch). TMB substrate/stop solution (Biosource) was used for the development of the ELISA assay.

Analyses of Human Cytokines:

Detection of human Th1/Th2 cytokines in DC culture supernatants and mouse plasma was performed by fluorescent bead-based 14-plex Luminex assay according to the manufacturer's protocol (Millipore). The 14-plex assay measured the following cytokines GM-CSF, IL-4, TNF-α, IL-6, IL-8, MCP-1, IL-10, IL-1β, IL-5, IL-13, IFN-γ, IL-7, IL-2 and IL-12(p70). Detection of IFN-α in DC supernatants and mouse plasma was performed by commercially available ELISA kit (Mabtech, Minneapolis, USA).

In Vivo Bio-Luminescence Imaging Analyses

Mice were anesthetized with ketamine (100 mg/kg intraperitoneally) and xylazine (10 mg/kg intraperitoneally), and an aqueous solution of d-luciferin (150 mg/kg intraperitoneally) was injected 5 minutes before imaging. Mice were placed into a dark chamber of the charge-coupled device camera (IVIS 200, Xenogen, Cranbury, N.J., USA), and grayscale body surface reference images (digital photograph) were taken under weak illumination. After the light source was switched off, photons emitted from luciferase-expressing cells within the animal body and transmitted through the tissue were quantified over a defined time of up to 5 minutes using the software program Living Image (Xenogen) as an overlay on Igor (Wavemetrics, Seattle, Wash., USA). For anatomical localization, a pseudocolor image representing light intensity (blue, least intense; red, most intense) was generated in Living Image and superimposed over the grayscale reference image. Quantified luminescence consists in averaged photon radiance on the surface of the animal and is expressed as photons/sec/cm$^2$/sr where sr=steradian.

Real-time PCR for Analyses of Lentiviral Copies in Tissues

Total genomic DNA was extracted from the spleen and lymph nodes (left and right flanks) using the QiaAmp DNA blood mini kit (Qiagen, Hilden, Germany) according to the manufacturer's instructions. Vector derived copy numbers were determined by Quantitative real-time PCR as previously described (Maetzig T et al., 2010 and Rothe M, et al., 2012). 100 ng/2 μL of genomic DNA prepared from the above step was added to 13 μL of RQ-PCR mix containing 7.5 μL of SYBRTaq mix with 1 μL of primer mix for wPRE (Woodchuck Hepatitis Virus post transcriptional regulatory element; wPRE forward: 5'-GAGGAGTTGTGGCCCGT-TGT (SEQ ID NO: 9), wPRE reverse: 5'-TGACAGGTG-GTGGCAATGCC (SEQ ID NO: 10) or PTBP2 (polypyrimidine tract binding protein 2); PTBP2 forward: 5'-TCTCCATTCCCTATGTTCATGC (SEQ ID NO: 11), PTBP2 reverse: 5-GTTCCCGCAGAATGGTGAGGTG (SEQ ID NO: 12) adjusting the volume to 13 μL with PCR grade, nuclease free water. A plasmid vector (pCR4-TOPO, kindly provided by Michael Rothe, Department of Experimental Hematology, Hannover Medical School) containing these two amplicons was used for standard curves, with known dilutions covering 4-logs. All samples were analyzed with StepOnePlus Real time PCR system (Applied Biosystems). The cycling conditions were 10 min at 95° C., 40 cycles of 15 s at 95° C., 20 s at 56° C. and 30 s at 65° C. Results were quantified by making use of primer pair-specific real-time PCR efficiencies and by comparing sample $C_T$ values to a standard curve generated with the plasmid vector (pCR4-TOPO). Data were analyzed by StepOnePlus software (Applied Biosystems).

Histological Analyses of GVHD

Representative samples from skin and intestine were harvested and routinely formalin fixed and paraffin embedded. 2 μm sections were cut from the blocks and stained for HE. An experienced hematopathologist reviewed the slides blinded to the treatment group of the animals. A semiquantitative score (modified after Lerner K G et al. Transplant Proc 1974 6:367-371) was used to score the histological changes. GVHD Grade 1 is defined by single or multiple apoptotic figures without architectural changes. Grade 2 shows multiple apoptotic figures and drop out of crypts or skin appendages. Grade 3 shows additionally surface necrosis and severe loss of crypts or skin appendages.

Statistical Analysis

Parametric (t test) and non-parametric (Kruskall-Wallis) statistical analyses were performed to compare the differences among groups for engraftment of human hematopoietic lineages in NRG mice. Analyses were performed in Graph prism 5$^{th}$ version software. All tests were two-sided, and P<0.05 was considered significant.

Results

SmyleDC Generation and Characterization In Vitro

Figure 10A:
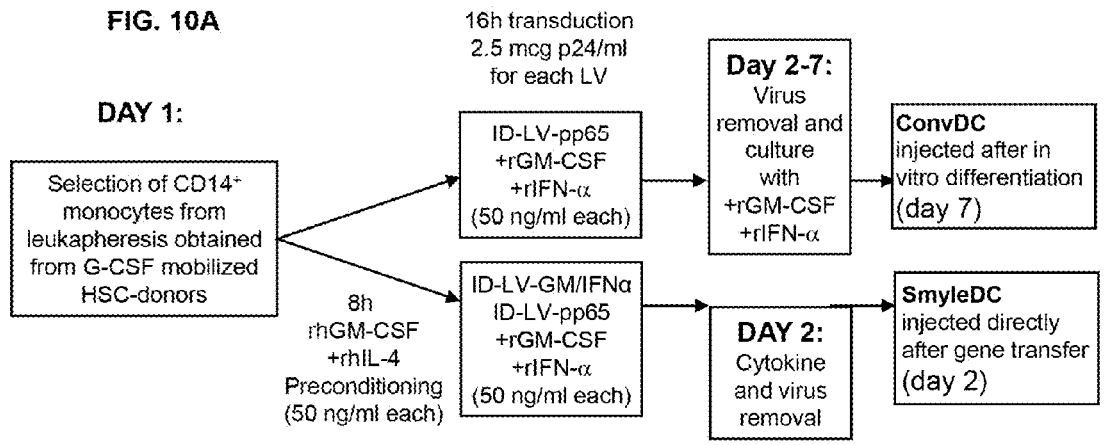
FIGS. 10A-10C: (A) Scheme of production of ConvDC and SmyleDC from monocytes obtained from G-CSF mobilized CD34+ stem cell donors. In this study, both types of DCs are co-transduced with a lentiviral vector for expression of the pp65 antigen. (B) Schedule of human hematopoieitic stem cell transplantation into NRG mice, immunization and analyses. (C) procedures for analyses of human T cell responses against pp65 generated in immunized NRG mice.
Figure 10B:
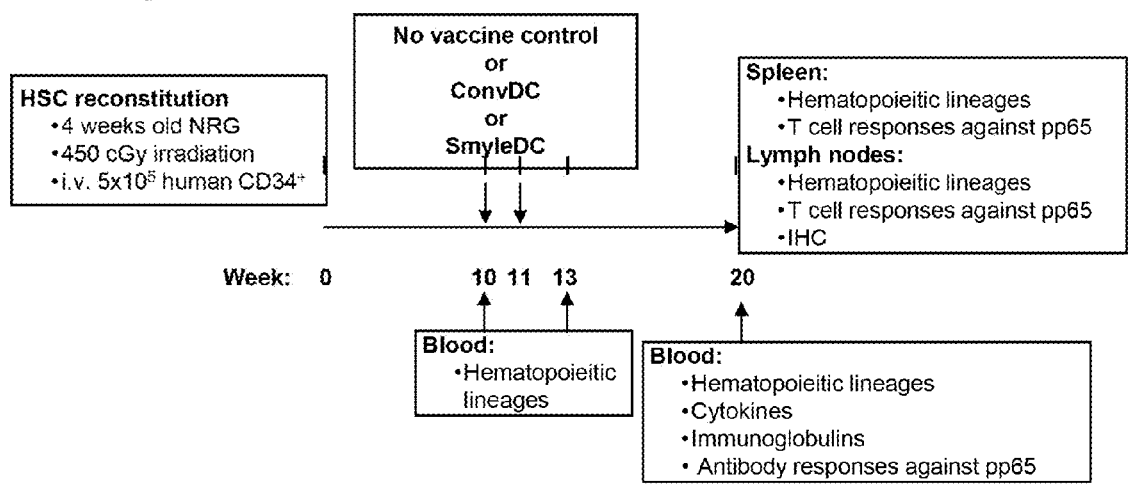
Figure 10C:
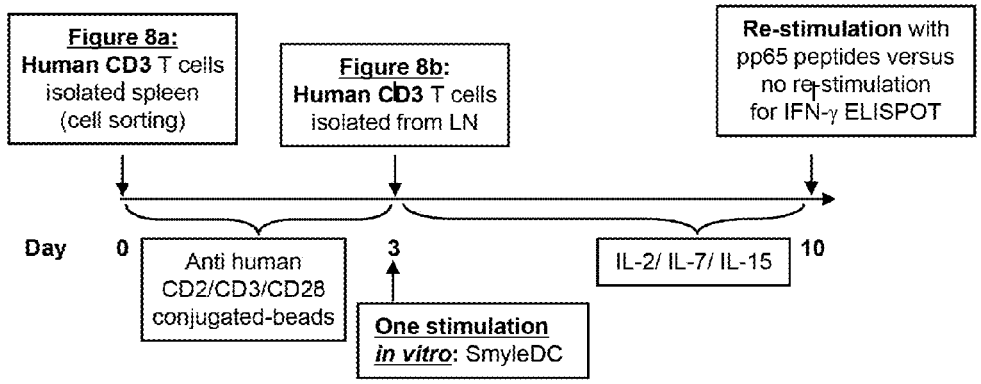
Figure 11A:
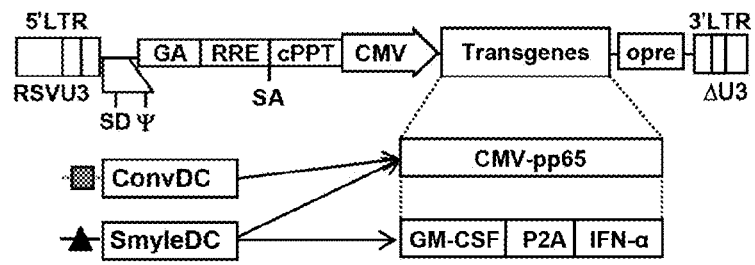
FIGS. 11A-11G: Generation and analyses of human conventional (ConvDC) and SmyleDC from GCSF-mobilized donors. (A) The monocistronic integrase-defective LV encoding for CMV-pp65 protein LV-CMV-pp65 alone was used to generate ConvDC, whereas LV-CMV-pp65 plus the bicistronic LV vector encoding human GM-CSF and human IFN-α were used to co-transduce monocytes and generate SmyleDC. (B) Human GM-CSF and IFN-α production were measured weekly in supernatants from SmyleDC kept in culture up to 21 days. (C) Cell viability of ConvDC and SmyleDC represented by the percentage of viable cells recovered weekly for up to 21 days. (D) Expression of CMV-pp65, (E) CD14 and (F) stability of DC differentiation in DC cultures (measured by expression of CD11c, HLA-DR, CD86, CD83 and CD80) were assessed weekly by flow cytometry. (G) Cell supernatants obtained weekly from ConvDC and SmyleDC were analyzed by cytokine bead array of DC1, DC2 and chemokines Data represent the average of at least three independent experiments from at least three different donors. *p<0.05.
Figure 11B:
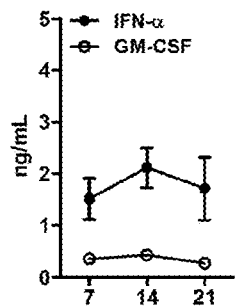
Figure 11C:
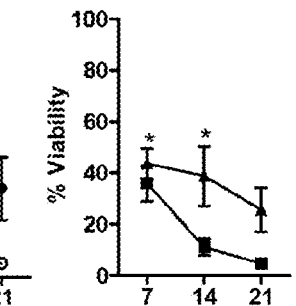
Figure 11D:
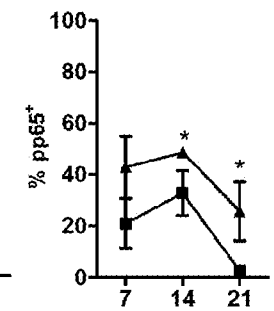
Figure 11E:
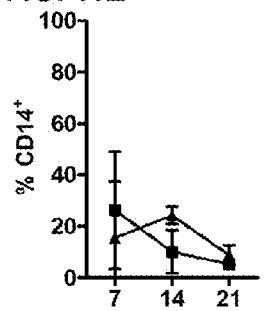
Figure 11F:
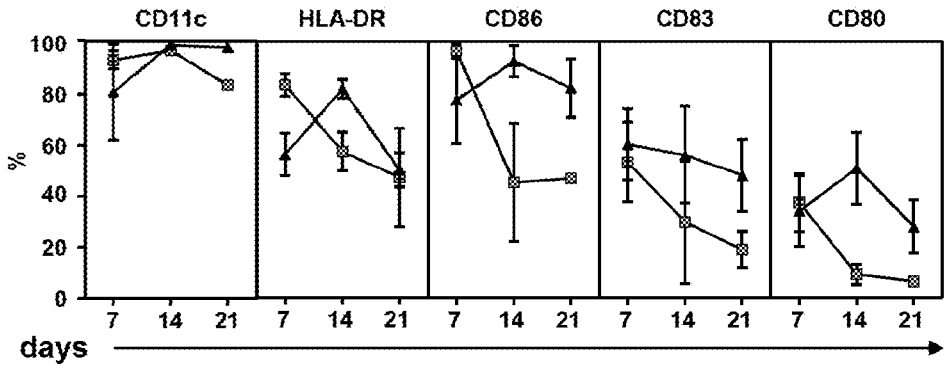
Figure 11G:
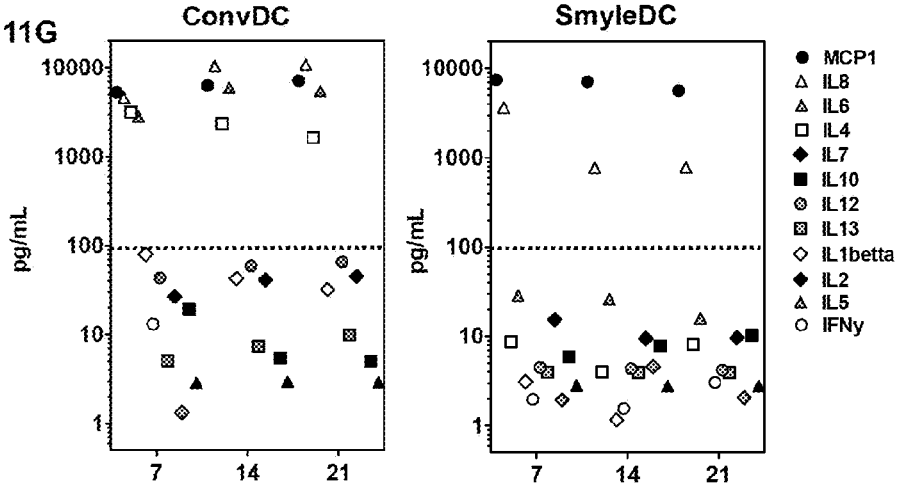

Gene transfer of huGM-CSF, huIFN-α and the CMV-pp65 viral antigen into human monocytes using ID-LV generated long-lasting SmyleDC in vitro and in vivo (Daenthanasanmak, Salguero et al. 2012). Under these conditions, using the green fluorescent protein (GFP) as a quantitative gene reporter, we observed between 10-50% transduction efficiency. We adapted our protocol to generate DC from the CD34$^-$ fraction recovered from PBMC obtained from G-CSF-mobilized HSC donors (FIG. 10). Control ConvDC were produced by transduction of monocytes with an ID-LV vector expressing pp65 (FIG. 11A) and maintained in culture in the presence of recombinant huGM-CSF/huIFN-α. For SmyleDC generation, monocytes were in addition co-transduced with the bicistronic ID-LV expressing huGM-CSF/huIFN-α transgenes (FIG. 11A) and maintained in the absence of cytokines Levels of accumulated human IFN-α (2.0 ng/mL) and GM-CSF (0.3 ng/mL) were detected in continuous culture of SmyleDC for up to 21 days (FIG. 11B). Compared to ConvDC, SmyleDC cultures displayed significantly higher cell viability (day 7, 45 vs. 36%, p>0.05; day 14, 35 vs. 14% p=0.021; day 21 17 vs. 5%, p<0.05, FIG. 11C) and intracellular pp65 expression (peak at 14 day, 55 vs. 21%, p=0.014, FIG. 11D). Although we have not validated pp65 as a quantitative gene reporter in DC, this data correlates with our experience using GFP as a marking gene. After 21 days of culture, both DC types lost expression of the monocytic marker CD14+ (FIG. 11E), whereas DC surface markers CD11c, HLA-DR, CD86, CD83 and CD80 were persistently expressed on SmyleDC (FIG. 11F). Analyses of cytokines secreted by ConvDC and SmyleDC revealed high stable production of the chemo-attractant proteins MCP-1 and IL-8 at ng/ml levels (FIG. 11G). ConvDC also secreted high levels of the DC2-type interleukins IL-6 and IL-4. Several other cytokines were detectable for both cultures at lower pg/ml concentrations (IL-7, IL-10, IL-12, IL-13, IL-1β, IL-2, IL-5 and IFN-γ) indicating a mixed DC1- and DC2-type cytokine pattern.

Figure 12:
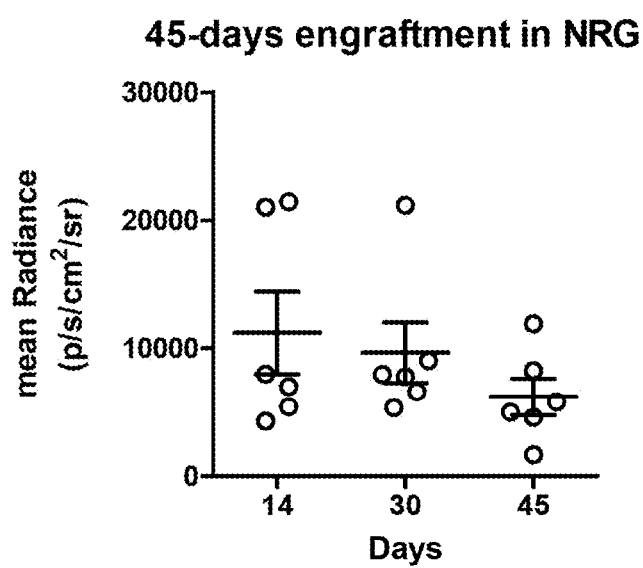
FIG. 12: SmyleDC produced with additional co-transduction with a lentiviral vector expressing the firefly luciferase were injected on the day after transduction subcutaneously into NRG mice. Mice (n=6) were administered intraperitonealy with Luciferin and optical imaging analyses were conducted for localization of the bioluminescence signal. Bioluminescence detected in the region of interest was measured for days 14, 30 and 45 after SmyleDC/luciferase administration and was plotted for each mouse.

NRG Mice Immunization with SmyleDC/fLuc and Analyzed by Optical Imaging Show High Viability In Vivo Day 2 SmyleDC labelled with a lentiviral vector expressing firefly luciferase were injected s.c. into NRG mice (n=7) and the bioluminescence signal was measured non-invasively on days 14, 30 and 45 post-injection. All mice showed detectable bioluminescence signals on the injection site until 45 days (FIG. 12)

Transplantation of Human CD34+ Cells into NRG Followed by SmyleDC Immunization Results in Increased T Cell Expansion We transferred adult human CD34+ HSC that were positively selected twice and highly pure (>99%) into sublethally irradiated four-week-old NRG mice. Ten weeks after CD34+ cell transplantation, human hematopoietic reconstitution reached plateau and became stable (2-5% of PBMC corresponding to human CD45+ cells). We did not observe statistically significant differences in the frequency human CD45+ in PBL in the different study arms prior to DC immunization (data not shown). Thus, the mice were allocated to the different immunization groups at random after HCT, receiving prime-boost immunizations of DC produced with monocytes of the same HCT donor ($5 \times 10^5$ cells) by s.c. injections into the right hind flank (FIG. 10B). We compared the long-term (20 weeks) hematopoietic and immune reconstitution of non-immunized versus mice immunized with ConvDC and SmyleDC produced with monocytes from the same CD34+ donor. Ten weeks after SmyleDC immunization, >10 pg/ml levels of human GM-CSF, IL-5, MCP-1 and IFN-γ and lower levels of several other human factors (IL-12, IL-1β, IL-6, IL-10, IL-8, IL-4, IL-13) were detectable in plasma, indicating a persisting effect of SmyleDC immunization (FIG. 13A). At this time-point, levels of human cytokines in plasma of mice immunized with ConvDC and controls were dramatically lower. At the 20-week endpoint, we did not observe significant differences in the frequency of human CD45+, B (CD19+) and T cells (CD3+) between the control and ConvDC groups (FIG. 13B). However, the frequency of human CD45+ cells was significantly higher for SmyleDC-immunized mice. Notably, analyzing the content of human CD45+ cells, the relative frequency of human T cells was significantly elevated (to 50%) upon SmyleDC vaccination, whereas the relative frequency of human B cells (defined as CD19+) was significantly decreased (to 30% in SmyleDC) (FIG. 13C-D, Table 1). In fact, even one week after SmyleDC prime/boost immunization (week 13 after HCT) the rise in T cell expansion was already significant. At week 20 post-HCT, CD3+CD4+ helper T cells represented the most frequent T cell population (average 30%) of mice immunized with SmyleDC and CD3+CD8+ cytotoxic T lymphocytes (CTLs) were clearly detectable (average 20% of human T cells in PBL) (FIG. 13E-F, Table 1).

Regeneration of Lymph Nodes and Lymphatic Flow after SmyleDC Immunization

One of the most striking findings upon post-mortem analysis came from the examination of the peripheral lymph nodes in mice immunized with SmyleDC: LN were clearly visible at the inguinal, and axillary regions (FIG. 14A). It has long been known that NRG mice lacking the expression of the common cytokine receptor γ chain display a defective lymphoid development and inactive LN follicles (Cao, Shores et al. 1995) and even after human HCT, the regeneration of peripheral LN is not rescued and LN are mostly small or not identifiable at necropsy. Mice immunized with SmyleDC showed conspicuous active axillary and inguinal LN in up to 90% and 70% of the cohorts, respectively. ConvDC immunization resulted in less frequent axillary (66%) and inguinal (33%) LN (FIG. 14B). Remarkably, there was a strong correlation between the SmyleDC immunization at the right side and the formation of LN at the same side of the corresponding lymphatic draining axis. In order to confirm a functional lymphatic drainage from the lower trunk (inguinal LN) to the upper trunk (distal axillary draining LN) at 20 weeks after HCT, we injected 5% Evans blue subcutaneously in NRG mice near the SmyleDC immunization site. The ink stained the draining inguinal LN adjacent to the injection site and the blue signal migrated through the lymphatic vessels to the distal axillary LN. Immune competent C57BL/6 mice with a normal lymphatic system showed a similar ink drainage pattern, whereas non-immunized mice or mice immunized with ConvDC showed impaired drainage (data not shown).

Regenerated Lymph Nodes Contain Human T and B Cells at Different Stages of Differentiation Immunohistological analyses of LN explanted from SmyleDC-immunized mice revealed a massive infiltration of lymphocytes but only a few regions resembling the anatomy of germinal centers observed in normally developed LN obtained from wild type C57BL/6 mice (data not shown). Immunofluorescence analyses showed a predominant repopulation with human CD3+ T cells (data not shown). Human CD11c+ DCs were detected in the cortex or co-localizing with mouse lymphatic endothelial cells (LYVE-1). We also detected vessel structures positive for mouse endothelial CD31 marker (most likely high endothelial venules). Flow cytometry analyses of LN revealed human CD45+ cells (77%), CD3+ T lymphocytes (73%) and only 3.8% CD19+ B cells (FIG. 14C). Within human CD3+ cells, 56% were CD4+ and 42% were CD8+ (FIG. 14D). Remarkably for both T cell subsets, we observed approximately 80% CD45RA−CD62L− effector memory cells, 10-20% central memory cells, and fewer than 5% naïve T cells (FIG. 14E-F). In order to identify follicular T helper cells (Tfh), LN explanted from SmyleDC-immunized mice were pooled and analyzed for CD4+CXCR5+$^{hi}$PD-1+ICOS+ cells, which corresponded to 4.2% of the CD3+ population (FIG. 14G). A human tonsil showed a Tfh cell frequency of approximately 8% (FIG. 14G). We also examined B cell subpopulations in pooled-LN and compared it with a human tonsil (data not shown). CD24$^{hi}$CD38$^{hi}$ transitional B cells corresponded to a minor population of total CD19+ cells in humanized LN (0.4%) and tonsil (2.4%) (FIG. 14H). Naïve B cells (IgD+CD24$^{int}$CD38$^{int}$) were less frequent in humanized LN than in tonsil (5.9% vs. 43.9%). Surprisingly, we found dramatically higher frequencies of CD27$^{hi}$CD38$^{hi}$ terminally differentiated plasmablasts in humanized LN as compared with tonsil (49.1% vs. 0.7%) (FIG. 14H).

SmyleDC Migrate to Adjacent and Distal LN

Figure 15:
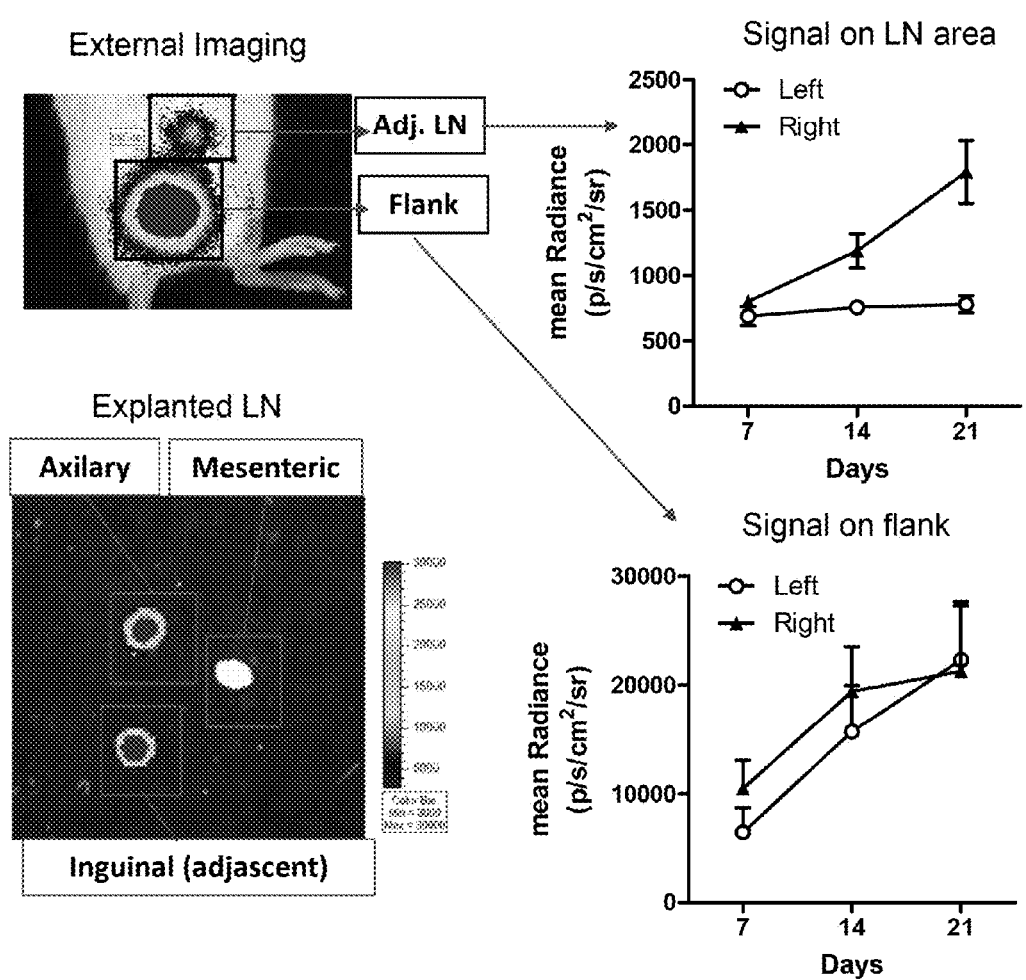
FIG. 15: Migration of SmyleDC/luciferase to adjacent and contra-lateral lymph nodes. NRG mice transplanted with human $CD34^+$ cells and immunized with SmyleDC (weeks 10, 11) were subsequently (on week 20) administered with SmyleDC/luciferase.

Non-invasive optical imaging analyses of the injection site from SmyleDC-immunized mice subsequently injected with SmyleDC marked with the luciferase gene revealed migration of the bioluminescence emitting cells to the region of the adjacent inguinal LN (FIG. 15). The bioluminescence signal in the injection site and in the LN area increased from days 7 to 21 after injection. Local and distal LN explanted 21 days after SmyleDC/LUC injection showed bioluminescence signal. The data demonstrates that SmyleDC can migrate in the immune regenerated HIS-NRG mice to local and distal LN. Corroborating with these results, human myeloid and plasmacytoid DCs were detectable at higher absolute cell counts in mice immunized with SmyleDC than in ConvDC and controls (FIG. 16). This potentially indicates paracrine effects of SmyleDC in LN to stimulate endogenously regenerated DC precursors to differentiate in DCs in LN. In addition, sensitive Real-time PCR analyses of LN adjacent to the SmyleDC injection site showed detectable copies of lentiviral vector (0.78+/−0.43 copies per cell). LV copies were also detectable in LN contralateral to the immunization side (0.05+/−0.04 copies per cell) and in spleen (0.58+/−0.49 copies/cell) confirmed the systemic migration of SmyleDC to lymphatic organs.

Increased Absolute Numbers of Human Mature T and B Cells can be Detected in Spleen of SmyleDC Immunized Mice Twenty weeks post-HCT, SmyleDC-immunized mice showed more than 100-fold increase in the absolute numbers of human $CD3^+$ T cells (858,487) in the spleen in comparison with non-immunized mice (p=0.0028) (FIG. 17A). Mice immunized with ConvDC (6,394 cells/spleen, 132 fold less, p=0.02 vs. SmyleDC) and control mice (4,459 cells/spleen, 192 fold less, p=0.0007 vs. SmyleDC) failed to support high levels of expansion/homing of $CD3^+$ cells to the spleen (Table 1). In contrast to the lower relative frequency previously assessed in peripheral blood, the absolute $CD19^+$ B lymphocyte content in spleens was significantly higher in SmyleDC-immunized mice (406,672 cells/spleen) than in ConvDC-immunized (82,065 cells/spleen, 5 fold lower, p=0.37) and control mice (15,639 cells/spleen, 26 fold lower, p=0.0034). Histologically, human T and B cells were found interacting within clusters resembling follicles (data not shown). The composition of T lymphocyte subsets was further analyzed. Average numbers of Th and CTL cells in spleens of SmyleDC mice were 370,086 and 81,649 cells/spleen respectively (FIG. 17B-C). This was significantly higher than the numbers found after ConvDC immunization (13,976 and 7,937 cells/spleen, p=0.0046 and 0.038 vs. SmyleDC, respectively) or in non-immunized controls (1,943 for $CD4^+$, p=0.0035 and 52 for $CD8^+$, p=0.021 vs. SmyleDC). Both naïve and effector T helper and CTL were increased in terms of absolute cell numbers (FIG. 17B-C). Follicular T cells, which are rarely observed in spleens of HIS-NRG mice, were detectable at 9,425 Tfh cells/spleen on average after SmyleDC immunization (compared with only 12 cells/spleen in the control group (p=0.0023), and no detectable Tfh population in ConvDC group (FIG. 17D).

Detailed analysis of B cell subpopulations in spleen revealed not significant differences in numbers of transitional B cell (control 6,732, ConvDC 29,028 and SmyleDC 77,454 cells/spleen) (FIG. 17E). However, SmyleDC-immunization led to a significant marked expansion of mature B cells (83,454 cells/spleen) and plasmablasts/plasma cells (91,522 cells/spleen) compared to other groups.

SmyleDC Immunization Induces Anti-pp65 T Cell Immune Responses

Figure 18A:
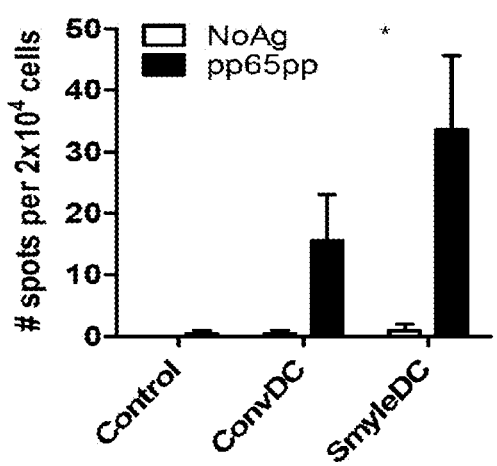
Figure 18B:
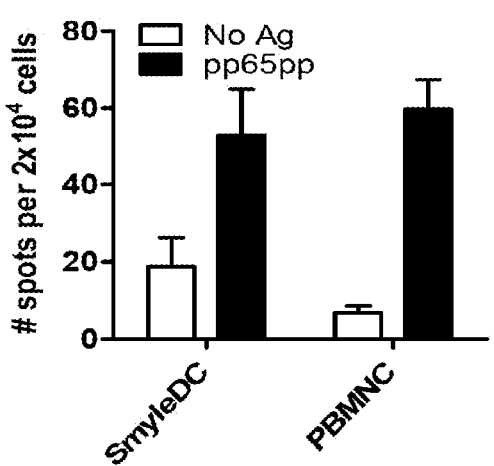

We showed previously that immunization of NRG mice with SmyleDC prior adoptive huPBL/T cell transfer enhanced anti-pp65 specific T responses in vivo (Daenthanasanmak, Salguero et al. 2012). Here, we evaluated whether SmyleDC could stimulate endogenously developed human T cells post-HCT reactive against pp65. Human $CD3^+$ cells were FACS-sorted from spleen or LN 20 weeks after HCT. In order to obtain enough T cell numbers for conducting the immune assays, T cells from spleens were expanded for 3 days in the presence of anti CD2/CD3/CD28-conjugated beads and further co-cultured for 7 days with SmyleDC plus cytokines (IL-2, IL-7, IL-15) (FIG. 10C). T cells were seeded on IFN-γ-coated plates overnight in the absence of antigenic stimulation (NoAg) or with a pp65 overlapping peptide pool (pp65pp) and analyzed by IFN-γ-ELISPOT. Splenocytes from SmyleDC-immunized mice showed higher frequency of pp65-reactive T cells than ConvDC-immunized mice (33.6 spots vs. 15.5 spots on average for triplicates, p=0.25) or control mice (less than 1 spot, p<0.05) (FIG. 18A). T cells isolated from individual LN from SmyleDC-immunized mice (n=4) and cultured for 7 days with SmyleDC plus cytokines also reacted against pp65 peptides (pp65: 53 spots vs. no antigen: 18.7 spots, p=0.021). PBMC from CMV-reactive donors were used as positive control for the assay (FIG. 18B).

SmyleDC Immunization Induces Immunoglobulin and pp65-Specific Humoral Responses

Figure 18C:
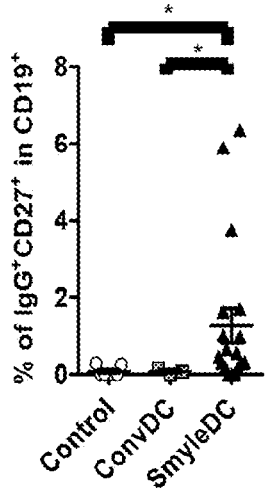
Figure 18D:
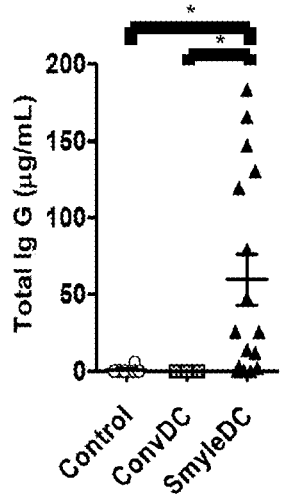
Figure 18E:
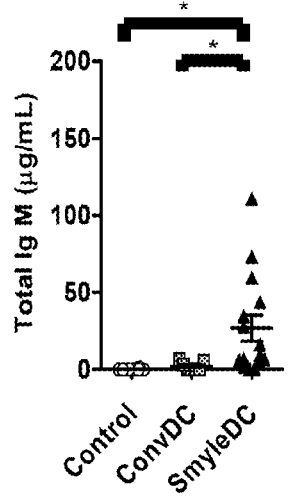
Figure 18F:
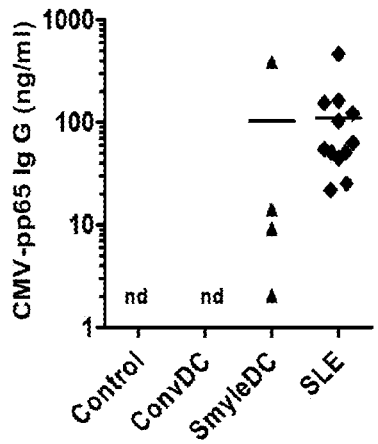
Figure 18G:
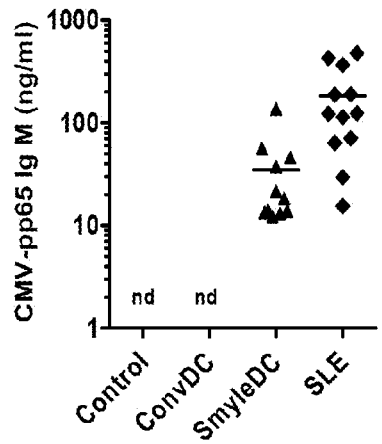

We observed significant increase in the frequency of IgG memory B cells in spleens as well as generation of plasma IgM and IgG upon SmyleDC immunization in comparison with control groups, where immunoglobulin levels were close to limit of detection (FIG. 18C-E). Ig reactivity specific against pp65 was assessed using plasma obtained from CMV seropositive systemic lupus erythematosus (SLE) patients as positive controls for an in house developed ELISA system. Whereas there was no detectable signal in plasma from ConvDC-immunized or control mice, anti-pp65 IgG and IgM were found in plasma of 4/22 and 11/22 mice, respectively (FIG. 18F-G). Remarkably, despite these functional antigen-specific human T and B cell responses, we did not detect any signs of GVHD in these mice as evaluated by weight monitoring from weeks 6 to 20 after HCT (FIG. 19A). A cohort of 10 mice immunized with SmyleDC was maintained for 40 weeks after HCT and we did not observe clinical signs of late-onset GVHD or any macroscopic clinical signs of disease. Nevertheless, we analyzed some mice (n=4) histopathologically by H&E staining and light microscopy for signs of GVHD in tissues commonly affected, i.e. skin and intestines. We observed only mild grade 1 GVHD in skin for 2 out 4 mice and in intestine of 3 out of 4 mice corresponding to detection of apoptotic bodies (FIG. 19 B-C).

Detection of SmyleDC in Tissues of Mice by PCR.

A quantitative real time PCR method for detection of the WPRE element in the lentiviral vector was used using as a standard control a 293T cells line containing 3 copies of integrated LV sequences. Analyses of SmyleDC resulted in 7.5 copies of vector per cell. Analyses of spleen collected from NRG mice (n=4) transplanted with human $CD34^+$ cells and immunized with SmyleDC showed 0.58+/−0.49 copies per cell. Analyses of LN collected from NRG mice (n=4) transplanted with human $CD34^+$ cells and immunized with SmyleDC showed 0.78+/−0.43 copies per cell for the adjacent LN and 0.052+/−0.041 copies per cell for the contralateral LN. The data confirms the migratory capacity of SmyleDC injected on the skin to local and distal LN and to the spleen (Table 2).

Discussion

This preclinical validation study to demonstrate efficacy of SmyleDC in the human HCT setting using the HIS-NRG model exceeded our expectations, as a full range of T and B cell terminal adaptive immune reconstitution effects including the development of peripheral lymph nodes were observed. Both ConvDC and SmyleDC could be produced with monocytes isolated from the G-CSF mobilized HCT donors. SmyleDC showed higher viability in vitro and persistent autocrine activation for expression of relevant immunologic cell surface markers and cytokines than ConvDC. Subcutaneous administration of SmyleDC ten weeks post-HCT and plasma analyses another 10 weeks later revealed substantially higher levels of several human cytokines (GM-CSF, IL-5, MCP-1, IFN-γ, IL-13, TNF-α, IL-8, IL-4) than in ConvDC-immunized or control mice. This was associated with significantly higher frequencies of human T cells, higher absolute numbers of effector memory T cells and detection of terminally differentiated plasma B cells in blood, spleen and LN. Immune monitoring 20 weeks after HCT showed that these cellular effects were accompanied with pp65-specific T cell and antibody responses. Taken the data together, although immunization with ConvDC expressing pp65 showed some degree of immune modulation in comparison to non-immunized mice, the effects of SmyleDC were clearly more profound. These differences highlight the requirement of cell therapies involving post-mitotic and non-replicating antigen presenting cells to persist long enough after administration in order to efficiently signal, produce cytokines and chemokines, migrate, attract and interact with other cells of the immune system for robust antigen presentation.

These new in vivo findings in NRG mice also can lead to novel advances to improve the generation of humanized mice with a functional immune system. Although several transgenic and vaccination approaches to induce immune reconstitution in immunodeficient mice have been evaluated over the past decade, suitable in vivo experimental models to address human hematopoietic development to terminally and functionally differentiated T and B cells were lacking. In order to experimentally recapitulate human immune reconstitution after HCT in vivo, Schultz, Ishikawa and colleagues pioneered the transplantation of CD34$^+$ HSC into different types of immunodeficient mouse strains lacking the common interleukin-2 receptor gamma chain (IL2Rγ) (NOD/Rag1null/IL2Rγ$^{null}$-NRG, NOD/LtSz-scid/IL2Rγ$^{null}$-NSG, or NOD/SCID/IL2Rγ$^{null}$-NOG) resulting in reconstitution of human hematopoietic lineages 8 to 10 weeks after CD34$^+$ cell transfer (Ishikawa, Yasukawa et al. 2005; Shultz, Brehm et al. 2012). However, regardless of the source of HSC and the method for cell transplantation, humanized mice displayed suboptimal levels of lymphocyte reconstitution, lack or low levels of antigen specific cellular and humoral responses and overall anergy (Lepus, Gibson et al. 2009; Andre, Erbacher et al. 2010). Factors that may impact in the inefficient lymphatic development in HIS mice include the absence of human histocompatibility molecules and a poor humanized cytokine environment. To overcome this deficiency, approaches including delivery of recombinant cytokines (Chen, Khoury et al. 2009; O'Connell, Balazs et al. 2010), transplantation of fetal lymphatic tissue along with HPCs (Biswas, Chang et al. 2011; Hu and Yang 2012) or the use of transgenic strains constitutively expressing the major histocompatibility molecules (MHC) class I (Shultz, Saito et al. 2010) and II (Danner, Chaudhari et al. 2011) or critical hematopoietic cytokines (Willinger, Rongvaux et al. 2011) have been recently described. Despite some improvement, these strategies allowed a limited improvement in B and T cell responses against human viral challenges. As consistent with previous reports regarding HCT transplantation with G-CSF-mobilized adult hematopoietic stem cells, we observed low relative frequencies of T lymphocytes in non-immunized control mice (i.e., lower than 20%) which reflected also the results obtained with ConvDC-immunization. Conversely, as also reported, the relative frequency of circulating human B cells (here defined as CD19$^+$ cells) was commonly higher than 80% in control mice. SmyleDC/pp65 immunization resulted into a decrease of the relative B cell frequency in PBL, but was associated with an increase of the absolute B cell content in spleens and lymph nodes. Notably, the higher repopulation rate of T and B cells in these tissues, was correlated with matured phenotypes associated with immune activation. Importantly, few reports have described the presence of reconstituted lymphatic structures in HSC-transplanted mice (Sun, Denton et al. 2007; Marodon, Desjardins et al. 2009; Singh, et al. 2012).

Although human CD34$^+$ HCT can be improved by using human cord blood or fetal liver, thereby reaching higher rates of human cell engraftment (>60%) than in our studies (using G-CSF-mobilized adult blood), reported LN structures were anecdotal or required very long periods for observation (Lang, Kelly et al. 2013). These data implicates that functional and long-lasting DC may be required after HCT for regeneration of peripheral lymph node and lymphatic flow in order to activate, mobilize, and finally mature lymphocytes towards full immune function in humanized mice. Thus, accelerating the presence of functional DC concomitantly with LN and lymphatic development in humanized mouse models may be a "conditio sine qua non" for using these models for predictive studies of adaptive immunity. Although early T cell development was not the focus of our efficacy studies, we predict that the higher absolute naïve and memory/effector T cell counts found in spleen reflect a bona fide higher thymopoiesis in these humanized mice. Ultimately, this novel modality of "human endogenously regenerated systemic lymph node" ("HERS-LN") will allow in the future more detailed mechanistic in vivo studies of the development of the human immune system, antigenic presentation, T and B cell terminal activation and useful interpretation of pre-clinical testing of HCT protocols, vaccines and immunomodulatory molecules.

Safety evaluation, up-scaling and clinical development of lentivirus-induced DC generated with single tricistronic lentiviral vectors for cancer immunotherapy is an ongoing task in our group (Pincha, Sundarasetty et al. 2012; Sundarasetty, Singh et al. 2013). Production of SmyleDC co-expressing pp65 with a single tricistronic lentiviral vector is ongoing for translation into clinical trials to immunize transplanted patients receiving stem cell grafts from CMV-seronegative donors or cord blood (Daenthasanmak, Salguero et al, in "Example 3"). In addition, SmyleDC/pp65 could be also explored in the future as an autologous cellular immuno therapeutic product against glioma and breast cancer, as HCMV has been recently implicated as viral target for these types of cancer.

Example 3

Aim of the Experiment

In this current study, we validated SmyleDC/pp65 generated with a preclinical single tricistronic integrase-defective lentiviral vector in vivo using two fully humanized mouse HCT models. We tested several efficacy and safety parameters and established proof of potency in irradiated NRG mice transplanted with human CD34$^+$ stem cells (G-CSF mobilized adult HSC in comparison with neonatal UCB). We demonstrated in these predictive humanized HCT mouse models the adaptive immune effects of SmyleDC/pp65 to promote expansion of endogenously developed cytotoxic T cells and humoral immune reactivity against the HCMV pp65 antigen.

Results

Figure 21A:
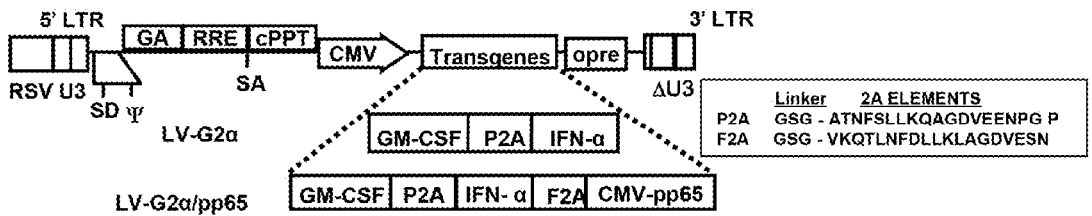
Figure 21B:
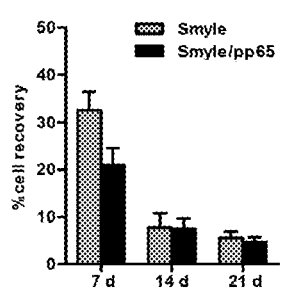
Figure 21C:
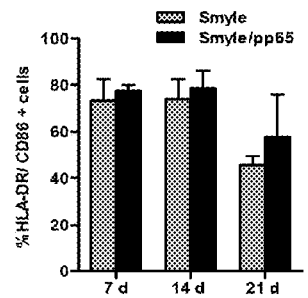
Figure 21D:
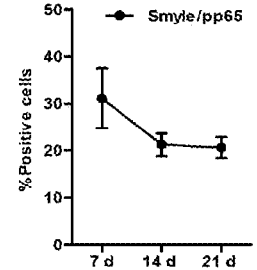
Figure 21E:
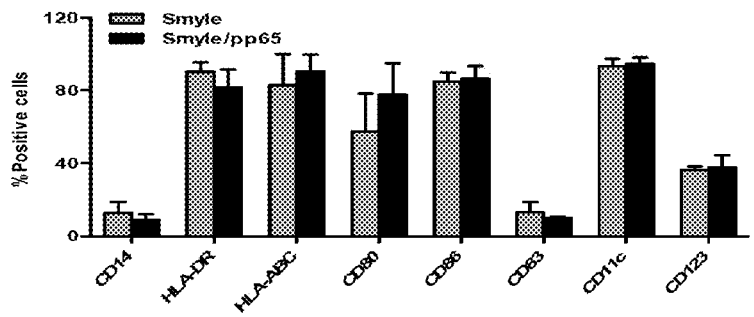
Figure 21F:
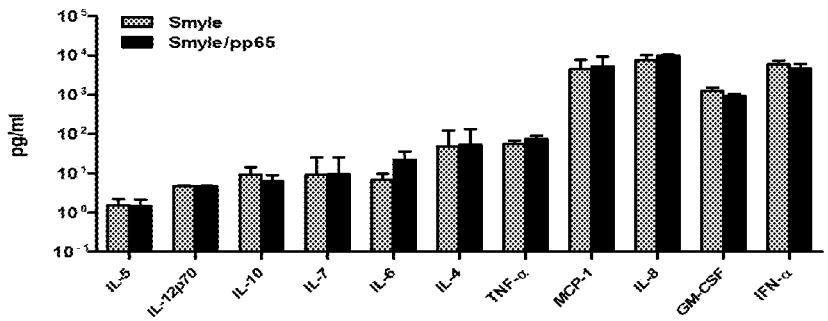

Effects of Tricistronic Vector on Dendritic Cell Recovery, Viability and Identity The tricistronic self-inactivating lentiviral vector ID-LV-G2αpp65 (FIG. 21A) was designed with heterologous interspaced 2A elements (P2A derived from porcine teschovirus and F2A from foot and mouth disease virus). Large-scale batches of third generation integrase defective lentivirus pseudotyped with the vesicular stomatitis-G protein (VSV-G) were produced as described (Daenthanasanmak et al., 2012). Viral titers were determined by measuring concentration of the p24 capsid protein, resulting in titers in the normal range (tricistronic: 7 µg/ml, n=10; bicistronic: 9.4 µg/ml, n=10). The expression of the all the transgenes GM-CSF, IFN-α and pp65 in transduced 293T cells were confirmed by analyses of lysates and cell supernatants by western blot and immune detection. GM-CSF and IFN-α proteins were primarily secreted and detectable in the cell supernatants. Western blot analyses indicated exclusive intracellular expression of the pp65 protein, which was confirmed by intracellular staining and flow cytometry analyses. Overnight exposure of monocytes obtained from healthy donors with the ID-LV-G2αpp65 vector at a multiplicity of infection (MOI) of 5 and subsequent ex vivo culture in the absence of recombinant cytokines for seven days resulted on average in a recovery of 20% of the monocytes used for transduction (compared to 32% for the control bicistronic vector). We observed a dose effect of MOI on cell recovery, and MOI=5 produced the most consistent cell recoveries (data not shown). For transduction with bicistronic and tricistronic vectors, the number of viable cells comparably decreased upon further culture (relative to input 8% for day 14 and 5% for day 21), demonstrating no toxic or transforming effects of pp65 when provided in one vector in cis with the differentiation cytokines (FIG. 21b). Stability of immunophenotypic markers (HLA-DR$^+$/CD86$^+$) and detectable levels of intracellular pp65 expression in SmyleDC/pp65 were analyzed for up to 21 days of ex vivo culture period, as the cells eventually senesced and died after about one month of culture (FIG. 21c, d). Additional detailed analyses on day 7 of DC cultures of a panel of immunophenotypic DC markers typical of activated monocyte-derived DCs (high frequencies of HLA-DR$^+$, HLA-ABC$^+$, CD11c$^+$, CD80$^+$, CD86$^+$) showed no detrimental effects of the pp65 antigen on expression of immunologically relevant markers. Low frequencies of cells expressing putative monocyte (<10% CD14$^+$), plasmacytoid (<40% CD123$^+$) and terminally differentiated DC (<10% CD83$^+$) markers were observed. (FIG. 21e). The co-expression of pp65 also did not affect the secretion of several endogenously up-regulated cytokines (low to moderate levels up to 10 pg/ml: IL-5, IL-12p, IL-10, IL-7, IL-6, IL-4 and TNF-α; high levels 1-10 ng/ml: IL-8 and MCP-1) or of the transgenic GM-CSF and IFN-α cytokines co-expressed in the vector, which were detectable at average of approximately 1.0 ng/ml and 4.6 ng/ml, respectively (n=3) (FIG. 21f). In conclusion, we observed no adverse effects of pp65 co-expression in cis in the vector on SmyleDC/pp65 viability or differentiation.

Production of SmyleDC/pp65 from Cord Blood Monocytes

A cord blood bank was set up with samples derived from human cord blood donated upon informed consent by term mothers giving birth at the Obstetrics Clinic at the Hannover Medical School. Mononuclear cells were isolated by Ficoll separation and then either frozen down and stored or preceded to CD34$^+$ hematopoietic stem cell enrichment. Both CD34 positive and negative fractions were cryopreserved for each donor sample. CD14$^+$ monocytes were enriched from the CD34 negative fraction by MACS. Those monocytes were transduced with virus encoding human GM-CSF-IFNa-pp65 using our previously described protocol and administered to the mice transplanted with CD34$^+$ cells from the same donor. A fraction of the SmyleDC/pp65 cells were maintained in culture for seven days for analyses of the DC differentiation immunophenotype and expression of the pp65 antigen.

Integration Pattern of ID-LV-G2αpp65 in SmyleDC/pp65

Although integration pattern of ID-LV sequences was previously shown in hepatocytes of mice infused with vectors (Matrai et al., 2011) and ID-LV have been explored for transduction of mouse and human DCs in vitro (Negri et al., 2012), the integration pattern of ID-LVs was not previously characterized for transduced monocytes or DCs. Although DCs are post-mitotic and non-replicating cells, a biased integration in a potentially oncogenic locus could predispose to genotoxic effects. In order to evaluate the integration pattern of the backbone LV-G2αpp65 vector, SmyleDC/pp65 generated with integrase competent (IC-LV) or integrase defective (ID-LV) vectors were kept in culture for 10, 20 and 30 days and the integrated vector copies were compared. Day 10 SmyleDC/pp65 generated with IC-LV showed fourfold higher numbers of integrated copies per cell (1.2 copies per cell) than SmyleDC/pp65 generated with ID-LV (0.3 copies per cell). For both cultures, the number of integrated copies/cell continuously decreased upon further culture (day 20) and when cells reached senescence (around 30 days; IC-LV: 0.3 copies per cell; ID-LV: 0.1 copies per cell) (FIG. 22a). The clonal contribution of the genetically modified monocytes was monitored with a high-throughput integration site (IS) analysis (Schmidt et al., 2007) on time points 10, 20 and 30 days after lentiviral transduction. Linear amplification mediated (LAM) PCR and next-generation sequencing detected >40.000 IS sequences for the monocytes transduced with IC-LV that were mapped to 3.000 unique chromosomal positions and >14.000 IS sequences that were mapped to >1.500 unique chromosomal positions for the monocytes transduced with ID-LV. The distribution of integration sites per chromosome was not biased, i.e. the number of integrations were overall correlated with the size of the chromosome for both vector types, i.e. more than 10 integrations detected for the larger chromosome 1 and about 1 integration for chromosome 21. The distribution regarding the number of viral integrations in the gene or +/−10 kb distance of a gene was similar for both vector types: most of the integrations were outside genes (FIG. 22b), particularly up to 5 kb upstream the transcription start site (FIG. 22c). The majority of ISs from all transduction time points were well below 5%, with a few occasionally reaching up to 5% of the total reads retrieved. The 10 most frequent gene locus showing insertions were quite diverse for each time point (FIG. 22d). Notably, monocytes transduced with ID-LV showed a recurrent insertion in the locus of the gene encoding for golgin antigen 7 (GOLGA7). The locus containing GOLGA7 was the most frequent IS for ID-LV at all time points, but with decreasing frequencies over time. Additional common locus where insertions occurred for both types of vectors were WDR74 (a protein required for blastocist formation in the mouse), Zink Finger Protein 37A (ZNF37A) and transmembrane phosphatase with tensin homology (TPTE). The RNA expression of all these proteins is usually ubiquitous and can be detected in white blood cells with unknown oncogenic function in humans.

HCMV Infection of SmyleDC/pp65 does not Allow Virus Replication In Vitro

Monocyte-derived DCs are known to be susceptible to HCMV infection and, upon their differentiation into activated DCs, virus replication was observed (Riegler et al., 2000). Therefore, one important safety aspect of SmyleDC/pp65 was whether this cell product would still allow HCMV spread, for example, if produced from a HCMV sero-positive donor. To address this, different types of lentivirus-vectored DCs were compared: SmyleDC expressing GM-CSF and IFN-α with SmartDC co-expressing GM-CSF and IL-4 (Daenthanasanmak et al., 2012). Dendritic cells were infected with the genetically modified viral strain HCMV-TB40/E expressing GFP at MOI of 2. Infected human fibroblasts (HF) were used as positive controls as previously described (Sinzger et al., 2008). Unstained cells are observed using fluorescence microscopy. A green fluorescent signal indicates infection of the cell. In this experiment fluorescent signals were only observed on day 10 in the SmartDCs not expressing IFN-α (FIG. 24a). These results were confirmed with FACS analysis. Seven days after infection, approximately 50% of the HF cells were infected, showing as GFP+ cells by flow cytometry analyses. Approximately 0.5% of the cells in the SmartDC cultures showed HCMV infection, whereas SmyleDC and SmyleDC/pp65 cells showed near baseline GFP+ cells (<0.06%). In order to avoid a possible artifact due to viral carry-over, the experiment was repeated with a MOI of 1 and the cells were washed extensively (5×) after viral infection. Kinetic analyses of GFP expression showed increasing amounts of HCMV-infected HF from day 2 to 10 post infection (FIG. 24a). For SmartDC, the frequency of GFP+ cells was initially 2%, which decreased to 0.2% on day 4, and then increased to 0.6% on day 10. For SmyleDC and SmyleDC/pp65, the initial infection was also approximately 2%, but even at later time points in the culture, the frequency of GFP+ cells was lower than 0.06%. These analyses were complemented by monitoring CD80, a relevant co-stimulatory marker up-regulated in activated DCs, but shown to be modulated after HCMV infection (Moutaftsi et al., 2002). For mock-infected cells, the expression of CD80 was comparable for the three types of DCs (detectable in 50% of the cells). On the other hand, upon HCMV infection, CD80 expression was down-regulated in SmartDC (detectable in 20% of the cells on day 10), but increased in SmyleDC and particularly in SmyleDC/pp65 after infection with the virus (detectable in 80% of the cells on day 10) (FIG. 24b). To evaluate whether cells could release new virions, supernatants collected from each time points were analyzed by plaque assay (FIG. 24c). Infected HF showed high amounts of virus released on day 4 ($1.4 \times 10^6$ pfu/ml) and gradually reduced on day 10 (to $1.35 \times 10^6$ pfu/ml) as most of the cells of the culture became lysed. Only residual amounts of virus was detectable on day 0 of DC cultures (120-300 pfu/ml, possibly reflecting remaining carry-over virus sticking on DC surface that was then released) (FIG. 24c). There was no detectable virus released until day 4 of culture for all DC groups. SmartDC started to release virus on day 6 (5 pfu/ml) which gradually increased on day 10 (to 35 pfu/ml). In contrast, no virus release was subsequently observed in SmyleDC or SmyleDC/pp65 cell supernatants. Thus, even if DCs might have been initially infected, IFN-α expression by SmyleDC and SmyleDC/pp65 seemed to better control both HCMV infection and release than IL-4 expressing SmartDC.

Stimulation and Expansion of CTL with Autologous SmyleDC/pp65 In Vitro

Both CD4+ T helper cells and CD8+ CTLs are required to protect individuals in controlling virus replication in primary HCMV infection (Gamadia et al., 2003) and in HCMV reactivation after HCT (Einsele et al., 2002). A 16 h IFN-γ catch assay based on flow cytometry analyses was used to evaluate whether SmyleDC/pp65 (harvested on day 7 after transduction) could activate both types of T cells obtained from HCMV sero-positive HD (n=3) (FIG. 25a). As controls arms, we included no stimulation, stimulation with pp65 peptide pool (the standard positive control for this assay) and SmyleDC not presenting pp65 antigen. For these healthy donors and under the short assay conditions, we did not observe an increase in the frequency of IFN-γ producing CD4+ or CD8+ cells upon stimulation with pp65 peptides. In contrast to the stimulation with pp65 peptides, CD3+ T cells stimulated with SmyleDC/pp65 resulted in significant increases in the frequency of IFN-γ producing CD4+ T cells (18 fold, p<0.05) and CD8+ T cells (5 fold, p<0.05). SmyleDC not loaded with pp65 antigen showed lower, but consistent stimulation of IFN-γ producing CD4+ and CD8+ cells, likely due to direct stimulatory effects of released IFN-α on activation of T cells for production IFN-γ (Hervas-Stubbs et al., 2011).

In order to further define the effects of pp65 expression on the activation of antigen-specific CD8+ effector cells, we performed two sequential microculture of DCs and T cells obtained from A*02; B*07 donors (n=3, HCMV sero-positive) in order to expand CTLs in enough numbers for further functional assays (FIG. 25b). SmyleDC/pp65 co-cultured with autologous purified CD8+ T cells resulted in a 7 fold higher T cell expansion in comparison with maintenance of T cells in the presence of stimulatory recombinant cytokines (IL-2, -7 and -15). Of note, co-culture of CTL with SmyleDC also resulted into higher T cell expansion (12 fold) showing that stimulation was partly due to homeostatic effects and antigen-independent. Similar expansion in microculture systems were also observed after co-culture of SmyleDC/pp65 with CD3+ T cells. Nevertheless, only CTLs expanded in the presence of SmyleDC/pp65 showed high frequencies of pp65-specific T cells, which were analyzed by pentamer staining (A*02 restricted epitope pp65 aa 495-503: mean=7.7% P value <0.05; B*07 restricted epitope pp65 aa 417-426: mean 6.4% P value <0.1) (FIG. 25b). In vitro expanded CTLs that had been stimulated with SmyleDC or SmyleDC/pp65 were subsequently evaluated for cytotoxic function. K562 cell genetically modified for constitutive expression of A*02 (KA*02) or B*07 (KB*07) and lentiviraly transduced for high levels of pp65 antigen expression were used as targets (FIG. 25c). CTLs were co-incubated at different effector to target (E:T) ratios for 4 hours and cell supernatants were evaluated for release of lactate dehydrogenase (LDH). CTLs expanded with SmyleDC showed similar cytotoxicity effects upon co-incubation with KA*02 or KB*07 targets, regardless if the pp65 antigen was expression in the target or not. In contrast, CTLs stimulated with SmyleDC/pp65 lysed in a dose-dependent manner more effectively K562 target cells expressing pp65 (FIG. 25c). This data validated in vitro effects of pp65 co-expression in the vectored DC to generate pp65-specific T cell stimulation.

Hematopoietic Reconstitution of NRG Mice Transplanted with Human Adult CD34+ Cells and Immunized with SmyleDC Vs. SmyleDC/pp65

Figure 26A:
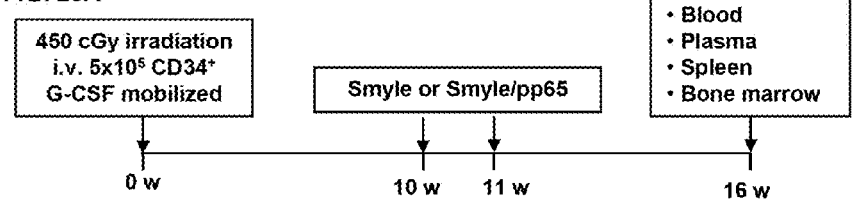
Figure 26B:
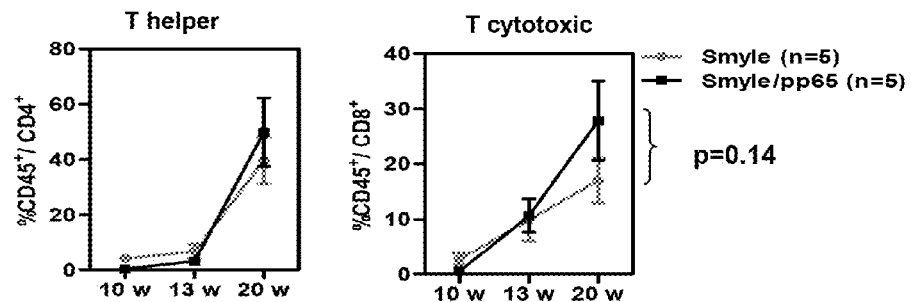
Figure 26C:
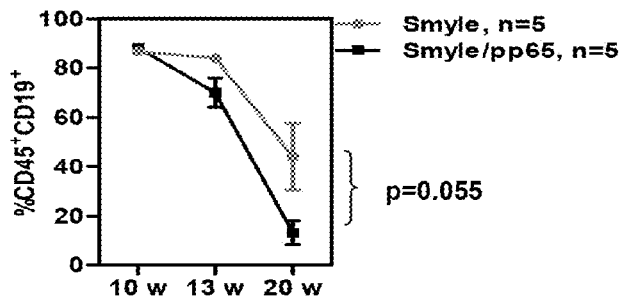
Figure 26D:
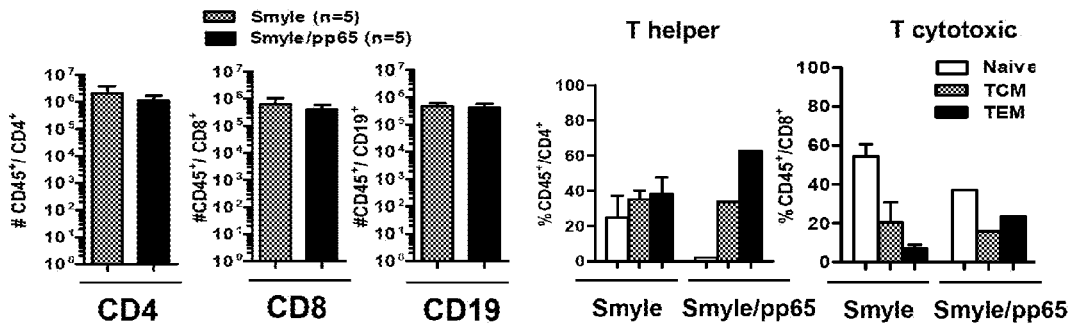

In order to demonstrate also the in vivo effects of SmyleDC/pp65 on CD8+ expansion and evaluate possible adaptive effects on B cells and humoral responses, 4 weeks-old irradiated NRG mice were transplanted with CD34+ cells that were obtained from G-CSF mobilized stem cell donors after 2 rounds of selection with magnetic beads (FIG. 26a). 10 weeks after HCT, engraftment of human hematopoietic cells was confirmed by analyses of peripheral blood at comparable levels for all mice. At this time-point, the average frequency of human CD45+ cells relative to mouse cells was approximately 2.5%. As we had previously observed for this HCT humanized mouse model (see example 3), the majority of human cells (80-90%) were B cells (defined as CD45+/CD19+ cells). The frequency of human T cells was much lower, with a clear predominance of T helper cells (defined as CD45+/CD4+ cells; 1-6%), whereas CTLs were found at very low frequencies (defined as CD45+/CD4+ cells; up to 3%). Therefore, CD14+ monocytes purified from the same HSC donor material were used for production of "autologous" SmyleDC or SmyleDC/pp65, in order to evaluate the effects on the adaptive hematopoietic reconstitution, i.e. expansion of T and B cells. DC vaccinations were performed as a single prime/boost at the $10^{th}$ and $11^{th}$ weeks after HCT. After intermediate PBL analyses on week 13 after HCT, mice were sacrificed on week 20 for macroscopic pathological examination and collection of tissues. First, we performed a kinetic analyses of human T and B cells detectable in blood. From weeks 13 to 20, mice immunized with SmyleDC or SmyleDC/pp65 showed noticeable increased frequencies of both human T helper cells (average of 50%) and CTL cells (30%) (FIG. 26b). Previous results from our group using this model, showed that non-immunized HCT controls, showed at week 20 similar levels of human T helper cells and CTLs as in week 10 (see "Example 2"). Incidentally, in contrast two weeks after the last immunization (week 13), the effects observed 9 weeks after DC prime/boost (week 20) were dramatic. At this point, the most frequent human cells were T cells, consisting of approximately 40% CD4+ T cells for both vaccine groups, whereas we observed average 17% CD8+ T cells for SmyleDC immunization and in average 30% for SmyleDC/pp65 (p>0.5) (FIG. 26b). These results showing a more pronounced effect of SmyleDC/pp65 on lowering the CD4/CD8 ratios (2.6 for SmyleDC and 1.5 for SmyleDC/pp65, p=0.07) were in agreement with our in vitro T cell stimulation assays demonstrating the effects of pp65 expression on expansion of CTLs. Concurrently, at week 20 of analyses, the frequency of B cells in both immunization groups significantly dropped to approximately 10% compared to initial 90% at week 10 (FIG. 26c). These results thus indicated that upon immunization, the vectored DCs were able to somehow switch the preferential development of HSC from B cells to T cells. We also observed a dominant repopulation of spleens with human T cells (37% Th, 18% CTL and 33% B cell). Around 33% of cells in spleens were human CD45+ lymphocytes, resulting in a 3-fold higher frequency than in PBL. A similar high frequency of human T lymphocytes was also detected in bone marrow (approximately 17% human cells; from those 35% Th, 26% CTL and 29% B cell). Analyses of phenotypic T cells markers in splenocytes was possible for only a subset of mice (n=5 for SmyleDC and n=2 for SmyleDC/pp65). Th cells analyzed from SmyleDC/pp65 immunized mice showed a more dominant effector memory phenotype and only residual levels of naïve cells, which was very distinct from the SmyleDC immunization, where the frequencies of naïve, central memory and effector memory were more balanced (FIG. 26d). Concurrently, the frequency of effector memory CTLs was also slightly higher after SmyleDC/pp65 immunization. Therefore, not only the B/T cell compartments were altered after immunization, but the levels of T cell activation as well. We monitored the mice for any signs of graft-versus host-disease. Despite the dramatic elevation in the frequencies and activation of the T cells, GVHD was observed in only one of the sixteen mice immunized with SmyleDC/pp65. PBL analyses showed high frequencies of effector memory Th and CTL cells in PBL, spleen and bone marrow.

Functional Human Homeostatic, T and B Cell Effects of SmyleDC/pp65 after HCT

Besides the effects on the reconstitution of the different hematopoietic lineages, we characterized several properties of the HIS mice immunized with SmyleDC/pp65 regarding functional immune responses. Mice transplanted with PBL-CD34+HSC and immunized with SmyleDC/pp65 showed a dramatic increase in the levels of several human cytokines that were detectable in the mice plasma (FIG. 27a). The cytokines reflected an unbiased Th1/Th2 pattern as both Th1 (up to 10 pg/ml: IL-5, IL-β; higher than 10 pg/ml: IFN-γ, GM-CSF, TNF-α, IFN-α) and Th2 (up to 10 pg/ml: IL-12, IL-4, IL-10, IL-6, IL-8; higher than 10 pg/ml: IFN-γ) type cytokines were detected, in addition to IL-5 (relevant for eosinophil activation) and MCP1 (a chemokine that regulates migration and infiltration of monocytes and macrophages). Remarkably, with exception of MCP1, these cytokines were not detectable in mice plasma after SmyleDC immunization, indicating a pivotal role of the endogenous pp65 antigen presentation by DC to stabilize immunologic synapses with T and B cells and promote a broad range production of human cytokines and chemokines To evaluate anti-pp65 specific T cell responses, splenocytes of mice immunized with SmyleDC/pp65 were pooled and sorted human Th cell and CTLs were non-specifically activated with CD2/CD3/CD28 beads and further expanded in vitro with SmyleDC/pp65 to allow further analyses. ELISPOT assay was used to assess anti-pp65 responses after one week stimulation. After pulsing the T cells with pp65, we observed both CD8+ and CD4+ T cell reactivity, measured as quantified IFN-γ positive spots, although only the CD8+ T reactivity was shown specific to pp65 as CD4+ that were not pulsed with pp65 peptide were also activated (FIG. 27b).

Another relevant immune monitoring parameter was seroconversion in mice after HCT and immunization. Notably, several types of human immunoglobulins were detectable (IgA, IgG1, IgG2, IgG3, IgG4 and IgGM) after SmyleDC/pp65 immunization (FIG. 27c). In the absence of the antigen in the SmyleDC vaccine, we could only observe IgM production. Therefore, antigen presentation by SmyleDC/pp65 promoted Ig-switch during B cell development. Analyses of plasma immunoglobulin reactivity specific against pp65 showed detectable levels of IgM (FIG. 27d).

Hematopoietic Reconstitution of NRG Mice Transplanted with Human Cord Blood CD34+ Cells and Immunized with Different Doses of SmyleDC/pp65

Figure 28A:
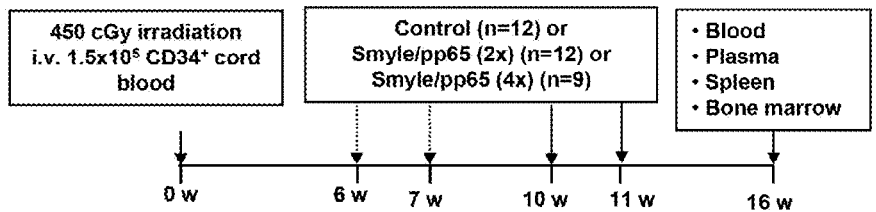
Figure 28B:
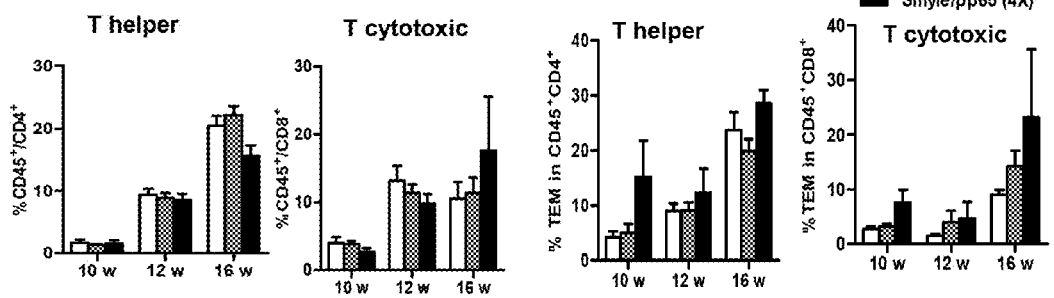
Figure 28C:
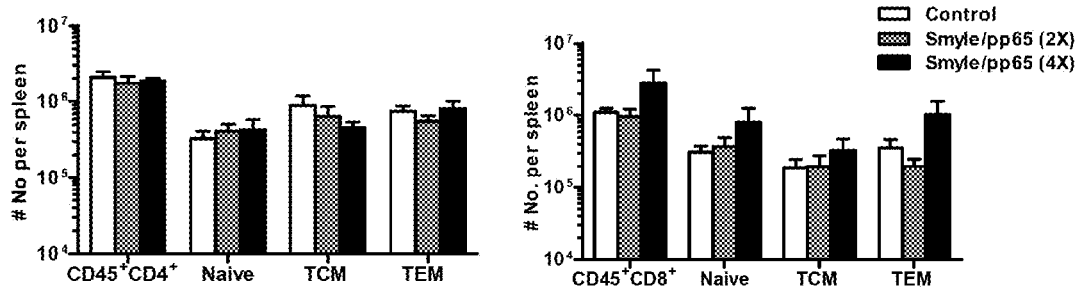

UCB is a rich source of HSC and progenitor cells at very immature stages of differentiation. Therefore, as a more stringent model to address the effects of lentivirus vectored DCs in the hematopoietic reconstitution in vivo, we used CD34+ cells isolated from UCB as a source of HSC. Generation of SmyleDC/pp65 from UCB monocytes was feasible using our standard protocol. CD34+ UCBT into NRG mice could be reproducibly established with a dose of $1.5 \times 10^5$ cells injected i.v. into irradiated 4-weeks-old mice (FIG. 28a). We compared non-immunized mice with mice immunized with SmyleDC/pp65 as previously performed for the PBL-CD34+ model, i.e., at 10 and 11 weeks after HCT. In addition, taking in account the more immature HSC status and possible more anergic environment, we administered additionally earlier SmyleDC/pp65 immunizations, on weeks 6 and 7 after HCT (FIG. 28b). Control non-immunized mice showed 10 weeks after HCT 60-80% of the circulating lymphocytes to be of human origin, with >90% of them consisting on B cells and about 10% T cells (FIG. 28b). From weeks 10 to 16 post HCT, we observed a continuous gradual increase in the frequencies of Th cells and CTLs in blood, peaking at 20% for Th and 10% for CTL. The CD4/CD8 ratio did not change upon one prime/boost vaccination with SmyleDC/pp65 (3.1 for control vs. 2.6 for vaccinated mice at week 16, p=0.45), but a lower CD4/CD8 ratio was observed at the latest 16 weeks time-point after 2 prime/boost SmyleDC/pp65 vaccinations (1.6, p=0.09). The frequency of B cells was not affected after SmyleDC/pp65 immunizations (approximately 90% before vaccination to around 50% at week 16 for all groups). Along with these findings, the more intensive SmyleDC/pp65 immunization also showed a quantitative effect regarding the higher frequencies effector memory CTLs from time-point 10 weeks post-HCT until 16 weeks (9% vs. 29.5 respectively, p=0.1, FIG. 28c). In the spleen, the absolute counts for total CTL ($2.7 \times 10^6$ vs. $1.1 \times 10^6$ for control mice, p=0.18), naïve CTL ($0.8 \times 10^6$ vs. $0.3 \times 10^6$ for control mice, p=0.46) and EM CTL ($1 \times 10^6$ vs. $0.3 \times 10^6$ for control mice, p=0.18) were increased after the intensive 4× SmyleDC/pp65 immunization (FIG. 28c).

SmyleDC/pp65 Immunization Enhances the Thymic T Cell Development

Figure 28D:
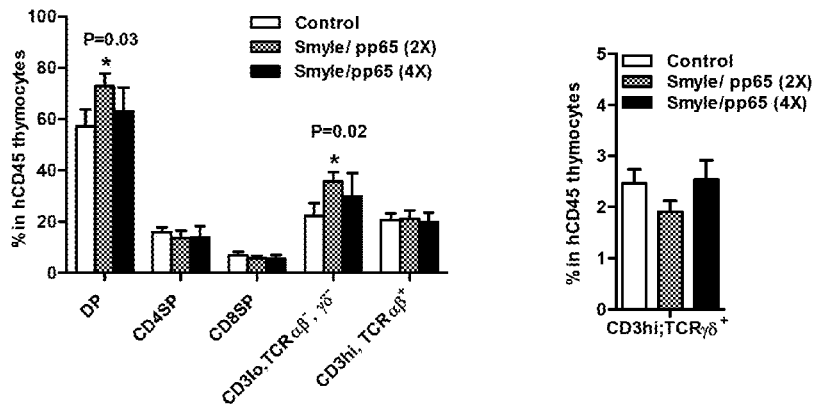
Figure 28F:
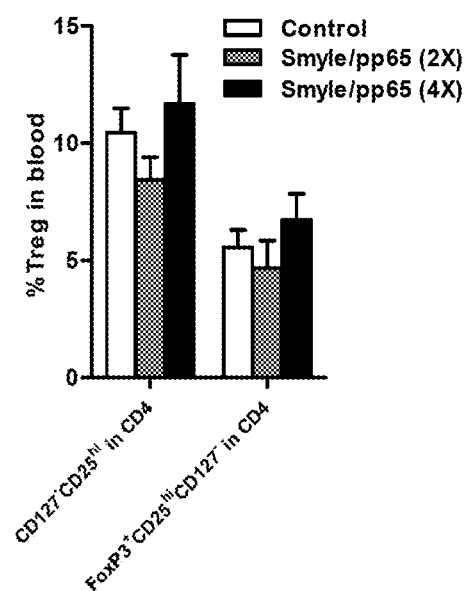
Figure 29A:
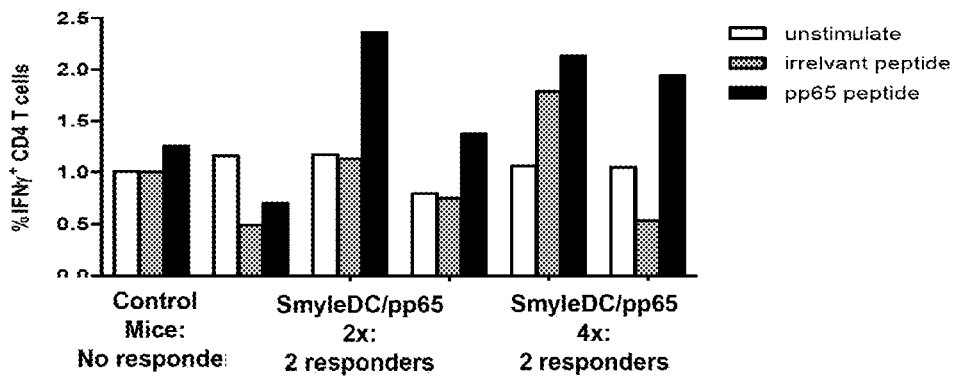
Figure 29B:
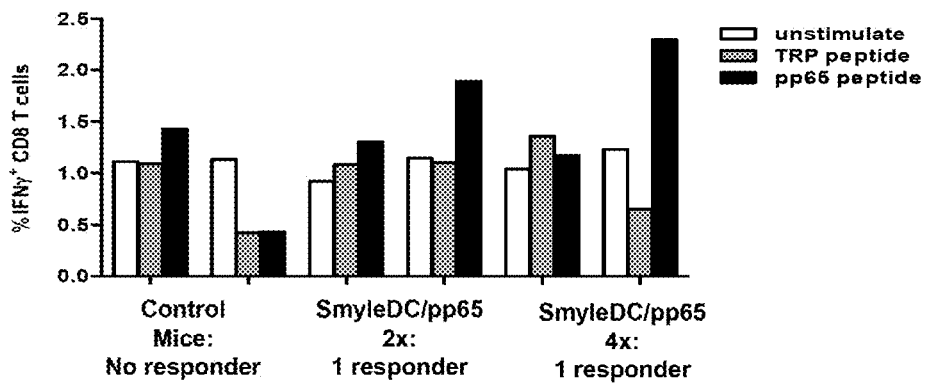
Figure 29C:
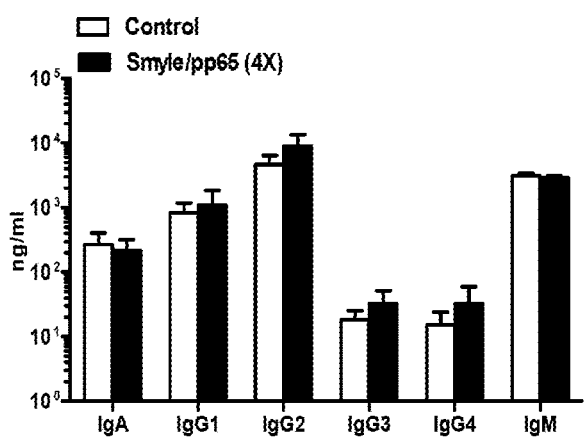
Figure 29D:
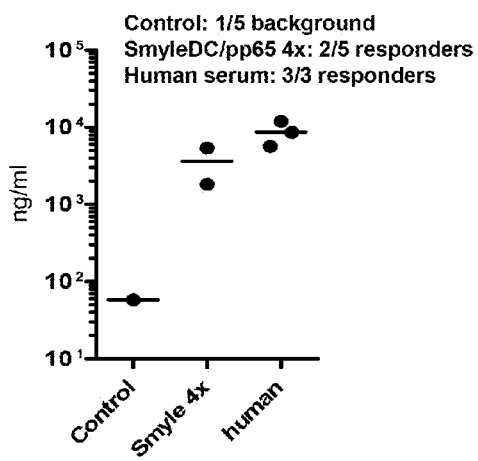

We evaluated if the expansion of mature T cells derived from the cord blood stem cell reconstitution was a peripheral extrathymic event or could have been also a consequence of SmyleDC/pp65 immunization enhancing the development of T cells in the thymus. We observed significantly higher frequencies of double positive CD4+/CD8+ and CD3+/lo; TCRαβ− T cell precursors in thymus of mice immunized with SmyleDC/pp65 (2×) (FIG. 28d). This indicates a higher turn-over thymic T cell development, which may result into higher numbers of CTLs that can be then mobilized to the blood as naïve T cells for subsequent antigenic stimulation and progression into mature T cells in the periphery (in LN and spleen).

SmyleDC/pp65 Immunization Enhances the Thymic T Cell Development

To evaluate the impact of SmyleDC/pp65 in the T cell lineages implicated with tolerance, we examined the frequencies of CD4+FoxP3+CD25+CD127− regulatory T cells (Tregs). Although SmyleDC/pp65 immunization improved reconstitution of mature and functional human CTL and humoral responses after UCBT, a modest but noticeable expansion of regulatory CD4+FoxP3+CD25+CD127− T cells was also observed. Notably, 4× SmyleDC/pp65 immunization augmented their frequency in blood (6.7%; 4× SmyleDC/pp65 vs. control, p=0.06, FIG. 28e). The balanced regeneration of both effector and tolerogenic cells could potentially confer tolerogenic capabilities to counterbalance the occurrence of graft-versus-host disease (GVHD). Noteworthy, mice transplanted with HSC from UCB and maintained in observation for up to 16 weeks did not develop GVHD.

No Signs or Mild, Grade 1 GVHD in NRG Mice Reconstituted with Functional Human Immune System When reconstituting a fully functional human immune system in a mouse after xenogeneic transplantation of hematopoietic stem cells, graft-versus-host disease of the mouse is a concern. After all, the HLA molecules of the recipient are not matched to those of the donor at all. For this reason, animals which were used in the examples described above were assessed for signs and symptoms of GVHD. Assessment was based on anatomic features such as inflammation of the gut and/or the frequency of regulatory immune cells. The anatomic assessment was done by an experienced pathologist. The results of the assessment are summarized in the Table 3.

The results indicate that the reconstituted human immune system did not cause moderate or severe signs of GVHD in mice even though it was in other respects functional. Thus, the use of the iDCs of the present invention for assisting the reconstitution of a functional immune system in a recipient after hematopoietic stem cell transplantation has the potential to induce tolerance of the transplanted immune system for the tissue of the recipient. Given the fact that leukocyte antigens between mice and humans differ more that the HLA molecules of different humans, the use of the iDCs of the present invention, thus, has the potential to allow allogeneic HSC transplantation using donors which do not meet the matching criteria which are presently applied to minimize GVDH after transplantation. This use of iDCs has the potential to significantly widen the range of potential donors for a given patient and, thus, find donors for recipients with rare combinations of HLA-molecules.

Discussion

Transplant of allogeneic HSC is a validated therapeutic option for patients with high-risk hematological malignancies, but HCMV infections pose a significant risk on survival. Our results show that the tricistronic ID-LV encoding GM-CSF, IFN-γ and the HCMV pp65 antigen under the control of the early CMV promoter can reprogram at high efficiency human CD14+ monocytes from peripheral blood from G-CSF mobilized donors and cord blood. A single overnight exposure of monocytes to the ID-LV vector drives their self-differentiation into DCs that are maintained autonomously for seven days with high viability, immunologic properties (expression of MHC II, co-stimulatory molecules and inflammatory of cytokines) and constitutive expressing of GM-CSF, IFN-γ and pp65. Although it has been previously reported that ectopic expression of pp65 could inhibit IFN signaling (Browne and Shenk, 2003), we did not observe a detrimental effect of pp65 expressed in cis in the tricistronic vector, supporting our previous studies where pp65 was co-expresses in trans, using two vectors for DC reprogramming (Daenthanasanmak et al., 2012; Salguero et al., 2011).

Transduction of monocytes with ID-LV at MOI of 5 resulted into less than 0.3 copies of vector per cells and analyses of the integration pattern showed high polyclonality and no bias for previously described proto-oncogenic clusters. Integration of ID-LV into the GOLGA7 cluster region seemed to be the most frequent "hot spot", which may reflect an active transcriptional region in activated monocytes in their process to differentiate into activated dendritic cells. GOLGA7 is an ubiquitously expressed protein and functions as a palmitoylation enzyme for shuttling proteins from the Golgi to the plasma membrane (Ohta et al., 2003). GOLGA7 gene expression is increased in activated DCs (Cuiffo and Ren, 2010; Li et al., 2000). During DC and B cell activation, MHCII is actively externalized from internal vesicles to the plasma membrane and GOLGA7 may have an important role in the protein shuttling through the Golgi apparatus. GOLGA7 is located in chromosome 8 in a region associated with trisomy mosaicism in myelomonocytic leukemia (Ripperger et al., 2011) but is not known to be proto-oncogenic. However, it remains to be elucidated mechanistically why the IC-LV did not show the same preferential integration site, indicating that recombination and eventual integration of the ID-LV in the genome of activated monocytes may be more biased than IC-LV for highly transcribed "open" genomic regions. Nevertheless, both types of lentivirus-vectored DCs did not show integrations in the most known hot spots characterized in preclinical studies of lentiviral vectors used to genetically modify hematopoietic stem cells (KDM2A, PACS1 and TNRC6C) (Aiuti et al., 2013). This reflects the behavior of HIV-1 to integrate into chromatin regions actively being transcribed, which will depend on the cell type and activation stimulus.

As a potential safety concern, we examined if SmyleDC/pp65 could spread HCMV, because it was reported that dendritic cells derived in vitro from CD34$^+$ and CD14$^+$ progenitors were highly susceptible and permissive to the complete replicative cycle of HCMV (Hertel et al., 2003; Riegler et al., 2000). Our in vitro infection studies with the endotheliotropic strain TB40/E-GFP indicated that high expression of IFN-$\gamma$ by SmyleDC may inhibit viral replication, as SmartDC expressing IL-4 was more susceptible for HCMV infection and caused HCMV spread. Notably, exposure of SmyleDC and SmyleDC/pp65 to HCMV in vitro resulted in up-regulation of CD80, which is a critical co-stimulatory molecule to co-activate T cells, suggesting that constitutive IFN-$\gamma$ also precluded potential HCMV immune supressive effects on these DCs.

Clinically, pp65-specific CD4$^+$ and CD8$^+$ T cells were demonstrated to play a critical role in HCMV clearance. From our results, we observed a clear effect of endogenously expressed pp65 in the vectored DC for stimulation of CD4$^+$ and CD8$^+$ T cell responses in vitro, which was detected by up-regulation of IFN-$\gamma$ intracellular staining and expansion of T cells with TCRs reactive against pp65 immune dominant epitopes. Moreover, expanded pp65-specific CD8$^+$ T cells exhibited superior cytolytic activity against target cells expressing pp65 antigen.

In addition to strong antigenic stimulations in vitro, SmyleDC/pp65 accelerated the hematopoietic reconstitution in HCT and UCBT humanized mouse models. Similar to our results in vitro, expression of the pp65 antigen by the DCs used for immunization produced quantitative and/or qualitative higher frequencies of human effector CTLs in blood and spleen. After SmyleDC/pp65 immunization, T cells that developed de novo in thymus and bio-distributed to several tissues became predominantly memory T cells, whereas in the absence of antigen (SmyleDC immunization after HCT), we observed predominantly expansion of the naïve CTL subset in the blood. It is not clear what drove the differentiation of the populations of effector memory CTLs observed in spleen and bone marrow of SmyleDC vaccinated mice. They could represent T cells reactive to mouse xeno-antigens, as were also observed in non-immunized mice after PBL-HCT (see example 2), One of the limitations in immune reconstitution of humanized models after HCT is the poor reconstitution of mature B cells and lack of Ig class switching. Remarkably, IgM, IgG and IgA were detected at high levels in mice immunized with SmyleDC/pp65 after HCT (but not with SmyleDC), supporting the concept that pp65 antigen may influence the maturation of B cells for Ig class switching. Studies in humanized mice demonstrated that B cell maturation was correlated with development of effector T cells (Lang et al., 2013). Thus, expansion of pp65-specific CD4$^+$ T cells driven by SmyleDC/pp65 group may provide critical maturation factors such as CD40L that are required for B cell maturation, Ig class switch and secretion of antigen-specific specific antibodies. Several efforts have been made to improve adaptive immune responses in HIS mice, such as delivering of recombinant cytokines as GM-CSF and IL-4 (Chen et al., 2012) or transgenic expression of HLA class I or II (Jaiswal et al., 2012; Suzuki et al., 2012). SmyleDC/pp65 may fulfill several of these requirements as it is fully HLA-matched with the transplanted HSC, expresses a wide array of cytokines and provides a potent antigenic signal.

For human young patients, T cell immune reconstitution following lymphodepletion can occur through active thymopoiesis, but for elder adults, it primarily occurs through homeostatic proliferation of peripherally expanded clones (Williams et al., 2007). Homeostatic proliferation results is a rapid and significant expansion of the peripheral T cell pool, and is dependent upon both homeostatic cytokines and antigen-driven responses in the period following lymphopenia (Williams et al., 2007). Although several vaccine candidates against HCMV are currently being evaluated in clinical trials, a personalized vectored dendritic cell vaccine that is highly viable, can be potentially produced in large scale and provides both antigenic and homeostatic immune reconstitution is a promising clinical innovation to lower mortality and morbidity after HCT and UCBT.

Increasing pathological and clinical evidences indicated that HCMV may be an etiologic agent in malignancies such as glioma and breast cancer (Soderberg-Naucler et al., 2013; Taher et al., 2013). Although infection of malignant hematopoietic cells with HCMV has not been reported, HCMV positive serostatus of the HCT recipient or donor negatively impacts on survival of acute leukemia patients (particularly acute lymphoblastic leukemia) (Schmidt-Hieber et al., 2013b). Moreover, acute myeloid leukemia patients with HCMV reactivation early after HCT showed lower relapse risk, suggesting either a putative "virus-versus-leukemia" effect (Elmaagacli, 2013; Green et al., 2013) or that HCMV maybe also an etiologic agent increasing leukemia relapse. Thus, immunization to control HCMV after HCT might be also explored with the rationale to improve graft-versus-leukemia and lower leukemia relapse rates. Therefore, up-scaling the virus production and validation of SmyleDC/pp65 production under good manufacturing practices (GMP) are undergoing developments for future immunotherapy clinical trials against high risk acute leukemia.

Materials and Methods

Plasmid Construction and Integrase-Defective Lentiviral Vector (ID-LV) Production The lentiviral backbone vector RRL was kindly provided by Prof. Luigi Naldini (Univ. Milan). The construction of vectors RRL-cPPT-CMVp-GM-CSF-P2A-IFN-$\alpha$ (LV-G2$\alpha$) and RRL-cPPT-CMVp-pp65 (65 kDa) was previously described (Daenthanasanmak et al., 2012). For the generation of LV-GM-CSF-P2A-IFN-$\alpha$-F2A-pp65 (LV-G2$\alpha$-pp65), overlapping-PCR was performed using cDNAs of human GM-CSF-IFN-$\alpha$ and pp65 as templates interspaced with a 2A element of foot and mouth disease virus (F2A). The strategy of LV construction with F2A element was previously described (Szymczak and Vignali, 2005). Primers used to generate the interspacing F2A element between IFN-α and pp65 were:

```
F2A/pp65 Forward
                                      (SEQ ID NO: 7)
5'-CCGGTGAAACAGACTTTGAATTTTGACCTTCTCAAGTTGGCGGGAGA CGTGGAGTCCAACCCAGGGCCCATGGAGTCGCGCGGTCGCCGTTG-3'
and F2A/IFN-α Reverse:
                                      (SEQ ID NO: 8)
5'-TGGGTTGGACTCCACGTCTCCCGCCAACTTGAGAAGGTCAAAATTCA

AAGTCTGTTTCACCGGTTCCTTACTTCTTAAACTTTCTTGCA-3'.
```

The PCR products were digested with restriction enzymes XbaI and ClaI and inserted into the multiple cloning site of RRL-cPPT-CMVp-MCS vector. The structural integrity of all constructs was confirmed by restriction digestion and sequencing analyses. Large scale lentivirus production was performed by transient co-transfection of human embryonic kidney 293T cells as formerly described (Stripecke, 2009). Generation of ID-LVs was performed by using the combination of the backbone vector with the following packaging plasmids in the co-transfection: a plasmid expressing gag/pol containing a D64V point mutation (kindly provided by Prof. Axel Schambach, Hannover Medical School) and a plasmid expressing rev and a plasmid encoding the VSV-G envelope.

Generation of Lentivirus Vectored DCs with ID-LVs

Peripheral blood mononuclear cells (PBMCs) obtained from HLA-A*02.01/HLA-B*07.02 positive HCMV-reactive adult healthy volunteers, leukapheresis obtained form G-CSF mobilized donors and umbilical cord blood were obtained in accordance with study protocols approved by the Hannover Medical School Ethics Review Board. Generation of lentivirus-induced DCs from CD14$^+$ monocytes was previously described (Daenthanasanmak et al., 2012). Briefly, CD14$^+$ was isolated from PBMCs using CD14 isolation beads (Miltenyi Biotech, Bergisch-Gladbach, Germany). The monocytes were pre-conditioned withrecombinant human GM-CSF and IL-4 (50 ng/ml each, Cellgenix, Freiburg, Germany) for 8 h prior to transduction. 2.5 µg/mL p24 equivalent of ID-LV-G2α/pp65 was used to transduced $5\times10^6$ monocytes at the multiplicity of infection (MOI) of 5 in the presence of 5 µg/ml protamine sulfate (Valeant, Dusseldorf, Germany) for 16 h. After transduction, the cells were washed twice with phosphate-buffered saline (PBS) and further maintained in culture with serum-free X-vivo medium (Lonza) or used directly for mice immunizations.

Analyses of Cytokines and Transgene Expression

The detection of HCMV pp65 protein in 293T cell lysates and supernatants was determined by Western blot analysis (Bio-Rad, Munich, Germany). For intracellular pp65 expression in SmyleDC/pp65 was performed by intracellular staining and flow cytometry, previously described (Daenthanasanmak et al., 2012). SmyleDCs were first stained for DC surface antigens with the combination of monoclonal antibodies anti-human CD14, HLA-DR, HLA-ABC, CD80, CD86, CD83, CD11c and CD123 followed by fixing and permeabilization with BD cytofix/cytoperm solution (Becton Dickinson GmbH, Heidelberg, Germany) and incubated with FITC conjugated mouse monoclonal antibody against HCMV-pp65 (Pierce Biotechnology, Rockford, USA). The analysis was performed with FACS Calibur apparatus (Becton Dickinson) using CellQuest software. Detection of cytokines in cell supernatants of SmyleDC cultures was performed by multiplex luminex bead kit used according to the manufacturer's instructions (Milliplex Milipore, Billerica, USA).

Integration Analysis

SmyleDC/pp65 generated from IC-LV and ID-LV kept in culture for 10, 20 and 30 days were evaluated for virus copy number and integration site analysis with LAM-PCR method as previously describes (Schmidt et al., 2007). Number of integrated LV copy was quantified by qPCR.

HCMV-TB40/E GFP Infection and Plaque Assay

The HCMV TB40/E GFP strain was propagated as previously described (Sinzger et al., 2008) and the viral titer was $1.75\times10^7$ pfu/ml. Each type of target DCs was seeded at $5\times10^5$ cells well in six wells for each time point (0, 2, 4, 6, 8 and 10 days post infection, d.p.i.). Human fibroblasts (HF) were used as a positive control. DCs and HF cells were infected with HCMV (at MOI of 2 and 1) for 24 h. After infection, cells were washed with PBS and kept in cultures with DMEM supplemented with 10% FBS and 1% Penicillin and Streptomycin. Infected cells were harvested at each time point for GFP analyses and PE-conjugated anti-human CD80 was used for surface staining of DCs. After washing, cells were fixed in 1% paraformaldehyde and analyzed by flow cytometry. For plaque forming assays, cell supernatants were collected at each time point and 100 µl of undiluted and diluted (20 µl in 10 fold serial dilutions) of DC supernatants were added to monolayer HF cells seeded in 48 well plates. Two duplicate wells were set up for each supernatant and each time point. After 2 hours incubation, 500 µl of carboxymethylcellulose was added to ensure that infection will only be possible from cell to cell. Number of plaques was analyzed after 4 to 10 days post infection. Giemsa staining was used to stain plaques on day 10 for confirmation of plaques numbers. Titers (pfu/ml) were calculated from mean value of plaque numbers counted from duplicate wells x dilution factor/volume of dilution (0.1 ml).

Analyses of pp65-Reactive T Cells Stimulated In Vitro

Autologous CD3$^+$ and CD8$^+$ T cells were isolated from PBMC using the MACS system following the manufacturer's protocol (Miltenyi Biotec). For IFN-γ intracellular staining analysis of T cells stimulated for 16 h with 10 µg/ml PepTivator CMV-pp65 overlapping peptide pool (Miltenyi Biotec) or with DCs by T cells were harvested, stained with APC-conjugated anti-human CD3, PB-conjugated anti-human CD4 and PCy7-conjugated anti-human CD8 antibodies. After fixation/permeabilization with Cyofix/perm (BD) for 20 min at 4° C. and washing, anti-human IFNγ (ebioscience) was used for staining for 30 min. The cells were acquired and analyzed by flow cytometry using LSRII (Beckman Coulter). For the microculture expansion system, SmyleDC or SmyleDC/pp65 (day 7) were co-cultured with autologous isolated CD8$^+$ T cells in in 96-well-plates at ratio of 1:10 (APC: T-cell) in X-vivo medium supplemented with 5% human AB serum. Gamma-irradiated autologous CD8$^-$ feeder cells ($2\times10^5$) were added per microculture. After 3 days, the cells were replenished on alternate days with IL-2 (20 IU /ml) (Novartis Pharma GmbH, Germany) IL-7 and IL-15 (5 ng/ml each, Cellgenix, Gladbach, Germany). For re-stimulation after 7 days, cryopreserved DCs were thawed and added to T cells at 1:10 ratio. Re-stimulated T cells were harvested, counted and analyzed for pp65-reactivity by tetramer staining PE-conjugated tetramers (HLA-A*0201-NLVPMVATV, pp65 amino acids (aa) 495-503; HLA-B*0702-TPRVTGGGAM, pp65 aa 417-426; Beckman Coulter), APC-conjugated anti-human CD3, PB-conjugated anti-human CD4 and PCy7-conjugated anti-human CD8 were used.

Hematopoietic Stem Cell Transplantation into Immune Deficient NRG Mice

Breeding pairs of NOD.Cg-Rag1$^{tm1Mom}$Il2rg$^{tm1Wjl}$ (Nod.Rag1$^{-/-}$.IL2rγ$^{-/-}$, NRG) mice were bred and maintained under pathogen free conditions in an IVC system (BioZone, United Kingdom). All procedures involving mice were reviewed and approved by the Lower Saxony and followed the guidelines provided by the Animal Facility at the Hannover Medical School. 5×10$^5$ human CD34 stem cells isolated with MACS system from G-CSF mobilized donor or 1.5×10$^5$CD34 cells from cord blood were transplanted into 4 weeks-old irradiated NRG mice via tail vein. At weeks 6/7 and 10/11 after transplantation, mice were vaccinated as prime/boost with 5×10$^5$ autologous SmyleDC or SmyleDC/pp65 by subcutaneous injection on the hind flanks Peripheral blood was collected form each mouse at week 10, before immunization, for baseline flow cytometry analyses. Mice were sacrificed at week 20 for collection of blood, plasma, spleen and bone marrow. PBL samples were treated twice with erythrocyte lysis buffer (0.83% ammonium chloride/20mMHepes, pH 7.2) for 5 min, washed with PBS and stained with human antibodies PB-conjugated anti-CD45, APC-conjugated anti-CD3, Alexa700-conjugated anti-CD19, APHCy7-conjugated anti-CD4, PCy7-conjugated anti-CD8, FITC-conjugated anti-CD45RA, PCy5-conjugated anti-CD62L. T cell subpopulations were defined by cells positive for CD45RA$^+$CD62L$^+$ are naïve cells (N), T Central Memory (TCM, CD45RA$^-$CD62L$^-$) and T Effector Memory (TEM, CD45RA$^+$ CD62L$^+$). Analyses were performed in a FACS LSRII flow cytometer (Becton Dickinson) using Flowjo software. For T cell effector function assays, human CD4$^+$ and CD8$^+$ T cells were sorted from splenocytes with a Moflo apparatus (Becton Dickinson); sorted CD4 or CD8$^+$ splenocytes obtained from mice (n=3) were pooled and stimulated with CD2/CD3/CD28 beads (T cell activation kit, Miltenyi Biotec) for 48 h prior to 7-day in vitro stimulation with SmyleDC/pp65. 50,000 T cells were harvested and seeded per well on IFN-γ antibody-coated ELISPOT plate and pulsed with pp65 peptide pool overnight. The plates were developed as described by the manufacturer (Mabtech, Germany). Cells not pulsed with peptides were used as controls. Level of cytokines and immunoglobulins (IgA, IgM, IgG1, IG2, IgG3 and IgG4) in mice plasma were quantified with bead array according to the manufacturer's protocol (Milliplex Milipore, Billerica, USA). For analyses of Treg frequency, mononuclear cells were initially stained for surface markers with PB-conjugated anti-CD45, FITC-conjugated anti-CD3, Alexa700-conjugated anti-CD4, APC-conjugated anti-CD127, PCy7-conjugated anti-CD25. After fixation/permeabilization with Foxp3 fix/perm buffer (ebioscience) for 30 min at 4° C. followed by washing, PE-conjugated anti-Foxp3 was used for 30 min staining followed by washing and further proceeded for cell acquisitions.

Analyses of Thymus

Thymuses were harvested and single cell suspensions were subsequently stained with PB-conjugated anti-CD45, FITC-conjugated anti-CD3, A700-conjugated anti-CD4, APC-conjugated anti-CD3, FITC-conjugated anti-TCRαβ and FITC-conjugated anti-TCR γδ followed by washing and analyzed by LSRII flow cytometry. Analyses of T cells at different stages of development in thymus. DP: CD45$^+$/CD4$^+$/CD8$^+$, CD4SP: CD45$^+$/CD4$^+$/CD8$^-$, CD8SP: CD45$^+$/CD4$^-$/CD8$^+$ CD3$^{lo}$: CD45$^+$/TCRαβ$^-$/TCRγδ$^-$CD3αβ$^{hi}$: CD45$^+$/TCRαβ$^+$, CD3γδ$^{hi}$: CD45$^+$/TCRγδ$^+$ analyses were performed using FloJo (Tree Star Inc., Ashland, Oreg.) software.

Statistical Analysis

Non-parametric Man Whitney T test statistical analysis was used for determining statistical significance. All tests were one-sided, and P<0.05 was considered significant. Data was analyzed with GraphPad Prism 5 software (San Diego, Calif., USA).

REFERENCES

Aiuti, A., Biasco, L., Scaramuzza, S., Ferrua, F., Cicalese, M. P., Baricordi, C., Dionisio, F., Calabria, A., Giannelli, S., Castiello, M. C., et al. (2013). Lentiviral hematopoietic stem cell gene therapy in patients with Wiskott-Aldrich syndrome. Science 341, 1233151.

Boeckh, M., and Geballe, A. P. (2011). Cytomegalovirus: pathogen, paradigm, and puzzle. The Journal of clinical investigation 121, 1673-1680.

Boeckh, M., and Nichols, W. G. (2004). The impact of cytomegalovirus serostatus of donor and recipient before hematopoietic stem cell transplantation in the era of antiviral prophylaxis and preemptive therapy. Blood 103, 2003-2008.

Browne, E. P., and Shenk, T. (2003). Human cytomegalovirus UL83-coded pp65 virion protein inhibits antiviral gene expression in infected cells. Proceedings of the National Academy of Sciences of the United States of America 100, 11439-11444.

Chen, Q., He, F., Kwang, J., Chan, J. K., and Chen, J. (2012). GM-CSF and IL-4 stimulate antibody responses in humanized mice by promoting T, B, and dendritic cell maturation. J Immunol 189, 5223-5229.

Cuiffo, B., and Ren, R. (2010). Palmitoylation of oncogenic NRAS is essential for leukemogenesis. Blood 115, 3598-3605.

Daenthanasanmak, A., Salguero, G., Borchers, S., Figueiredo, C., Jacobs, R., Sundarasetty, B. S., Schneider, A., Schambach, A., Eiz-Vesper, B., Blasczyk, R., et al. (2012). Integrase-defective lentiviral vectors encoding cytokines induce differentiation of human dendritic cells and stimulate multivalent immune responses in vitro and in vivo. Vaccine 30, 5118-5131.

Einsele, H., Roosnek, E., Rufer, N., Sinzger, C., Riegler, S., Loffler, J., Grigoleit, U., Moris, A., Rammensee, H. G., Kanz, L., et al. (2002). Infusion of cytomegalovirus (CMV)-specific T cells for the treatment of CMV infection not responding to antiviral chemotherapy. Blood 99, 3916-3922.

Elmaagacli, A. H. (2013). CMV and relapse—What has conditioning to do with it? Biology of blood and marrow transplantation: journal of the American Society for Blood and Marrow Transplantation.

Feuchtinger, T., Opherk, K., Bicanic, O., Schumm, M., Grigoleit, G. U., Hamprecht, K., Jahn, G., Handgretinger, R., and Lang, P. (2010). Dendritic cell vaccination in an allogeneic stem cell recipient receiving a transplant from a human cytomegalovirus (HCMV)-seronegative donor: induction of a HCMV-specific T(helper) cell response. Cytotherapy 12, 945-950.

Gamadia, L. E., Remmerswaal, E. B., Weel, J. F., Bemelman, F., van Lier, R. A., and Ten Berge, I. J. (2003). Primary immune responses to human CMV: a critical role for IFN-gamma-producing CD4+ T cells in protection against CMV disease. Blood 101, 2686-2692.

Gluckman, E., Broxmeyer, H. A., Auerbach, A. D., Friedman, H. S., Douglas, G. W., Devergie, A., Esperou, H., Thierry, D., Socie, G., Lehn, P., et al. (1989). Hematopoietic reconstitution in a patient with Fanconi's anemia by means of umbilical-cord blood from an HLA-identical sibling. The New England journal of medicine 321, 1174-1178.

Green, M. L., Leisenring, W. M., Xie, H., Walter, R. B., Mielcarek, M., Sandmaier, B. M., Riddell, S. R., and Boeckh, M. (2013). CMV reactivation after allogeneic HCT and relapse risk: evidence for early protection in acute myeloid leukemia. Blood 122, 1316-1324.

Griffiths, P. D., Stanton, A., McCarrell, E., Smith, C., Osman, M., Harber, M., Davenport, A., Jones, G., Wheeler, D.C., O'Beirne, J., et al. (2011). Cytomegalovirus glycoprotein-B vaccine with MF59 adjuvant in transplant recipients: a phase 2 randomised placebo-controlled trial. Lancet 377, 1256-1263.

Grigoleit, G. U., Kapp, M., Hebart, H., Fick, K., Beck, R., Jahn, G., and Einsele, H. (2007). Dendritic cell vaccination in allogeneic stem cell recipients: induction of human cytomegalovirus (HCMV)-specific cytotoxic T lymphocyte responses even in patients receiving a transplant from an HCMV-seronegative donor. The Journal of infectious diseases 196, 699-704.

Hertel, L., Lacaille, V. G., Strobl, H., Mellins, E. D., and Mocarski, E. S. (2003). Susceptibility of immature and mature Langerhans cell-type dendritic cells to infection and immunomodulation by human cytomegalovirus. Journal of virology 77, 7563-7574.

Hervas-Stubbs, S., Perez-Gracia, J. L., Rouzaut, A., Sanmamed, M. F., Le Bon, A., and Melero, I. (2011). Direct effects of type I interferons on cells of the immune system. Clinical cancer research: an official journal of the American Association for Cancer Research 17, 2619-2627.

Jaiswal, S., Pazoles, P., Woda, M., Shultz, L. D., Greiner, D. L., Brehm, M. A., and Mathew, A. (2012). Enhanced humoral and HLA-A2-restricted dengue virus-specific T-cell responses in humanized BLT NSG mice. Immunology 136, 334-343.

Kharfan-Dabaja, M. A., Boeckh, M., Wilck, M. B., Langston, A. A., Chu, A. H., Wloch, M. K., Guterwill, D. F., Smith, L. R., Rolland, A. P., and Kenney, R. T. (2012). A novel therapeutic cytomegalovirus DNA vaccine in allogeneic haemopoietic stem-cell transplantation: a randomised, double-blind, placebo-controlled, phase 2 trial. The Lancet infectious diseases 12, 290-299.

Lang, J., Kelly, M., Freed, B. M., McCarter, M. D., Kedl, R. M., Torres, R. M., and Pelanda, R. (2013). Studies of lymphocyte reconstitution in a humanized mouse model reveal a requirement of T cells for human B cell maturation. J Immunol 190, 2090-2101.

Li, N., Huang, X., Zhao, Z., Chen, G., Zhang, W., and Cao, X. (2000). Identification and characterization of a novel gene KE04 differentially expressed by activated human dendritic cells. Biochemical and biophysical research communications 279, 487-493.

Lilja, A. E., and Mason, P. W. (2012). The next generation recombinant human cytomegalovirus vaccine candidates-beyond gB. Vaccine 30, 6980-6990.

Matrai, J., Cantore, A., Bartholomae, C. C., Annoni, A., Wang, W., Acosta-Sanchez, A., Samara-Kuko, E., De Waele, L., Ma, L., Genovese, P., et al. (2011). Hepatocyte-targeted expression by integrase-defective lentiviral vectors induces antigen-specific tolerance in mice with low genotoxic risk. Hepatology 53, 1696-1707.

McGoldrick, S. M., Bleakley, M. E., Guerrero, A., Turtle, C. J., Yamamoto, T. N., Pereira, S. E., Delaney, C. S., and Riddell, S. R. (2013). Cytomegalovirus-specific T cells are primed early after cord blood transplant but fail to control virus in vivo. Blood 121, 2796-2803.

Milano, F., Pergam, S. A., Xie, H., Leisenring, W. M., Gutman, J. A., Riffkin, I., Chow, V., Boeckh, M. J., and Delaney, C. (2011). Intensive strategy to prevent CMV disease in seropositive umbilical cord blood transplant recipients. Blood 118, 5689-5696.

Moutaftsi, M., Mehl, A. M., Borysiewicz, L. K., and Tabi, Z. (2002). Human cytomegalovirus inhibits maturation and impairs function of monocyte-derived dendritic cells. Blood 99, 2913-2921.

Negri, D. R., Rossi, A., Blasi, M., Michelini, Z., Leone, P., Chiantore, M. V., Baroncelli, S., Perretta, G., Cimarelli, A., Klotman, M. E., et al. (2012). Simian immunodeficiency virus-Vpx for improving integrase defective lentiviral vector-based vaccines. Retrovirology 9, 69.

Ohta, E., Misumi, Y., Sohda, M., Fujiwara, T., Yano, A., and Ikehara, Y. (2003). Identification and characterization of GCP16, a novel acylated Golgi protein that interacts with GCP170. The Journal of biological chemistry 278, 51957-51967.

Riegler, S., Hebart, H., Einsele, H., Brossart, P., Jahn, G., and Sinzger, C. (2000). Monocyte-derived dendritic cells are permissive to the complete replicative cycle of human cytomegalovirus. The Journal of general virology 81, 393-399.

Ripperger, T., Tauscher, M., Praulich, I., Pabst, B., Teigler-Schlegel, A., Yeoh, A., Gohring, G., Schlegelberger, B., Flotho, C., Niemeyer, C. M., et al. (2011). Constitutional trisomy 8p11.21-q11.21 mosaicism: a germline alteration predisposing to myeloid leukaemia. British journal of haematology 155, 209-217.

Salguero, G., Sundarasetty, B. S., Borchers, S., Wedekind, D., Eiz-Vesper, B., Velaga, S., Jirmo, A. C., Behrens, G., Warnecke, G., Knofel, A. K., et al. (2011). Preconditioning therapy with lentiviral vector-programmed dendritic cells accelerates the homeostatic expansion of antigen-reactive human T cells in NOD.Rag1-/-.IL-2rgammac-/- mice. Human gene therapy 22, 1209-1224.

Sanchez, V., Greis, K. D., Sztul, E., and Britt, W. J. (2000). Accumulation of virion tegument and envelope proteins in a stable cytoplasmic compartment during human cytomegalovirus replication: characterization of a potential site of virus assembly. Journal of virology 74, 975-986.

Schmidt-Hieber, M., Labopin, M., Beelen, D., Volin, L., Ehninger, G., Finke, J., Socie, G., Schwerdtfeger, R., Kroger, N., Ganser, A., et al. (2013a). CMV serostatus has still an important prognostic impact in de novo acute leukemia patients after allogeneic stem cell transplantation: a report from the acute leukemia working party of EBMT. Blood.

Schmidt-Hieber, M., Labopin, M., Beelen, D., Volin, L., Ehninger, G., Finke, J., Socie, G., Schwerdtfeger, R., Kroger, N., Ganser, A., et al. (2013b). CMV serostatus still has an important prognostic impact in de novo acute leukemia patients after allogeneic stem cell transplantation: a report from the Acute Leukemia Working Party of EBMT. Blood 122, 3359-3364.

Schmidt, M., Schwarzwaelder, K., Bartholomae, C., Zaoui, K., Ball, C., Pilz, I., Braun, S., Glimm, H., and von Kalle, C. (2007). High-resolution insertion-site analysis by linear amplification-mediated PCR (LAM-PCR). Nature methods 4, 1051-1057.

Sinzger, C., Hahn, G., Digel, M., Katona, R., Sampaio, K. L., Messerle, M., Hengel, H., Koszinowski, U., Brune, W., and Adler, B. (2008). Cloning and sequencing of a highly productive, endotheliotropic virus strain derived from human cytomegalovirus TB40/E. The Journal of general virology 89, 359-368.

Soderberg-Naucler, C., Rahbar, A., and Stragliotto, G. (2013). Survival in patients with glioblastoma receiving valganciclovir. The New England journal of medicine 369, 985-986.

Steinman, R. M. (2012). Decisions about dendritic cells: past, present, and future Annual review of immunology 30, 1-22.

Stripecke, R. (2009). Lentiviral vector-mediated genetic programming of mouse and human dendritic cells. Methods Mol Biol 506, 139-158.

Sung, H., and Schleiss, M. R. (2010). Update on the current status of cytomegalovirus vaccines. Expert review of vaccines 9, 1303-1314.

Suzuki, M., Takahashi, T., Katano, I., Ito, R., Ito, M., Harigae, H., Ishii, N., and Sugamura, K. (2012). Induction of human humoral immune responses in a novel HLA-DR-expressing transgenic NOD/Shi-scid/gammacnull mouse. International immunology 24, 243-252.

Szymczak, A. L., and Vignali, D. A. (2005). Development of 2A peptide-based strategies in the design of multicistronic vectors. Expert opinion on biological therapy 5, 627-638.

Taher, C., de Boniface, J., Mohammad, A. A., Religa, P., Hartman, J., Yaiw, K. C., Frisell, J., Rahbar, A., and Soderberg-Naucler, C. (2013). High prevalence of human cytomegalovirus proteins and nucleic acids in primary breast cancer and metastatic sentinel lymph nodes. PloS one 8, e56795.

Verdijk, P., Aarntzen, E. H., Lesterhuis, W. J., Boullart, A. C., Kok, E., van Rossum, M. M., Strijk, S., Eijckeler, F., Bonenkamp, J. J., Jacobs, J. F., et al. (2009). Limited amounts of dendritic cells migrate into the T-cell area of lymph nodes but have high immune activating potential in melanoma patients. Clinical cancer research: an official journal of the American Association for Cancer Research 15, 2531-2540.

Wendland, M., Willenzon, S., Kocks, J., Davalos-Misslitz, A. C., Hammerschmidt, S. I., Schumann, K., Kremmer, E., Sixt, M., Hoffmeyer, A., Pabst, O., et al. (2011). Lymph node T cell homeostasis relies on steady state homing of dendritic cells. Immunity 35, 945-957.

Williams, K. M., Hakim, F. T., and Gress, R. E. (2007). T cell immune reconstitution following lymphodepletion. Seminars in immunology 19, 318-330.

TABLE 1

Significant augmented frequency of human T cells in blood and spleen of mice immunized with SmyleDC compared with ConvDC or non-immunized controls.

| Marker (Week) | Control Mean (%) | SE | n | ConvDC Mean (%) | SE | n | SmyleDC Mean (%) | SE | n | p value SmyleDC vs. Control | p value SmyleDC vs ConvDC |
|---|---|---|---|---|---|---|---|---|---|---|---|
| i. Peripheral Blood |||||||||||||
| CD3 |||||||||||||
| 10 w | 3.32 | 1.28 | 10 | 1.53 | 0.54 | 7 | 1.81 | 0.31 | 22 | 0.65 | 0.67 |
| 13 w | 5.79 | 0.82 | 10 | 7.40 | 3.57 | 7 | 12.04 | 1.88 | 22 | 0.004 | 0.27 |
| 20 w | 11.22 | 4.58 | 10 | 21.06 | 7.85 | 7 | 53.95 | 5.39 | 22 | <0.0001 | 0.0063 |
| CD4 |||||||||||||
| 10 w | 0.47 | 0.32 | 10 | 0.29 | 0.13 | 7 | 0.32 | 0.12 | 22 | 0.60 | 0.92 |
| 13 w | 1.15 | 0.43 | 10 | 5.56 | 3.34 | 7 | 3.94 | 0.96 | 22 | 0.012 | 0.66 |
| 20 w | 2.72 | 1.24 | 10 | 10.02 | 3.82 | 7 | 28.10 | 4.42 | 22 | 0.004 | 0.042 |
| CD8 |||||||||||||
| 10 w | 0.71 | 0.27 | 10 | 0.62 | 0.43 | 7 | 0.80 | 0.15 | 22 | 0.80 | 0.61 |
| 13 w | 1.73 | 0.58 | 10 | 2.13 | 1.20 | 7 | 4.37 | 0.94 | 22 | 0.179 | 0.023 |
| 20 w | 4.25 | 1.94 | 10 | 8.86 | 3.22 | 7 | 19.48 | 2.13 | 22 | 0.0013 | 0.018 |
| ii. Spleen |||||||||||||
| CD45 | 2.8 | 0.9 | | 6.0 | 1.7 | | 15.4 (2.5×) | 3.4 | | 0.001 | 0.010 |
| CD3 | 7.8 | 2.8 | | 3.9 | 1.2 | | 38.2 (10×) | 5.4 | | <0.0001 | <0.0001 |
| CD8 | 3.6 | 1.1 | | 1.7 | 0.5 | | 12.9 (8×) | 2.4 | | 0.001 | <0.0001 |
| CD8 Naïve | 37.5 | 11.1 | | 14.6 | 5.3 | | 12.3 | 4.2 | | 0.030 | 0.370 |
| CD8 EM | 19.3 | 8.2 | | 24.8 | 10.2 | | 38.6 | 7.0 | | 0.040 | 0.140 |
| CD4 | 3.8 | 2.0 | | 1.7 | 0.8 | | 22.9 (13×) | 3.5 | | <0.0001 | <0.0001 |
| CD4 Naïve | 19.2 | 4.9 | | 7.8 | 2.8 | | 10.5 | 3.5 | | 0.037 | 0.276 |
| CD4 EM | 28.6 | 12.1 | | 38.1 | 11.3 | | 51.3 | 7.4 | | 0.100 | 0.340 |

TABLE 2

PCR detection of lentiviral sequences, copies/cell

| | Spleen | Right lymphnode, draining injection site | Left lymph node, contralateral side |
|---|---|---|---|
| Mouse 1 | 0 | 0.036 | 0.003 |
| Mouse 2 | 0.226 | 1.58 | 0.178 |
| Mouse 3 | 0.035 | 1.48 | 0.009 |
| Mouse 4 | 2.06 | 0.03 | 0.02 |
| Mean ± SEM | 0.58025 + 0.49 | 0.7815 + 0.432 | 0.0525 + 0.041 |

TABLE 3

Summary of GVHD analyses for examples 2 and 3

| Experiment | Mice | Human Immune reconstitution | GVHD | Histology or frequency of tolerogenic T cells |
|---|---|---|---|---|
| Adult CD34+ HCT SmyleDC/pp65 2 vectors co-transduction immunization on weeks 10, 11 analyses 20 weeks after HCT (example 2) | 22 | Effector CD4, CD8 T cells and pp65-specific response Mature B cells and pp65-specific response Several cytokines in plasma | No clinical signs of GVHD; no change in weight | Histology: 2/4 GVHD grade 1 in skin; Histology: 3/4 GVHD grade 1 in colon; |
| Adult CD34+ HCT SmyleDC/pp65 2 vectors co-transduction immunization on weeks 10, 11 analyses 45 weeks after HCT (example 2) | 10 | Number of T and B cells reduced | No clinical signs | n.d. |
| Adult CD34+ HCT SmyleDC/pp65 1 vector transduction immunization on weeks 10, 11 analyses 20 weeks after HCT (example 3) | 5 | Effector CD4, CD8 T cells and pp65-specific response pp65-specific antibody responses Several cytokines in plasma (pp65 dependent) | 4 mice without signs of GVHD, 1 mouse with GVHD | n.d. |
| Cord blood CD34+ HCT SmyleDC/pp65 1 vector transduction immunization on weeks 10, 11 analyses 16 weeks after HCT (example 3) | 12 | Effector CD4, CD8 T cells and pp65-specific response pp65-specific antibody responses | No clinical signs | Frequency of Tregs in normal range = 3.45% Frequency of γδ T cells in normal range = 2.08% |
| Cord blood CD34+ HCT SmyleDC/pp65 1 vector transduction immunization on weeks 6, 7, 10, 11 analyses 16 weeks after HCT (example 3) | 9 | Effector CD4, CD8 T cells and pp65-specific response Humoral pp65-specific response | No clinical signs | Frequency of Tregs in normal range = 4.64% Frequency of γδ T cells in normal range = 2.0% |

All together, the data describe above demonstrated:

1. The fundamental difference between conventional human DC vaccines (which are not highly viable or immunologically stable in vitro or in vivo) with our iDC (viable and potent in vitro and in vivo for several weeks).

2. The capacity of iDC once injected subcutaneously to trafficking to the LN-"Anlage", resulting in recruitment of CD4+ and CD8+ cells (particularly represented by effector memory and central memory cells), follicular T helper cells and mature B cells.

3. That iDC administration resulted in adaptive CTL responses measurable as antigen-specific responses against a protein expressed in CMV (pp65).

4. The effects of iDC immunization to stimulate high levels of human IgG production in mice and reactivity against pp65 demonstrating that during the development of human B cells in NRG immunoglobulin class switch occurred.

5. Applicability of safety enhanced integrase-defective lentivirus in iDC reprogramming, which enhances the safety of the genetic programming by lowering the risks of insertional mutagenesis.

6. Realistic perspectives for clinical development and use of iDC, since: 1. Lentiviral vectors are already being used for ex vivo gene transfer in clinical gene therapy protocols, 2. The HSC source we employed is routinely used for clinical HSCT, 3. The pp65 CMV antigen employed is of clinical relevance for stimulation of potent anti-CMV responses in lymphopenic hosts after HSCT.

7. Comparisons between SmyleDCs expressing only GM-CSF and IFN-α and SmyleDC/pp65 iDCs additionally expressing the pp65 antigen of HCMV indicate that the latter type of iDCs is significantly correlated with higher levels of human cytokines and different types of human immunoglobulins in the recipient and causes a faster expansion of B as well as T-cells.

8. In addition to observed expansion of mature T cells in blood and spleen, SmyleDC/pp65 immunizations after UCBT demonstrated higher frequencies of T cell precursors in the thymus. This reflects the capacity of SmyleDC/pp65 to provide homeostatic and/or antigenic signals to enhance thymopoiesis. It is also possible that SmyleDC/pp65 immunization enhances the mobilization of naïve T cells to the periphery, allowing a more constant production of T cell precursors in the thymus.

9. Despite the effective reconstitution of a functioning adaptive human immune system in mice, severe graft-versus-host disease has only been observed in a single mouse out of 58 mice that were similarly transplanted with xenogeneic human stem cells and immunized with donor-derived SmyleDCs loaded with the pp65 immunogen. No clinical GVHD signs were observed in the remaining mice. A cohort of 4 mice analyzed hystopathologically by an experienced pathologist showed in a subset of mice only mild grade 1 GVHD. Immunization with SmyleDC/pp65 administered 4 times modestly increased the frequency of Tregs. Thus, the use of iDCs may potentially improve the outcome in hematopoietic stem cell transplantation using donors who are not fully matched with the recipient as required by current clinical protocols.

The invention claimed is:

1. A method for the regeneration of the immune system of an immunodeficient subject following transplantation of hematopoietic stem cells (HSC) comprising administering a pharmaceutically effective amount to said subject in need thereof of an "induced dendritic cell" (iDC), wherein said induced dendritic cell (iDC) is engineered to express
   a) at least one cytokine which induces the self-differentiation of human dendritic cell (DC) progenitor cells into DCs; and
   b) at least one antigen
   wherein the iDC optionally comprises at least one vector, wherein said vector mediates the expression of said at least one cytokine and the at least one antigen, and wherein said administration of the iDC induces reconstitution of peripheral lymph nodes, and/or increases the frequency and/or absolute numbers of de novo endogenously developed naïve and mature $CD4^+$ T helper cells and cytotoxic $CD8^+$ T cells, and/or increases the frequency and/or absolute numbers of mature B cells and/or increases the production of human immunoglobulins.

2. The method according to claim 1, wherein the vector is a lentiviral vector.

3. The method according to claim 1, wherein the lentiviral vector is integrase defective.

4. The method according to claim 1, wherein the iDC expressing at least one antigen expresses at least one cytokine which induces the self-differentiation of human DC progenitor cells into functional antigen-presenting induced DCs.

5. The method according to claim 1, wherein the cytokine or combination of cytokines is/are selected from the group consisting of GM-CSF, IL-4, IFN-α, IL-15, TGF-B, TNF-α, FLT3L, IL-3, CD40L, FLT3L and IL-3; FLT3L and CD40L; FLT3L and IFN α; GM-CSF and IFN-α and IL-15; GM-CSF and IFN-α and TNF-α; and GM-CSF and IFN-α and TGF-β.

6. The method according to claim 1, wherein one antigen expressed by the iDC is an antigen which can induce a cytotoxic or humoral immune response.

7. The method of claim 6, wherein the humoral immune response is selected from the group consisting of xeno-reactivity, allo-reactivity, neo-reactivity or auto-immunity.

8. The method according to claim 1, wherein the immunodeficiency of the subject is an immunodeficiency selected from the group consisting of immunodeficiency caused by ionizing radiation, immunodeficiency caused by the administration of at least one cytotoxic pharmaceutical, primary immunodeficiency and immunodeficiency caused by a pathogen.

* * * * *

SEQUENCE LISTING

<160> NUMBER OF SEQ ID NOS: 12

<210> SEQ ID NO 1
<211> LENGTH: 4307
<212> TYPE: DNA
<213> ORGANISM: Artificial Sequence
<220> FEATURE:
<221> NAME/KEY: source
<222> LOCATION: 1..4307
<223> OTHER INFORMATION: /mol_type="DNA"
      /note="non-integrating vector derived from HIV-1"
      /organism="Artificial Sequence"

<400> SEQUENCE: 1

| | | | | | |
|---|---|---|---|---|---|
| atgggtgcga | gagcgtcagt | attaagcggg | ggagaattag | atcgatggga | aaaaattcgg | 60 |
| ttaaggccag | ggggaaagaa | aaatataaa | ttaaaacata | tagtatgggc | aagcagggag | 120 |
| ctagaacgat | tcgcagttaa | tcctggcctg | ttagaaacat | cagaaggctg | tagacaaata | 180 |
| ctgggacagc | tacaaccatc | ccttcagaca | ggatcagaag | aacttagatc | attatataat | 240 |
| acagtagcaa | ccctctattg | tgtgcatcaa | aggatagaga | taaaagacac | caaggaagct | 300 |
| ttagacaaga | tagaggaaga | gcaaaacaaa | agtaagaaaa | agcacagca | agcagcagct | 360 |
| gacacaggac | acagcaatca | ggtcagccaa | aattacccta | tagtgcagaa | catccagggg | 420 |
| caaatggtac | atcaggccat | atcacctaga | actttaaatg | catgggtaaa | agtagtagaa | 480 |
| gagaaggctt | tcagcccaga | agtgataccc | atgttttcag | cattatcaga | aggagccacc | 540 |
| ccacaagatt | taaacaccat | gctaaacaca | gtggggggac | atcaagcagc | catgcaaatg | 600 |
| ttaaaagaga | ccatcaatga | ggaagctgca | gaatgggata | gagtgcatcc | agtgcatgca | 660 |
| gggcctattg | caccaggcca | gatgagagaa | ccaaggggaa | gtgacatagc | aggaactact | 720 |
| agtacccttc | aggaacaaat | aggatggatg | acacataatc | cacctatccc | agtaggagaa | 780 |
| atctataaaa | gatggataat | cctgggatta | aataaaatag | taagaatgta | tagccctacc | 840 |
| agcattctgg | acataagaca | aggaccaaag | gaacccttta | gagactatgt | agaccgattc | 900 |
| tataaaactc | taagagccga | gcaagcttca | caagaggtaa | aaaattggat | gacagaaacc | 960 |
| ttgttggtcc | aaaatgcgaa | cccagattgt | aagactattt | taaaagcatt | gggaccagga | 1020 |
| gcgacactag | aagaaatgat | gacagcatgt | cagggagtgg | ggggacccgg | ccataaagca | 1080 |
| agagttttgg | ctgaagcaat | gagccaagta | acaaatccag | ctaccataat | gatacagaaa | 1140 |
| ggcaatttta | ggaaccaaag | aaagactgtt | aagtgtttca | attgtggcaa | agaagggcac | 1200 |
| atagccaaaa | attgcagggc | ccctaggaaa | aagggctgtt | ggaaatgtgg | aaggaagga | 1260 |
| caccaaatga | aagattgtac | tgagagacag | gctaattttt | tagggaagat | ctggccttcc | 1320 |
| cacaagggaa | ggccagggaa | ttttcttcag | agcagaccag | agccaacagc | cccaccagaa | 1380 |
| gagagcttca | ggtttgggga | agagacaaca | actccctctc | agaagcagga | gccgatagac | 1440 |
| aaggaactgt | atcctttagc | ttccctcaga | tcactctttg | gcagcgaccc | ctcgtcacaa | 1500 |
| taaagatagg | ggggcaatta | aaggaagctc | tattagatac | aggagcagat | gatacagtat | 1560 |
| tagaagaaat | gaatttgcca | ggaagatgga | aaccaaaaat | gatagggga | attggaggtt | 1620 |
| ttatcaaagt | aggacagtat | gatcagatac | tcatagaaat | ctgcggacat | aaagctatag | 1680 |
| gtacagtatt | agtaggacct | acacctgtca | acataattg | aagaaatctg | ttgactcaga | 1740 |
| ttggctgcac | tttaaatttt | cccattagtc | ctattgagac | tgtaccagta | aaattaaagc | 1800 |
| caggaatgga | tggcccaaaa | gttaaacaat | ggccattgac | agaagaaaaa | ataaaagcat | 1860 |
| tagtagaaat | ttgtacagaa | atggaaaagg | aaggaaaaat | ttcaaaaatt | gggcctgaaa | 1920 |

```
atccatacaa tactccagta tttgccataa agaaaaaaga cagtactaaa tggagaaaat   1980
tagtagattt cagagaactt aataagagaa ctcaagattt ctgggaagtt caattaggaa   2040
taccacatcc tgcagggtta aaacagaaaa aatcagtaac agtactggat gtgggcgatg   2100 catattttc agttcccta gataaagact tcaggaagta tactgcattt accataccta     2160
gtataaacaa tgagacacca gggattagat atcagtacaa tgtgcttcca cagggatgga   2220
aaggatcacc agcaatattc cagtgtagca tgacaaaaat cttagagcct tttagaaaac   2280
aaaatccaga catagtcatc tatcaataca tggatgattt gtatgtagga tctgacttag   2340
aaatagggca gcatagaaca aaaatagagg aactgagaca acatctgttg aggtggggat   2400
ttaccacacc agacaaaaaa catcagaaag aacctccatt cctttggatg ggttatgaac   2460
tccatcctga taaatggaca gtacagccta tagtgctgcc agaaaaggac agctggactg   2520
tcaatgacat acagaaatta gtgggaaaat tgaattgggc aagtcagatt tatgcaggga   2580
ttaaagtaag gcaattatgt aaacttctta ggggaaccaa agcactaaca gaagtagtac   2640
cactaacaga agaagcagag ctagaactgg cagaaaacag ggagattcta aaagaaccgg   2700
tacatggagt gtattatgac ccatcaaaag acttaatagc agaaatacag aagcaggggc   2760
aaggccaatg gacatatcaa atttatcaag agccatttaa aaatctgaaa acaggaaaat   2820
atgcaagaat gaagggtgcc cacactaatg atgtgaaaca attaacagag gcagtacaaa   2880
aaatagccac agaaagcata gtaatatggg gaaagactcc taaatttaaa ttacccatac   2940
aaaaggaaac atgggaagca tggtggacag agtattggca agccacctgg attcctgagt   3000
gggagtttgt caataccct cccttagtga agttatggta ccagttagag aaagaaccca    3060
taataggagc agaaactttc tatgtagatg gggcagccaa tagggaaact aaattaggaa   3120
aagcaggata tgtaactgac agaggaagac aaaaagttgt ccccctaacg gacacaacaa   3180
atcagaagac tgagttacaa gcaattcatc tagctttgca ggattcggga ttagaagtaa   3240
acatagtgac agactcacaa tatgcattgg gaatcattca agcacaacca gataagagtg   3300
aatcagagtt agtcagtcaa ataatagagc agttaataaa aaaggaaaaa gtctacctgg   3360
catgggtacc agcacacaaa ggaattggag gaaatgaaca agtagatggg ttggtcagtg   3420
ctggaatcag gaaagtacta ttttagatg gaatagataa ggcccaagaa gaacatgaga    3480
aatatcacag taattggaga gcaatggcta gtgattttaa cctaccacct gtagtagcaa   3540
aagaaatagt agccagctgt gataaatgtc agctaaaagg ggaagccatg catggacaag   3600
tagactgtag cccaggaata tggcagctag tttgtacaca tttagaagga aaagttatct   3660
tggtagcagt tcatgtagcc agtggatata tagaagcaga agtaattcca gcagagacag   3720
ggcaagaaac agcatacttc ctcttaaaat tagcaggaag atggccagta aaacagtac    3780 atacagacaa tggcagcaat ttcaccagta ctacagttaa ggccgcctgt tggtgggcgg   3840
ggatcaagca ggaatttggc attccctaca atccccaaag tcaaggagta atagaatcta   3900
tgaataaaga attaaagaaa attataggac aggtaagaga tcaggctgaa catcttaaga   3960
cagcagtaca aatggcagta ttcatccaca attttaaaag aaaagggggg attggggggt   4020
acagtgcagg ggaaagaata gtagacataa tagcaacaga catacaaact aaagaattac   4080
aaaaacaaat tacaaaaatt caaaattttc gggtttatta cagggacagc agagatccag   4140
tttggaaagg accagcaaag ctcctctgga aaggtgaagg ggcagtagta atacaagata   4200
atagtgacat aaaagtagtg ccaagaagaa aagcaaagat catcagggat tatggaaaac   4260
```
agatggcagg tgatgattgt gtggcaagta gacaggatga ggattaa        4307

<210> SEQ ID NO 2
<211> LENGTH: 1686
<212> TYPE: DNA
<213> ORGANISM: Cytomegalovirus
<220> FEATURE:
<221> NAME/KEY: source
<222> LOCATION: 1..1686
<223> OTHER INFORMATION: /mol_type="DNA"
      /organism="Cytomegalovirus"

<400> SEQUENCE: 2

```
atggagtcgc gcggtcgccg ttgtcccgaa atgatatccg tactgggtcc catttcgggg     60
cacgtgctga aagccgtgtt tagtcgcggc gatacgccgg tgctgccgca cgagacgcga    120
ctcctgcaga cgggtatcca cgtacgcgtg agccagccct cgctgatctt ggtatcgcag    180
tacacgcccg actcgacgcc atgccaccgc ggcgacaatc agctgcaggt gcagcacacg    240
tactttacgg gcagcgaggt ggagaacgtg tcggtcaacg tgcacaaccc cacgggccga    300
agcatctgcc ccagccagga gcccatgtcg atctatgtgt acgcgctgcc gctcaagatg    360
ctgaacatcc ccagcatcaa cgtgcaccac tacccgtcgg cggccgagcg caaacaccga    420
cacctgcccg tagctgacgc tgtgattcac gcgtcgggca agcagatgtg gcaggcgcgt    480
ctcacggtct cgggactggc ctggacgcgt cagcagaacc agtggaaaga gcccgacgtc    540
tactacacgt cagcgttcgt gtttcccacc aaggacgtgg cactgcggca cgtggtgtgc    600
gcgcacgagc tggtttgctc catggagaac acgcgcgcaa ccaagatgca ggtgataggt    660
gaccagtacg tcaaggtgta cctggagtcc ttctgcgagg acgtgccctc cggcaagctc    720
tttatgcacg tcacgctggg ctctgacgtg gaagaggacc tgacgatgac ccgcaacccg    780
caacccttca tgcgccccca cgagcgcaac ggctttacgg tgttgtgtcc caaaaatatg    840
ataatcaaac cggcaagat ctcgcacatc atgctggatg tggcttttac ctcacacgag    900
cattttgggc tgctgtgtcc caagagcatc ccgggcctga gcatctcagg taacctgttg    960
atgaacgggc agcagatctt cctggaggta caagccatac gcgagaccgt ggaactgcgt   1020
cagtacgatc ccgtggctgc gctcttcttt ttcgatatcg acttgctgct gcagcgcggg   1080
cctcagtaca gcgagcaccc caccttcacc agccagtatc gcatccaggg caagcttgag   1140
taccgacaca cctgggaccg gcacgacgag ggtgccgccc agggcgacga cgacgtctgg   1200
accagcggat cggactccga cgaagaactc gtaaccaccg agcgcaagac gccccgcgtc   1260
accggcggcg gcgccatggc gggcgcctcc acttccgcgg ccgcaaacg caaatcagca   1320
tcctcggcga cggcgtgcac gtcgggcgtt atgacacgcg ccgccttaa ggccgagtcc   1380
accgtcgcgc ccgaagagga caccgacgag gattccgaca cgaaatccaa caatccggcc   1440
gtgttcacct ggccgccctg gcaggccggc atcctggccc gcaacctggt gcccatggtg   1500
gctacggttc agggtcagaa tctgaagtac caggaattct tctgggacgc caacgacatc   1560
taccgcatct tcgccgaatt ggaaggcgta tggcagcccg ctgcgcaacc caaacgtcgc   1620
cgccaccggc aagacgcctt gcccgggcca tgcatcgcct cgacgcccaa aaagcaccga   1680
ggttga                                                              1686
```

<210> SEQ ID NO 3
<211> LENGTH: 432
<212> TYPE: DNA
<213> ORGANISM: Homo sapiens
<220> FEATURE:

<221> NAME/KEY: source
<222> LOCATION: 1..432
<223> OTHER INFORMATION: /mol_type="DNA"
      /organism="Homo sapiens"

<400> SEQUENCE: 3

```
atgtggctgc agagcctgct gctcttgggc actgtggcct gcagcatctc tgcacccgcc      60
cgctcgccca gccccagcac gcagccctgg gagcatgtga atgccatcca ggaggcccgg     120
cgtctcctga acctgagtag agacactgct gctgagatga atgaaacagt agaagtcatc     180
tcagaaatgt ttgacctcca ggagccgacc tgcctacaga cccgcctgga gctgtacaag     240
cagggcctgc ggggcagcct caccaagctc aagggcccct tgaccatgat agccagccac     300
tacaagcagc actgccctcc aaccccggaa acttcctgtg caacccagat tatcaccttt     360
gaaagtttca agagaaacct gaaggacttt ctgcttgtca tcccctttga ctgctgggag     420
ccagtccagg ag                                                         432
```

<210> SEQ ID NO 4
<211> LENGTH: 550
<212> TYPE: DNA
<213> ORGANISM: Homo sapiens
<220> FEATURE:
<221> NAME/KEY: source
<222> LOCATION: 1..550
<223> OTHER INFORMATION: /mol_type="DNA"
      /organism="Homo sapiens"

<400> SEQUENCE: 4

```
atggccttga cctttgcttt actggtggcc ctcctggtgc tcagctgcaa gtcaagctgc      60
tctgtgggct gtgatctgcc tcaaacccac agcctgggta gcaggaggac cttgatgctc     120
ctggcacaga tgaggagaat ctctcttttc tcctgcttga aggacagaca tgactttgga     180
tttccccagg aggagtttgg caaccagttc caaaaggctg aaaccatccc tgtcctccat     240
gagatgatcc agcagatctt caatctcttc agcacaaagg actcatctgc tgcttgggat     300
gagaccctcc tagacaaatt ctacactgaa ctctaccagc agctgaatga cctggaagcc     360
tgtgtgatac aggggtgggg ggtgacagag actcccctga tgaaggagga ctccattctg     420
gctgtgagga atacttccaa agaatcactc tctatctga aagagaagaa atacagccct     480
tgtgcctggg aggttgtcag agcagaaatc atgagatctt tttctttgtc aacaaacttg     540
caagaaagtt                                                            550
```

<210> SEQ ID NO 5
<211> LENGTH: 66
<212> TYPE: DNA
<213> ORGANISM: Artificial Sequence
<220> FEATURE:
<221> NAME/KEY: source
<222> LOCATION: 1..66
<223> OTHER INFORMATION: /mol_type="DNA"
      /note="nucleic acid encoding an artificial virus-derived
      linkerpolypeptide"
      /organism="Artificial Sequence"

<400> SEQUENCE: 5

```
ggatccggag ccacgaactt ctctctgtta aagcaagcag gagacgtgga agaaaacccc      60
ggtcct                                                                66
```

<210> SEQ ID NO 6
<211> LENGTH: 69
<212> TYPE: DNA

```
<213> ORGANISM: Artificial Sequence
<220> FEATURE:
<221> NAME/KEY: source
<222> LOCATION: 1..69
<223> OTHER INFORMATION: /mol_type="DNA"
      /note="nucleic acid encoding an artificial virus-derived linker"
      /organism="Artificial Sequence"

<400> SEQUENCE: 6
ccggtgaaac agactttgaa ttttgacctt ctcaagttgg cgggagacgt ggagtccaac       60
ccagggccc                                                              69

<210> SEQ ID NO 7
<211> LENGTH: 92
<212> TYPE: DNA
<213> ORGANISM: artificial sequences
<220> FEATURE:
<221> NAME/KEY: source
<222> LOCATION: 1..92
<223> OTHER INFORMATION: /mol_type="DNA"
      /note="PCR primer"
      /organism="artificial sequences"

<400> SEQUENCE: 7
ccggtgaaac agactttgaa ttttgacctt ctcaagttgg cgggagacgt ggagtccaac       60
ccagggccca tggagtcgcg cggtcgccgt tg                                    92

<210> SEQ ID NO 8
<211> LENGTH: 88
<212> TYPE: DNA
<213> ORGANISM: artificial sequences
<220> FEATURE:
<221> NAME/KEY: source
<222> LOCATION: 1..88
<223> OTHER INFORMATION: /mol_type="DNA"
      /note="PCR primer"
      /organism="artificial sequences"

<400> SEQUENCE: 8
tgggttggac tccacgtctc ccgccaactt gagaaggtca aaattcaaag tctgtttcac       60
cggttcctta cttcttaaac tttcttgc                                         88

<210> SEQ ID NO 9
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="PCR primer"
      /organism="artificial sequences"

<400> SEQUENCE: 9
gaggagttgt ggcccgttgt                                                  20

<210> SEQ ID NO 10
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="PCR primer"
      /organism="artificial sequences"

<400> SEQUENCE: 10
```

```
tgacaggtgg tggcaatgcc                                               20

<210> SEQ ID NO 11
<211> LENGTH: 22
<212> TYPE: DNA
<213> ORGANISM: artificial sequences
<220> FEATURE:
<221> NAME/KEY: source
<222> LOCATION: 1..22
<223> OTHER INFORMATION: /mol_type="DNA"
      /note="PCR primer"
      /organism="artificial sequences"

<400> SEQUENCE: 11
tctccattcc ctatgttcat gc                                            22

<210> SEQ ID NO 12
<211> LENGTH: 22
<212> TYPE: DNA
<213> ORGANISM: artificial sequences
<220> FEATURE:
<221> NAME/KEY: source
<222> LOCATION: 1..22
<223> OTHER INFORMATION: /mol_type="DNA"
      /note="PCR primer"
      /organism="artificial sequences"

<400> SEQUENCE: 12
gttcccgcag aatggtgagg tg                                            22
```